(12) United States Patent
Tanaka et al.

(10) Patent No.: US 10,709,133 B2
(45) Date of Patent: Jul. 14, 2020

(54) CONDENSED HETEROCYCLIC COMPOUND

(71) Applicant: Sumitomo Chemical Company, Limited, Tokyo (JP)

(72) Inventors: Ayaka Tanaka, Takarazuka (JP); Daisuke Oohira, Takarazuka (JP); Takayuki Shioda, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 238 days.

(21) Appl. No.: 15/773,011

(22) PCT Filed: Oct. 31, 2016

(86) PCT No.: PCT/JP2016/082224
§ 371 (c)(1),
(2) Date: May 2, 2018

(87) PCT Pub. No.: WO2017/077968
PCT Pub. Date: May 11, 2017

(65) Prior Publication Data
US 2018/0317492 A1    Nov. 8, 2018

(30) Foreign Application Priority Data

Nov. 5, 2015   (JP) ................... 2015-217310

(51) Int. Cl.
| | | |
|---|---|---|
| A01N 43/90 | (2006.01) | |
| C07D 519/00 | (2006.01) | |
| C07D 471/04 | (2006.01) | |
| A61K 31/437 | (2006.01) | |
| A01N 47/02 | (2006.01) | |
| A61P 33/00 | (2006.01) | |

(52) U.S. Cl.
CPC ............. *A01N 43/90* (2013.01); *A01N 47/02* (2013.01); *A61K 31/437* (2013.01); *A61P 33/00* (2018.01); *C07D 471/04* (2013.01); *C07D 519/00* (2013.01)

(58) Field of Classification Search
CPC ............................ A61K 31/437; A61P 33/00
See application file for complete search history.

(56) References Cited

U.S. PATENT DOCUMENTS

| | | |
|---|---|---|
| 2004/0235865 A1 | 11/2004 | Ikegami |
| 2014/0194290 A1 | 7/2014 | Takahashi et al. |
| 2015/0197532 A1 | 7/2015 | Takahashi et al. |

(Continued)

FOREIGN PATENT DOCUMENTS

| | | |
|---|---|---|
| CA | 3002888 A1 | 5/2017 |
| WO | 03022850 A1 | 3/2003 |

(Continued)

OTHER PUBLICATIONS

English Translation of International Preliminary Report on Patentability dated May 8, 2018 in International Application No. PCT/JP2016/082224.
English Translation of International Search Report dated Dec. 13, 2016 in International Application No. PCT/JP2016/082224.
Extended European Search Report dated May 17, 2019 in EP Application No. 16862028.4.

(Continued)

*Primary Examiner* — Kortney L. Klinkel
(74) *Attorney, Agent, or Firm* — Panitch Schwarze Belisario & Nadel LLP

(57) ABSTRACT

A condensed heterocyclic compound represented by formula (II), in which Q represents a group represented by formula Q-1 or a group represented by formula Q-2, has an excellent control effect on arthropod pests (wherein, Z represents a nitrogen atom or $CX^2$, $X^1$ and $X^2$ each independently represent a hydrogen atom, a C1-C6 chain hydrocarbon group optionally having one or more substituent selected from group B, a phenyl group optionally having one or more substituent selected from group C, or the like, $A^1$ represents NH, $NCH_3$, or the like, $A^2$ represents a nitrogen atom or CH, $A^3$ represents a nitrogen atom or $CR^4$, $R^1$ represents a C1-C5 perfluoroalkyl group or the like, and n, p, q, and r each independently represent 0, 1, or 2).

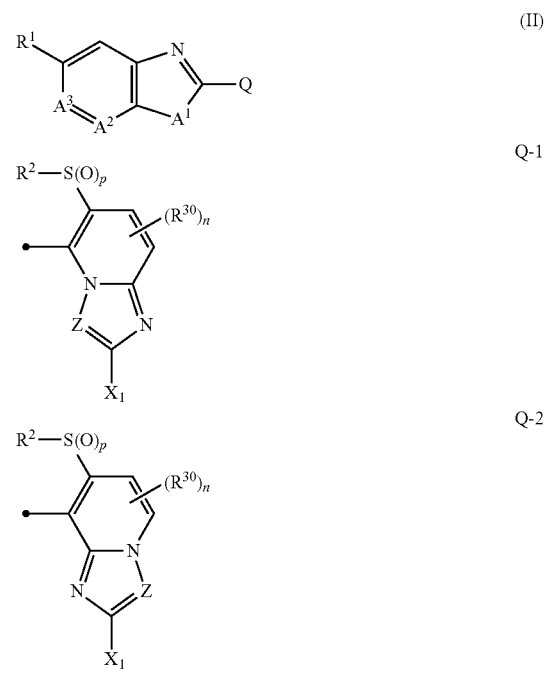

15 Claims, No Drawings

(56) References Cited

U.S. PATENT DOCUMENTS

| | | |
|---|---|---|
| 2016/0009715 A1 | 1/2016 | Takahashi et al. |
| 2016/0159743 A1 | 6/2016 | Takahashi et al. |
| 2018/0022760 A1 | 1/2018 | Kudo et al. |
| 2018/0116222 A1 | 5/2018 | Fischer et al. |

FOREIGN PATENT DOCUMENTS

| | | |
|---|---|---|
| WO | 2011090127 A1 | 7/2011 |
| WO | 2013018928 A1 | 2/2013 |
| WO | 2015000715 A1 | 1/2015 |
| WO | 2016091731 A1 | 6/2016 |
| WO | 2016107742 A1 | 7/2016 |
| WO | 2016129684 A1 | 8/2016 |
| WO | 2016142327 A1 | 9/2016 |
| WO | 2016162318 A1 | 10/2016 |
| WO | 2017026384 A1 | 2/2017 |
| WO | 2017061497 A1 | 4/2017 |
| WO | 2017072039 A1 | 5/2017 |

OTHER PUBLICATIONS

Office Action dated Feb. 27, 2020 in IN Application No. 201847020218.
Office Action dated Mar. 12, 2020 in CN Application No. 201680063393.8.

CONDENSED HETEROCYCLIC COMPOUND

CROSS-REFERENCE TO RELATED APPLICATION

This application is a Section 371 of International Application No. PCT/JP2016/082224, filed Oct. 31, 2016, which was published in the Japanese language on May 11, 2017, under International Publication No. WO 2017/077968 A1, which claims priority under 35 U.S.C. § 119(b) to Japanese Application No. 2015-217310, filed Nov. 5, 2015, the disclosures of which are incorporated herein by reference in their entirety.

TECHNICAL FIELD

The present invention relates to a certain type of fused heterocyclic compounds and use of said compounds for controlling harmful arthropods.

BACKGROUND ART

To date, some compounds for controlling harmful arthropods have been developed and come into practical use (see, for example, Patent Document 1).

CITATION LIST

Patent Document

Patent Document 1: WO 2013/018928

SUMMARY OF THE INVENTION

Problems to be Solved by Invention

An object of the present invention is to provide a compound that has an excellent efficacy for controlling harmful arthropods.

Means to Solve Problems

[1] A compound represented by formula (II):

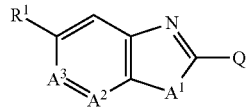

(II)

in which Q represents a group represented by formula Q-1 or a group represented by formula Q-2,

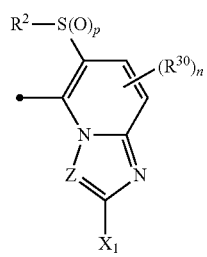

Q-1

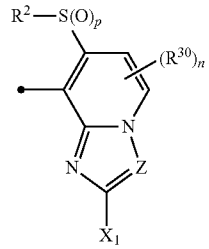

Q-2 wherein

Z represents a nitrogen atom or $CX^2$, $X^1$ and $X^2$ each independently represent a hydrogen atom, a C1-C6 chain hydrocarbon group optionally having one or more substituents selected from group B, a phenyl group optionally having one or more substituents selected from group C, a 5 or 6 membered aromatic heterocyclic group optionally having one or more substituents selected from group C, a C3-C6 alicyclic hydrocarbon group optionally having one or more substituents selected from group C, a halogen atom, a cyano group, a nitro group, a sulfanyl group, $OR^a$, $NR^bR^c$, $C(O)OR^d$, $C(O)NR^eR^f$, $NR^iC(O)R^g$, $NR^iC(O)OR^h$, or $S(O)_qR^i$, $A^1$ represents NH, NCH$_3$, an oxygen atom, or a sulfur atom, $A^2$ represents a nitrogen atom or CH, $A^3$ represents a nitrogen atom or $CR^4$, $R^1$ represents a C1-C5 perfluoroalkyl group, $S(O)R^5$, or $OS(O)_2R^5$, n, p, q, and r each independently represent 0, 1, or 2, $R^2$ represents a C1-C6 alkyl group optionally having one or more halogen atoms, a cyclopropylmethyl group, or a cyclopropyl group, $R^{30}$ represents a C1-C6 chain hydrocarbon group optionally having one or more substituents selected from group B, a C3-C7 cycloalkyl group optionally having one or more substituents selected from group E, a phenyl group optionally having one or more substituents selected from group H, a 5 or 6 membered aromatic heterocyclic group optionally having one or more substituents selected from group H, $OR^{12}$, $NR^{11}R^{12}$, $NR^{11a}R^{12a}$, $NR^{29}NR^{11}R^{12}$, —$NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15}R^{16}$, $NR^{24}NR^{11}C(O)NR^{15}R^{16}$, —N=CHNR$^{15}$R$^{16}$, N=S(O)$_x$R$^{15}$R$^{16}$, $C(O)OR^{17}$, a cyano group, a nitro group, or a halogen atom, $R^{11}$, $R^{17}$, $R^{24}$, and $R^{29}$ each independently represent a hydrogen atom, or a C1-C6 chain hydrocarbon group optionally having one or more halogen atoms, $R^{11a}$ and $R^{12a}$ are taken together with the nitrogen atom to which they are attached to form a 3 to 7 membered non-aromatic heterocyclic group optionally having one or more substituents selected from group E, $R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from group H, or a 5 or 6 membered aromatic heterocyclic group optionally having one or more substituents selected from group H, $R^{14}$ represents a C1-C6 chain hydrocarbon group optionally having one or more halogen atoms, a C3-C7 cycloalkyl group optionally having one or more halogen atoms, a

3

(C3-C6 cycloalkyl)C1-C3 alkyl group optionally having one or more halogen atoms, or a phenyl C1-C3 alkyl group wherein a phenyl moiety of the phenyl C1-C3 alkyl group may optionally have one or more substituents selected from group H, $R^{15}$ and $R^{16}$ each independently represent a C1-C6 alkyl group optionally having one or more halogen atoms, $R^{12}$ represents a hydrogen atom, $S(O)_2R^{23}$, a C1-C6 chain hydrocarbon group optionally having one or more halogen atoms, or a C1-C6 alkyl group having one substituent selected from group F, $R^{23}$ represents a C1-C6 chain hydrocarbon group optionally having one or more halogen atoms, or a phenyl group optionally having one or more substituents selected from group H, $R^4$ represents a hydrogen atom, a C1-C6 alkyl group optionally having one or more halogen atoms, or a halogen atom, $R^5$ represents a C1-C5 perfluoroalkyl group, $R^a$, $R^b$, and $R^c$ each independently represent a hydrogen atom, or a C1-C6 chain hydrocarbon group optionally having one or more halogen atoms, $R^d$ represents a hydrogen atom or a C1-C6 chain hydrocarbon group, $R^e$ and $R^f$ each independently represent a hydrogen atom, a C1-C6 chain hydrocarbon group optionally having one or more halogen atoms, or a C3-C6 alicyclic hydrocarbon group optionally having one or more halogen atoms, $R^g$ and $R^h$ each independently represent a hydrogen atom, a C1-C6 chain hydrocarbon group optionally having one or more halogen atoms, a C3-C6 alicyclic hydrocarbon group optionally having one or more halogen atoms, or a phenyl group, $R^i$ represents a C1-C6 chain hydrocarbon group optionally having one or more halogen atoms, $R^j$ represents a hydrogen atom or a C1-C6 alkyl group, group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom, group C: a group consisting of a C1-C6 alkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom, group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally

4 having one or more halogen atoms, a halogen atom, an oxo group, a hydroxyl group, a cyano group, and a nitro group, group F: a group consisting of a C1-C6 alkoxy group optionally having one or more halogen atoms, an amino group, $NHR^{21}$, $NR^{21}R^{22}$, a cyano group, a phenyl group optionally having one or more substituents selected from group H, a 5 or 6 membered aromatic heterocyclic group optionally having one or more substituents selected from group H, a C3-C7 cycloalkyl group optionally having one or more halogen atoms, and a 3 to 7 membered non-aromatic heterocyclic group optionally having one or more substituents selected from group C, group H: a group consisting of a halogen atom, a nitro group, a cyano group, an amino group, a 5 or 6 membered aromatic heterocyclic group, a C1-C6 alkyl group optionally having one or more halogen atoms, $OR^{100}$, $NR^9R^{100}$, $C(O)R^{100}$, $C(O)NR^9R^{100}$, $OC(O)R^9$, $OC(O)OR^9$, $NR^{100}C(O)R$, $NR^{100}C(O)OR^9$, and $C(O)OR^{100}$, $R^9$ represents a C1-C6 alkyl group optionally having one or more halogen atoms, or a C3-C6 cycloalkyl group optionally having one or more halogen atoms, and $R^{100}$ represents a hydrogen atom, a C1-C6 alkyl group optionally having one or more halogen atoms, or a C3-C6 cycloalkyl group optionally having one or more halogen atoms (hereinafter, a compound represented by formula (II) is also referred to as "present compound A").

[2] The compound according to [1] represented by formula (I):

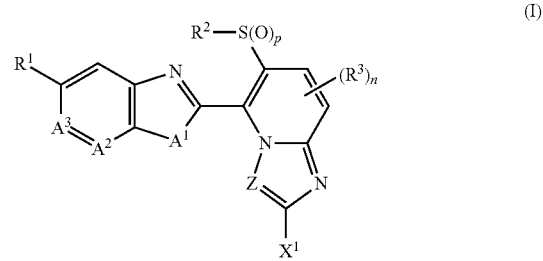

wherein

Z represents a nitrogen atom or $CX^2$, $X^1$ and $X^2$ each independently represent a hydrogen atom, a C1-C6 chain hydrocarbon group optionally having one or more substituents selected from group B, a phenyl group optionally having one or more substituents selected from group C, a 5 or 6 membered aromatic heterocyclic group optionally having one or more substituents selected from group C, a C3-C6 alicyclic hydrocarbon group optionally having one or more substituents selected from group C, a halogen atom, a cyano group, a nitro group, a sulfanyl group, $OR^a$, $NR^bR^c$, $C(O)OR^d$, $C(O)NR^eR^f$, $NR^jC(O)R^g$, $NR^jC(O)OR^h$, or $S(O)_qR^i$, $A^1$ represents NH, $NCH_3$, an oxygen atom, or a sulfur atom, $A^2$ represents a nitrogen atom or CH, $A^3$ represents a nitrogen atom or $CR^4$, $R^1$ represents a C1-C5 perfluoroalkyl group, $S(O)_rR^5$, or $OS(O)_2R^5$, n, p, q, and r each independently represent 0, 1, or 2, $R^2$ represents a C1-C6 alkyl group optionally having one or more halogen atoms, a cyclopropylmethyl group, or a cyclopropyl group, R³ represents a C1-C6 alkyl group optionally having one or more halogen atoms, or a halogen atom, R⁴ represents a hydrogen atom, a C1-C6 alkyl group optionally having one or more halogen atoms, or a halogen atom, R⁵ represents a C1-C5 perfluoroalkyl group, $R^a$, $R^b$, and $R^c$ each independently represent a hydrogen atom, or a C1-C6 chain hydrocarbon group optionally having one or more halogen atoms, $R^d$ represents a hydrogen atom, or a C1-C6 chain hydrocarbon group, $R^e$ and $R^f$ each independently represent a hydrogen atom, a C1-C6 chain hydrocarbon group optionally having one or more halogen atoms, or a C3-C6 alicyclic hydrocarbon group optionally having one or more halogen atoms, $R^g$ and $R^h$ each independently represent a hydrogen atom, a C1-C6 chain hydrocarbon group optionally having one or more halogen atoms, a C3-C6 alicyclic hydrocarbon group optionally having one or more halogen atoms, or a phenyl group, $R^i$ represents a C1-C6 chain hydrocarbon group optionally having one or more halogen atoms, $R^j$ represents a hydrogen atom or a C1-C6 alkyl group, group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom, group C: a group consisting of a C1-C6 alkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom (hereinafter, a compound represented by formula (I) is also referred to as "present compound B").

[3] The compound according to [1] or [2], wherein $A^1$ represents an oxygen atom.

[4] The compound according to [1] or [2], wherein $A^1$ represents $NCH_3$.

[5] The compound according to any one of [1] to [4], wherein $A^2$ represents a nitrogen atom, and $A^3$ represents CH.

[6] The compound according to any one of [1] to [4], wherein $A^2$ represents CH, and $A^3$ represents CH.

[7] The compound according to any one of [1] to [6], wherein Z represents a nitrogen atom.

[8] The compound according to any one of [1] to [6], wherein Z represents CH.

[9] The compound according to any one of [1] to [8], wherein $R^2$ represents a C1-C3 alkyl group.

[10] The compound according to any one of [1] to [9], wherein $X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, and $R^a$, $R^b$, $R^c$, $R^d$, $R^e$, and $R^f$ each independently represent a hydrogen atom or a C1-C6 alkyl group.

[11] The compound according to [1] or [2], wherein Z represents a nitrogen atom or CH, $A^1$ represents an oxygen atom, $A^2$ represents CH, $A^3$ represents CH, $X^1$ represents a hydrogen atom, a C1-C6 alkyl group optionally having one or more halogen atoms, $NR^bR^c$, $C(O)OR^d$, a halogen atom, or a phenyl group, $R^b$, $R^c$, and $R^d$ represent a hydrogen atom or a C1-C6 alkyl group, $R^1$ represents a C1-C5 perfluoroalkyl group or $S(O)_nR^5$, $R^2$ represents a C1-C3 alkyl group, and n represents 0 or 1.

[12] The compound according to [1] or [2], wherein Z represents a nitrogen atom or CH, $A^1$ represents $NCH_3$, $A^2$ represents a nitrogen atom, $A^3$ represents CH, $X^1$ represents a hydrogen atom, a C1-C6 alkyl group optionally having one or more halogen atoms, $NR^bR^c$, $C(O)OR^d$, a halogen atom, or a phenyl group, $R^b$, $R^c$, and $R^d$ represent a hydrogen atom or a C1-C6 alkyl group, $R^1$ represents a C1-C5 perfluoroalkyl group, $R^2$ represents a C1-C3 alkyl group, and n represents 0 or 1.

[13] The compound according to [1], wherein Z represents a nitrogen atom or CH, $X^1$ represents a hydrogen atom, a C1-C6 alkyl group optionally having one or more halogen atoms, $NR^bR^c$, $C(O)OR^d$, a halogen atom, or a phenyl group, $R^b$, $R^c$, $R^d$ represent a hydrogen atom or a C1-C6 alkyl group, $R^1$ represents a C1-C5 perfluoroalkyl group, $R^2$ represents a C1-C3 alkyl group, $R^{30}$ represents a C1-C6 alkyl group optionally having one or more halogen atoms, a C3-C7 cycloalkyl group optionally having a cyano group, a halogen atom, or a phenyl group having a C1-C6 alkyl group optionally having one or more halogen atoms or a halogen atom, and n represents 0 or 1.

[14] A composition for controlling a harmful arthropod, comprising the compound according to any one of [1] to [13], and an inert carrier.

[15] A method for controlling a harmful arthropod, comprising applying an effective amount of the compound according to any one of [1] to [13] to a harmful arthropod or a habitat where the harmful arthropod lives.

As used herein, the present compound A or the present compound B is referred to as "present compound".

Effect of Invention

The present compound has an excellent control efficacy against harmful arthropods and hence is useful as an active ingredient in an agent for controlling harmful arthropods.

MODE FOR CARRYING OUT THE INVENTION

The groups as used herein are explained as follows.

The "optionally having one or more halogen atoms" as used herein represents that when two or more halogen atoms are present, the halogen atoms may be identical to or different from each other.

The expression "CX-CY" as used herein represents that the number of carbon atoms is from X to Y. For example, the expression "C1-C6" represents that the number of carbon atoms is from 1 to 6.

The term "halogen atom" represents fluorine atom, chlorine atom, bromine atom, or iodine atom.

The term "chain hydrocarbon group" represents an alkyl group, an alkenyl group, or an alkynyl group.

Examples of the "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, and hexyl group.

Examples of the "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group.

Examples of the "alkynyl group" include ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.

The term "alicyclic hydrocarbon group" represents a cycloalkyl group or a cycloalkenyl group.

Examples of the "cycloalkyl group" include cyclopropyl group, cyclobutyl group, cyclopentyl group, and cyclohexyl group.

Examples of the "cycloalkenyl group" include cyclopropenyl group, cyclopentenyl group, and cyclohexenyl group.

The term "C1-C5 perfluoroalkyl group" represents a group wherein all of hydrogen atoms in the C1-C5 alkyl group are substituted by fluoro atoms, and includes, for example, trifluoromethyl group, perfluoroethyl group, 1,2,2,2-tetrafluoro-1-(trifluoromethyl)ethyl group, and perfluoropentyl group.

The term "5 or 6 membered aromatic heterocyclic group" represents pyrrolyl group, furyl group, thienyl group, pyrazolyl group, imidazolyl group, triazolyl group, tetrazolyl group, oxazolyl group, isoxazolyl group, thiazolyl group, oxadiazolyl group, thiadiazolyl group, pyridyl group, pyridazinyl group, pyrimidinyl group, or pyrazinyl group.

Embodiments of the present compound include the following compounds.

Embodiment 1

A present compound wherein Z represents a nitrogen atom.

Embodiment 2

A present compound wherein Z represents $CX^2$.

Embodiment 3

A present compound wherein Z represents CH.

Embodiment 4

A present compound wherein Z represents a nitrogen atom or CH.

Embodiment 5

A present compound wherein $A^1$ represents $NCH_3$ or an oxygen atom.

Embodiment 6

A present compound wherein $A^1$ represents $NCH_3$.

Embodiment 7

A present compound wherein $A^1$ represents an oxygen atom.

Embodiment 8

A present compound, wherein
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, and
n represents 0 or 1.

Embodiment 9

A present compound, wherein
$A^3$ represents CH,
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, and
n represents 0 or 1.

Embodiment 10

A present compound, wherein
$A^2$ represents CH,
$A^3$ represents CH,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 11

A present compound, wherein
$A^2$ represents CH,
$A^3$ represents a nitrogen atom,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^2$ represents a C1-C6 alkyl group optionally having one or more halogen atoms, and n represents 0 or 1.

Embodiment 12

A present compound, wherein
$A^2$ represents a nitrogen atom,
$A^3$ represents CH,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 13

A present compound, wherein
$A^2$ represents a nitrogen atom,
$A^3$ represents a nitrogen atom,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 14

A present compound, wherein
$A^1$ represents $NCH_3$ or an oxygen atom,
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, and
n represents 0 or 1.

Embodiment 15

A present compound, wherein
$A^1$ represents $NCH_3$ or an oxygen atom,
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^1$ represents a C1-C5 perfluoroalkyl group,
$R^2$ represents a C1-C3 alkyl group, and
n represents 0 or 1.

Embodiment 16

A present compound, wherein
$A^1$ represents $NCH_3$ or an oxygen atom,
$A^3$ represents CH,
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^1$ represents a C1-C5 perfluoroalkyl group,
$R^2$ represents a C1-C3 alkyl group, and
n represents 0 or 1.

Embodiment 17

A present compound, wherein
$A^1$ represents $NCH_3$ or an oxygen atom,
$A^3$ represents CH,
$X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ each independently represent a hydrogen atom or a C1-C6 alkyl group,
$R^1$ represents a C1-C5 perfluoroalkyl group or $S(O)_rR^5$,
$R^2$ represents a C1-C3 alkyl group, and
n represents 0 or 1.

Embodiment 18

A present compound represented by formula (I-A):

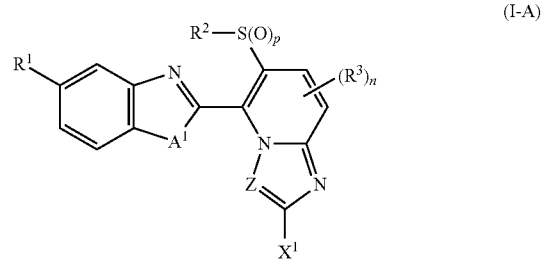

(I-A)

wherein the symbols are the same as defined above.

Embodiment 19

The compound of the Embodiment 18, wherein $A^1$ represents $NCH_3$ or an oxygen atom.

Embodiment 20

The compound of the Embodiment 19, wherein
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C3 alkyl group, and
n represents 0 or 1.

Embodiment 21

The compound of the Embodiment 19, wherein
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^1$ represents a C1-C5 perfluoroalkyl group or $S(O)_rR^5$, $R^2$ represents a C1-C3 alkyl group, and n represents 0 or 1.

Embodiment 22

The compound of the Embodiment 19, wherein $X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group, $R^2$ represents a C1-C3 alkyl group, and n represents 0 or 1.

Embodiment 23

The compound of the Embodiment 19, wherein $X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group, $R^1$ represents a C1-C5 perfluoroalkyl group or $S(O)_rR^5$, $R^2$ represents a C1-C3 alkyl group, and n represents 0 or 1.

Embodiment 24

A present compound represented by formula (I-C):

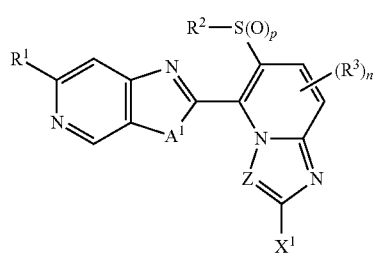

(I-C)

wherein the symbols are the same as defined above.

Embodiment 25

The compound of the Embodiment 24, wherein $A^1$ represents $NCH_3$ or an oxygen atom.

Embodiment 26

The compound of the Embodiment 25, wherein $X^1$ represents a hydrogen atom, a halogen atom, a methyl group, $CF_3$, or an amino group, $R^1$ represents a C1-C5 perfluoroalkyl group, $R^2$ represents a C1-C3 alkyl group, and n represents 0.

Embodiment 27

A present compound represented by formula (I-B):

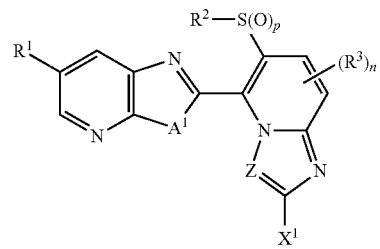

(I-B)

wherein the symbols are the same as defined above.

Embodiment 28

The compound of the Embodiment 27, wherein $A^1$ represents $NCH_3$ or an oxygen atom.

Embodiment 29

The compound of the Embodiment 28, wherein $X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^2$ represents a C1-C3 alkyl group, and n represents 0 or 1.

Embodiment 30

The compound of the Embodiment 28, wherein $X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^1$ represents a C1-C5 perfluoroalkyl group or $S(O)_rR^5$, $R^2$ represents a C1-C3 alkyl group, and n represents 0 or 1.

Embodiment 31

The compound of the Embodiment 28, wherein $X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group, $R^2$ represents a C1-C3 alkyl group, and n represents 0 or 1.

Embodiment 32

The compound of the Embodiment 28, wherein $X^1$ represents a hydrogen atom, a C1-C6 alkyl group optionally having one or more halogen atoms, $NR^bR^c$, C(O)OR$^d$, a halogen atom, or a phenyl group, wherein R$^b$, R$^c$, and R$^d$ represent a hydrogen atom or a C1-C6 alkyl group,
R$^1$ represents a C1-C5 perfluoroalkyl group or S(O)$_r$R$^5$,
R$^2$ represents a C1-C3 alkyl group, and
n represents 0 or 1.

Embodiment 33

A present compound represented by formula (I-D):

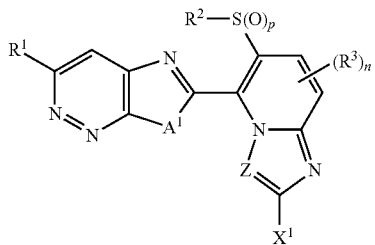

(I-D)

wherein the symbols are the same as defined above.

Embodiment 34

The compound of the Embodiment 33, wherein A represents NCH$_3$ or an oxygen atom.

Embodiment 35

The compound of the Embodiment 34, wherein
X$^1$ represents a hydrogen atom, a halogen atom, a methyl group, CF$_3$, or an amino group,
R$^1$ represents a C1-C5 perfluoroalkyl group,
R$^2$ represents a C1-C3 alkyl group, and
n represents 0.

Embodiment 36

A present compound represented by formula (I-E):

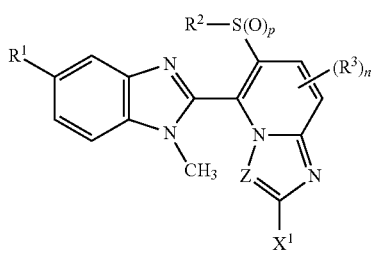

(I-E)

wherein the symbols are the same as defined above.

Embodiment 37

The compound of the Embodiment 36, wherein
X$^1$ represents a hydrogen atom, a C1-C6 alkyl group optionally having one or more halogen atoms, a phenyl group optionally having one or more halogen atoms, a halogen atom, OR$^a$, NR$^b$R$^c$, C(O)OR$^d$, or C(O)NR$^e$R$^f$, wherein R$^a$, R$^b$, R$^c$, R$^d$, R$^e$, and R$^f$ each independently represent a hydrogen atom or a C1-C6 alkyl group,
R$^2$ represents a C1-C3 alkyl group, and
n represents 0 or 1.

Embodiment 38

The compound of the Embodiment 36, wherein
X$^1$ represents a hydrogen atom, a C1-C6 alkyl group optionally having one or more halogen atoms, a phenyl group optionally having one or more halogen atoms, a halogen atom, OR$^a$, NR$^b$R$^c$, C(O)OR$^d$, or C(O)NR$^e$R$^f$, wherein R$^a$, R$^b$, R$^c$, R$^d$, R$^e$, and R$^f$ each independently represent a hydrogen atom or a C1-C6 alkyl group,
R$^1$ represents a C1-C5 perfluoroalkyl group or S(O)$_r$R$^5$,
R$^2$ represents a C1-C3 alkyl group, and
n represents 0 or 1.

Embodiment 39

The compound of the Embodiment 36, wherein
X$^1$ represents a hydrogen atom, a C1-C6 alkyl group optionally having one or more halogen atoms, NR$^b$R$^c$, C(O)OR$^d$, a halogen atom, or a phenyl group, wherein R$^b$, R$^c$, and R$^d$ represent a hydrogen atom or a C1-C6 alkyl group,
R$^2$ represents a C1-C3 alkyl group, and
n represents 0 or 1.

Embodiment 40

The compound of the Embodiment 36, wherein
X$^1$ represents a hydrogen atom, a C1-C6 alkyl group optionally having one or more halogen atoms, NR$^b$R$^c$, C(O)OR$^d$, a halogen atom, or a phenyl group, wherein R$^b$, R$^c$, and R$^d$ represent a hydrogen atom or a C1-C6 alkyl group,
R$^1$ represents a C1-C5 perfluoroalkyl group or S(O)$_r$R$^5$,
R$^2$ represents a C1-C3 alkyl group, and
n represents 0 or 1.

Embodiment 41

A present compound represented by formula (I-F):

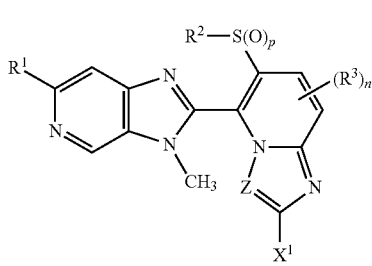

(I-F)

wherein the symbols are the same as defined above.

Embodiment 42

The compound of the Embodiment 41, wherein
X$^1$ represents a hydrogen atom, a halogen atom, a methyl group, CF$_3$, or an amino group,
R$^1$ represents a C1-C5 perfluoroalkyl group,
R$^2$ represents a C1-C3 alkyl group, and
n represents 0.

Embodiment 43

A present compound represented by formula (I-G):

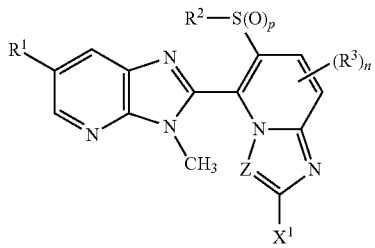

(I-G)

wherein the symbols are the same as defined above.

Embodiment 44

The compound of the Embodiment 43, wherein
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C3 alkyl group, and
n represents 0 or 1.

Embodiment 45

The compound of the Embodiment 43, wherein
$X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^1$ represents a C1-C5 perfluoroalkyl group or $S(O)_lR^5$,
$R^2$ represents a C1-C3 alkyl group, and
n represents 0 or 1.

Embodiment 46

The compound of the Embodiment 43, wherein
$X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group,
$R^2$ represents a C1-C3 alkyl group, and
n represents 0 or 1.

Embodiment 47

The compound of the Embodiment 43, wherein
$A^1$ represents $NCH_3$,
$A^2$ represents a nitrogen atom,
$A^3$ represents CH,
$X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group,
$R^1$ represents a C1-C5 perfluoroalkyl group or $S(O)_lR^5$,
$R^2$ represents a C1-C3 alkyl group, and
n represents 0 or 1.

Embodiment 48

A present compound represented by formula (I-H):

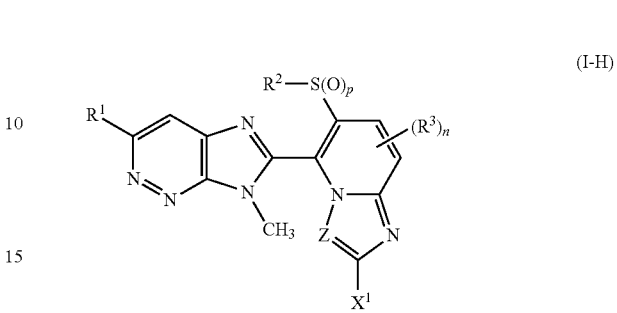

(I-H)

wherein
$X^1$ represents a hydrogen atom, a halogen atom, a methyl group, $CF_3$, or an amino group,
$R^1$ represents a C1-C5 perfluoroalkyl group,
$R^2$ represents a C1-C3 alkyl group,
n represents 0, and
the other symbols are the same as defined above.

Embodiment 49

A present compound, wherein
$A^1$ represents $NCH_3$,
$A^2$ represents CH,
$A^3$ represents CH,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 50

A present compound, wherein
$A^1$ represents $NCH_3$,
$A^2$ represents CH,
$A^3$ represents a nitrogen atom,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 51

A present compound, wherein
$A^1$ represents $NCH_3$,

A² represents a nitrogen atom,
A³ represents CH,
X¹ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
R² represents a C1-C6 alkyl group optionally having one or more halogen atoms, and
n represents 0 or 1.

Embodiment 52

A present compound, wherein
A¹ represents $NCH_3$,
A² represents a nitrogen atom,
A³ represents a nitrogen atom,
X¹ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
R² represents a C1-C6 alkyl group optionally having one or more halogen atoms, and
n represents 0 or 1.

Embodiment 53

A present compound, wherein
A¹ represents $NCH_3$,
A² represents a nitrogen atom,
A³ represents CH,
X¹ represents a hydrogen atom, a halogen atom, a methyl group, $CF_3$, or an amino group,
R¹ represents a C1-C5 perfluoroalkyl group,
R² represents a C1-C3 alkyl group,
R³ represents a halogen atom, and
n represents 0 or 1.

Embodiment 54

A present compound represented by formula (I-I):

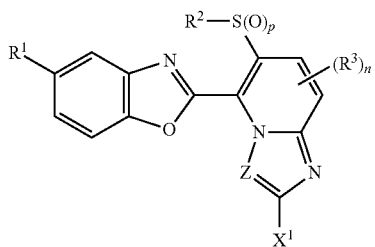

(I-I)

wherein the symbols are the same as defined above.

Embodiment 55

The compound of the Embodiment 54, wherein

X¹ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
R² represents a C1-C3 alkyl group, and
n represents 0 or 1.

Embodiment 56

The compound of the Embodiment 54, wherein
X¹ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
R¹ represents a C1-C5 perfluoroalkyl group or $S(O)_rR^5$,
R² represents a C1-C3 alkyl group, and
n represents 0 or 1.

Embodiment 57

The compound of the Embodiment 54, wherein
X¹ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group,
R² represents a C1-C3 alkyl group, and
n represents 0 or 1.

Embodiment 58

The compound of the Embodiment 54, wherein
X¹ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group,
R¹ represents a C1-C5 perfluoroalkyl group or $S(O)_rR^5$,
R² represents a C1-C3 alkyl group, and
n represents 0 or 1.

Embodiment 59

A present compound represented by formula (I-J):

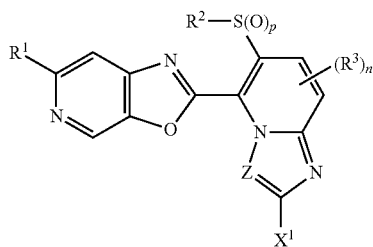

(I-J)

wherein the symbols are the same as defined above.

Embodiment 60

The compound of the Embodiment 59, wherein $X^1$ represents a hydrogen atom, a halogen atom, a methyl group, $CF_3$, or an amino group, $R^1$ represents a C1-C5 perfluoroalkyl group, $R^2$ represents a C1-C3 alkyl group, and n represents 0.

Embodiment 61

A present compound represented by formula (I-K):

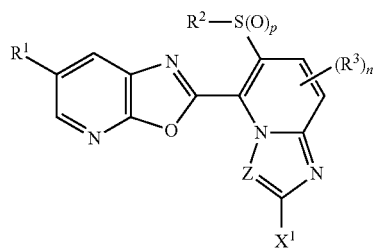

(I-K)

wherein the symbols are the same as defined above.

Embodiment 62

The compound of the Embodiment 61, wherein $X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^2$ represents a C1-C3 alkyl group, and n represents 0 or 1.

Embodiment 63

The compound of the Embodiment 61, wherein $X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^1$ represents a C1-C5 perfluoroalkyl group or $S(O)_rR^5$, $R^2$ represents a C1-C3 alkyl group, and n represents 0 or 1.

Embodiment 64

The compound of the Embodiment 61, wherein $X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group, $R^2$ represents a C1-C3 alkyl group, and n represents 0 or 1.

Embodiment 65

The compound of the Embodiment 61, wherein $X^1$ represents a hydrogen atom, a C1-C6 alkyl group optionally having one or more halogen atoms, $NR^bR^c$, $C(O)OR^d$, a halogen atom, or a phenyl group, wherein $R^b$, $R^c$, and $R^d$ represent a hydrogen atom or a C1-C6 alkyl group, $R^1$ represents a C1-C5 perfluoroalkyl group or $S(O)_rR^5$, $R^2$ represents a C1-C3 alkyl group, and n represents 0 or 1.

Embodiment 66

A present compound represented by formula (I-L):

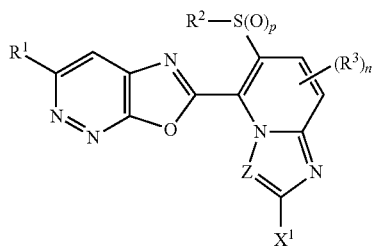

(I-L)

wherein $X^1$ represents a hydrogen atom, a halogen atom, a methyl group, $CF_3$, or an amino group, $R^1$ represents a C1-C5 perfluoroalkyl group, $R^2$ represents a C1-C3 alkyl group, n represents 0, and the other symbols are the same as defined above.

Embodiment 67

A present compound, wherein $A^1$ represents an oxygen atom, $A^2$ represents CH, $A^3$ represents CH, $X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^2$ represents a C1-C6 alkyl group optionally having one or more halogen atoms, and n represents 0 or 1.

Embodiment 68

A present compound, wherein $A^1$ represents an oxygen atom, $A^2$ represents CH, $A^3$ represents a nitrogen atom, $X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group, $R^2$ represents a C1-C6 alkyl group optionally having one or more halogen atoms, and n represents 0 or 1.

Embodiment 69

A present compound, wherein
$A^1$ represents an oxygen atom,
$A^2$ represents a nitrogen atom,
$A^3$ represents CH,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 70

A present compound, wherein
$A^1$ represents an oxygen atom,
$A^2$ represents a nitrogen atom,
$A^3$ represents a nitrogen atom,
$X^1$ represents a hydrogen atom, a C1-C6 alkyl group optionally having one or more halogen atoms, a phenyl group optionally having one or more halogen atoms, a 5 or 6 membered aromatic heterocyclic group optionally having one or more halogen atoms, a C3-C6 cycloalkyl group optionally having one or more halogen atoms, a halogen atom, a cyano group, $OR^a$, $NR^bR^c$, $C(O)OR^d$, or $C(O)NR^eR^f$, wherein $R^a$, $R^b$, $R^c$, $R^d$, $R^e$, and $R^f$ each independently represent a hydrogen atom or a C1-C6 alkyl group,
$R^2$ represents a C1-C6 alkyl group optionally having one or more halogen atoms, and
n represents 0 or 1.

Embodiment 71

A present compound, wherein
$A^1$ represents $NCH_3$ or an oxygen atom,
$A^3$ represents CH,
$R^1$ represents a C1-C5 perfluoroalkyl group or $S(O)_rR^5$,
$R^2$ represents a C1-C6 alkyl group optionally having one or more halogen atoms,
n represents 0 or 1,
$R^3$ represents a halogen atom,
$X^1$ represents a hydrogen atom, a C1-C6 alkyl group optionally having one or more halogen atoms, a halogen atom, $C(O)OR^d$, an amino group, or a phenyl group, and
$R^d$ represents a hydrogen atom or a C1-C6 alkyl group, Embodiment 72

A present compound, wherein
$A^1$ represents $NCH_3$ or an oxygen atom,
$A^2$ represents CH,
$A^3$ represents CH,
$R^1$ represents a C1-C5 perfluoroalkyl group or $S(O)_rR^5$,
$R^2$ represents a C1-C6 alkyl group optionally having one or more halogen atoms,
n represents 0 or 1,
$R^3$ represents a halogen atom,
$X^1$ represents a hydrogen atom, a C1-C6 alkyl group optionally having one or more halogen atoms, a halogen atom, $C(O)OR^d$, an amino group, or a phenyl group, and
$R^d$ represents a hydrogen atom or a C1-C6 alkyl group.

Embodiment 73

A present compound, wherein
$A^1$ represents $NCH_3$ or an oxygen atom,
$A^2$ represents a nitrogen atom,
$A^3$ represents CH,
$R^1$ represents a C1-C5 perfluoroalkyl group or $S(O)_rR^5$,
$R^2$ represents a C1-C6 alkyl group optionally having one or more halogen atoms,
n represents 0 or 1,
$R^3$ represents a halogen atom,
$X^1$ represents a hydrogen atom, a C1-C6 alkyl group optionally having one or more halogen atoms, a halogen atom, $C(O)OR^d$, an amino group, or a phenyl group, and
$R^d$ represents a hydrogen atom or a C1-C6 alkyl group.

Embodiment 74

The compound of the Embodiments 5 to 73, wherein Z represents a nitrogen atom or $CX^2$.

Embodiment 75

The compound of the Embodiments 5 to 73, wherein Z represents a nitrogen atom or CH.

Embodiment 76

The compound of the Embodiments 5 to 73, wherein Z represents a nitrogen atom.

Embodiment 77

The compound of the Embodiments 5 to 73, wherein represents $CX^2$.

Embodiment 78

The compound of the Embodiments 5 to 73, wherein represents $CX^2$, and
$X^2$ represents a hydrogen atom, a C1-C6 alkyl group optionally having one or more halogen atoms, a halogen atom, a nitro group, or $C(O)OR^d$ Embodiment 79

The compound of the Embodiments 5 to 73, wherein Z represents CH.

Next, a process for preparing the present compound is described.

The present compound can be prepared, for example, according to the following processes.

Process 1

A compound represented by formula (Ib) (hereinafter, referred to as "present compound (Ib)") and a compound represented by formula (Ic) (hereinafter, referred to as "present compound (Ic)") may be prepared by reacting a compound represented by formula (Ia) (hereinafter, referred to as "present compound (Ia)") with an oxidizing agent.

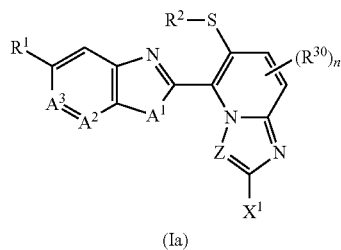 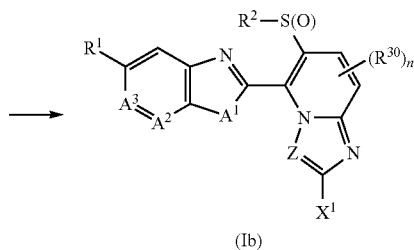 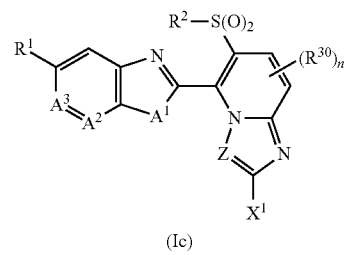

(Ia)　　　(Ib)　　　(Ic)

wherein the symbols are the same as those defined above.

Firstly, a process for preparing the present compound (Ib) from the present compound (Ia) is described.

The reaction is usually carried out in the presence of a solvent.

Examples of the solvent to be used in the reaction include halogenated aliphatic hydrocarbons (hereinafter, collectively referred to as "halogenated aliphatic hydrocarbons") such as dichloromethane and chloroform; nitriles (hereinafter, collectively referred to "nitriles") such as acetonitrile; alcohols (hereinafter, collectively referred to as "alcohols") such as methanol and ethanol; acetic acid; water; and mixed solvents thereof.

Examples of the oxidizing agent to be used in the reaction include sodium periodate, m-chloroperoxybenzoic acid (hereinafter, referred to as "mCPBA"), and hydrogen peroxide.

When hydrogen peroxide is used as the oxidizing agent, sodium carbonate or a catalyst may be added as needed.

Examples of the catalyst to be used in the reaction include tungstic acid and sodium tungstate.

In the reaction, the oxidizing agent is used usually within a range of 1 to 1.2 molar ratio(s), relative to 1 mole of the present compound (Ia).

When hydrogen peroxide is used as the oxidizing agent, sodium carbonate is used usually within a range of 0.01 to 1 molar ratio(s), and the catalyst is used usually within a range of 0.01 to 0.5 molar ratios, relative to 1 mole of the present compound (Ia).

A reaction temperature in the reaction is usually within a range of −20 to 80° C. A reaction period in the reaction is usually within a range of 0.1 to 12 hours.

When the reaction is completed, to the reaction mixture is added water, and the reaction mixture is extracted with an organic solvent. The organic layer is sequentially washed with an aqueous solution of a reducing agent such as sodium sulfite and sodium thiosulfate, and an aqueous solution of a base such as sodium hydrogen carbonate as needed. The resulting organic layer can be dried and concentrated to isolate the present compound (Ib).

Next, a process for preparing the present compound (Ic) from the present compound (Ib) is described.

The reaction is usually carried out in the presence of a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as the oxidizing agent, a base or catalyst may be added as needed.

Examples of the base to be used include sodium carbonate.

Examples of the catalyst to be used include sodium tungstate.

In the reaction, the oxidizing agent is used usually within a range of 1 to 2 molar ratio(s) relative to 1 mole of the present compound (Ib).

When hydrogen peroxide is used as the oxidizing agent, the base is used usually within a range of 0.01 to 1 molar ratio(s), and the catalyst is used usually within a range of 0.01 to 0.5 molar ratios, relative to 1 mole of the present compound (Ib).

A reaction temperature in the reaction is usually within a range of −20 to 120° C. A reaction period in the reaction is usually within a range of 0.1 to 12 hours.

When the reaction is completed, to the reaction mixtures is added water, and the reaction mixture is then extracted with an organic solvent. The organic layer is washed sequentially with an aqueous solution of a reducing agent such as sodium sulfite and sodium thiosulfate, and an aqueous solution of a base such as sodium hydrogen carbonate. The resulting organic layer is dried and concentrated to isolate the present compound (Ic).

Also, the present compound (1c) may be prepared in one step (one-pot) by reacting the present compound (Ia) with an oxidizing agent.

The reaction may be carried out according to the process for preparing the present compound (Ic) from the present compound (Ib) using the oxidizing agent usually in 2 to 3 molar ratios relative to 1 mole of the present compound (Ia).

Process 2

A compound represented by formula (Id) (hereinafter, referred to as "present compound (Id)") may be prepared according to the process described as follows.

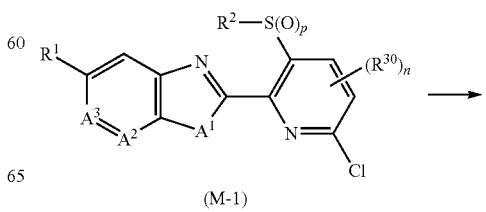

(M-1)

-continued

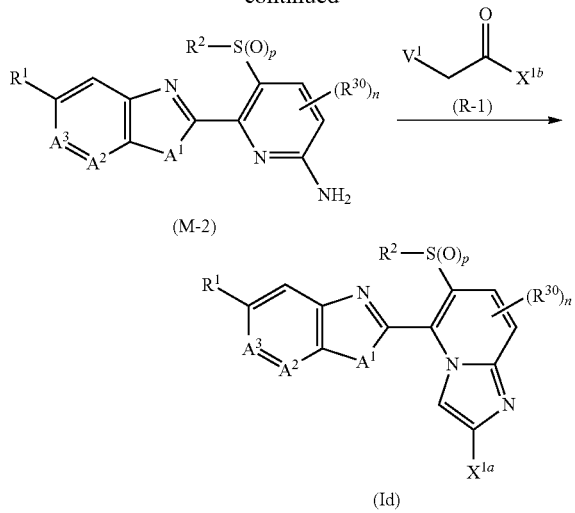

(M-2)

(Id)

wherein $V^1$ represents a chlorine atom, a bromine atom, or an iodine atom, $X^{1a}$ represents a hydrogen atom, a C1-C6 chain hydrocarbon group optionally having one or more substituents selected from group B, a phenyl group optionally having one or more substituents selected from group C, a 5 or 6 membered aromatic heterocyclic group optionally having one or more substituents selected from group C, a C3-C6 alicyclic hydrocarbon group optionally having one or more substituents selected from group C, a hydroxyl group, $C(O)OR^d$, or $C(O)NR^eR^f$, $X^{1b}$ represents a hydrogen atom, a C1-C6 chain hydrocarbon group optionally having one or more substituents selected from group B, a phenyl group optionally having one or more substituents selected from group C, a 5 or 6 membered aromatic heterocyclic group optionally having one or more substituents selected from group C, a C3-C6 alicyclic hydrocarbon group optionally having one or more substituents selected from group C, a C1-C6 alkoxy group, $C(O)OR^d$, or $C(O)NR^eR^f$, and the other symbols are the same as those defined above.

Firstly, a first step for reacting a compound represented by formula (M-1) (hereinafter, referred to as "compound (M-1)") with ammonia to prepare a compound represented by formula (M-2) (hereinafter, referred to as "compound (M-2)") is described.

The reaction is usually carried out in a solvent.

Examples of the solvent to be used in the reaction include ethers (hereinafter, collectively referred to as "ethers") such as tetrahydrofuran (hereinafter, referred to as "THF"), ethyleneglycol dimethyl ether, methyl tert-butyl ether (hereinafter, referred to as "MTBE") and 1,4-dioxane; aromatic hydrocarbons (hereinafter, collectively referred to as "aromatic hydrocarbons") such as toluene and xylene; nitriles; polar aprotic solvents (hereinafter, collectively referred to as "polar aprotic solvents") such as dimethylformamide (hereinafter, referred to as "DMF"), N-methyl pyrrolidone and dimethyl sulfoxide (hereinafter, referred to "DMSO"); water, and mixed solvents thereof.

In the reaction, ammonia is usually used within a range of 1 to 100 molar ratio(s), preferably 1 to 5 molar ratio(s), relative to 1 mole of the compound (M-1).

In the reaction, a base may be added.

Examples of the base to be used in the reaction include alkali metal carbonates (hereinafter, correctively referred to as "alkali metal carbonates") such as sodium carbonate and potassium carbonate; and alkali metal hydrides (hereinafter, collectively referred to as "alkali metal hydrides") such as sodium hydride.

An amount of the base to be used in the reaction is within a range of 1 to 10 mole(s), preferably 1 to 2 mole(s), relative to 1 mole of the compound (M-1).

A reaction temperature in the reaction is usually within a range of −20 to 150° C. A reaction period in the reaction is usually within a range of 0.5 to 24 hours.

When the reaction is completed, to the reaction mixture is added water, and the precipitated solid can be collected by a filtration, and worked up (for example, washing with water and drying) to give the compound (M-2).

The compound (M-1) may be prepared according to a similar method to that described in International Publication No. WO2014/142292, International Publication No. WO2015/000715, or International Publication No. WO2013/018928.

Next, a second step for reacting the compound (M-2) with a compound represented by formula (R-1) (hereinafter, referred to as "compound (R-1)") to prepare the present compound (Id) is described.

The reaction is usually carried out in a solvent.

Examples of the solvent to be used in the reaction include ethers, aromatic hydrocarbons, nitriles, polar aprotic solvents, and mixtures thereof.

In the reaction, the compound (R-1) is usually used within a range of 1 to 10 molar ratio(s), preferably 1.0 to 1.1 molar ratio(s), relative to 1 mole of the compound (M-2).

In the reaction, a base may be added.

Examples of the base to be used in the reaction include alkali metal carbonates and alkali metal hydrides.

In the reaction, the base is usually used within a range of 1 to 10 molar ratio(s), preferably 1 to 2 molar ratio(s), relative to 1 mole of the compound (M-2).

A reaction temperature in the reaction is usually within a range of −20 to 150° C. A reaction period in the reaction is usually within a range of 0.5 to 24 hours.

When the reaction is completed, the reaction mixture is extracted with an organic solvent, and the organic layer can be worked up (for example, drying and concentration) to isolate the compound (Id).

Process 3

A compound represented by formula (Ie) (hereinafter, referred to as "present compound (Ie)") may be prepared according to the process described as follows.

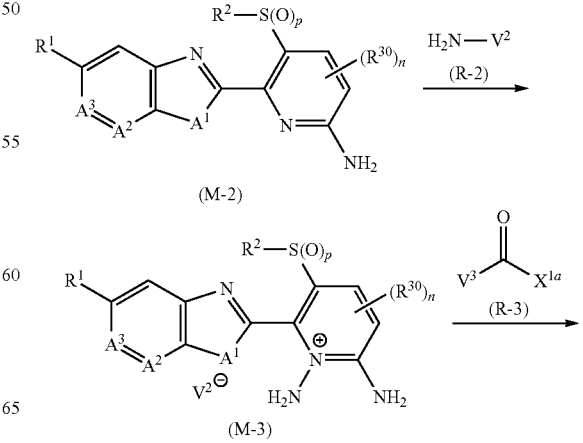

(M-2)

(M-3)

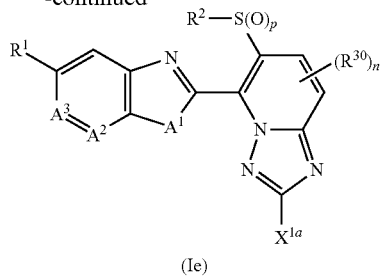

(Ie)

wherein V² represents an optionally substituted benzenesulfonyloxy group, $OS(O)_2OH$, or a chlorine atom, V³ represents a chlorine atom, a hydroxyl group, or $OX^{1a}$, and the other symbols are the same as those defined above.

Firstly, a first step for reacting the compound (M-2) with a compound represented by formula (R-2) (hereinafter, referred to as "compound (R-2)") to prepare a compound represented by formula (M-3) (hereinafter, referred to as "compound (M-3)") is described.

The reaction is usually carried out in a solvent.

Examples of the solvent to be used in the reaction include halogenated aliphatic hydrocarbons, polar aprotic solvents, and mixed solvents thereof.

Examples of the compound (R-2) include chloramine, hydroxylamine-O-sulfonic acid, O-(mesitylsulfony)hydroxylamine (hereinafter, referred to as "MSH"), and O-(2,4-dinitrophenyl)hydroxylamine.

In the reaction, the compound (R-2) is usually used within a range of 1 to 2 molar ratio(s) relative to 1 mole of the compound (M-2).

A reaction temperature in the reaction is usually within a range of −20 to 80° C. A reaction period in the reaction is usually within a range of 0.1 to 12 hours.

When the reaction is completed, to the reaction mixture is added diethylether, and the precipitated solid is then collected by a filtration and the obtained solid can be dried to isolate the compound (M-3).

Next, a second step for reacting the compound (M-3) with a compound represented by formula (R-3) (hereinafter, referred to as "compound (R-3)") in the presence of a base to prepare the present compound (Ie) is described.

The reaction is usually carried out in a solvent.

Examples of the solvent to be used in the reaction include ethers, aromatic hydrocarbons, nitriles, polar aprotic solvents, pyridine, and mixtures thereof.

Examples of the base to be used in the reaction include alkali metal carbonates, alkali metal hydrides, and pyridine.

In the reaction, the compound (R-3) is usually used within a range of 1 to 10 molar ratio(s), preferably 1.0 to 1.1 molar ratio(s), and the base is usually used within a range of 1 to 10 molar ratio(s), preferably 1 to 2 molar ratio(s), relative to 1 mole of the compound (M-3).

A reaction temperature in the reaction is usually within a range of −20 to 200° C. A reaction period in the reaction is usually within a range of 0.5 to 24 hours.

When the reaction is completed, the reaction mixture is extracted with an organic solvent, and the organic layer can be worked up (for example, drying and concentration) to isolate the present compound (Ie).

Process 4

A compound represented by formula (If) (hereinafter, referred to as "present compound (If)") may be prepared according to the process described as follows.

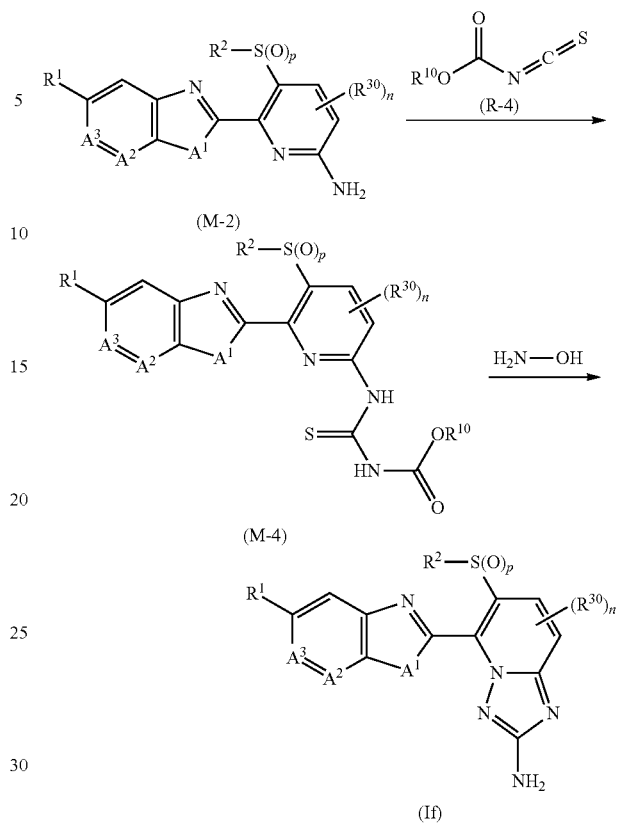

wherein $R^{10}$ represents a C1-C6 alkyl group, and the other symbols are the same as those defined above.

Firstly, a first step for reacting the compound (M-2) with a compound represented by formula (R-4) (hereinafter, referred to as "compound (R-4)") in the presence of a base to prepare a compound represented by formula (M-4) (hereinafter, referred to as "compound (M-4)") is described.

The reaction is usually carried out in a solvent.

Examples of the solvent to be used in the reaction include ethers, aromatic hydrocarbons, nitriles, polar aprotic solvents, and mixtures thereof.

Examples of the base to be used in the reaction include organic bases such as triethylamine and diisopropylethylamine.

In the reaction, the compound (R-4) is usually used within a range of 1 to 5 molar ratio(s), and the base is used within a range of 1 to 3 molar ratio(s), relative to 1 mole of the compound (M-2).

A reaction temperature in the reaction is usually within a range of −20 to 80° C. A reaction period in the reaction is usually within a range of 0.1 to 12 hours.

When the reaction is completed, the reaction mixture is extracted with an organic solvent, and the organic layer can be worked up (for example, drying and concentration) to isolate the compound (M-4).

Next, a second step for reacting the compound (M-4) with hydroxylamine in the presence of a base to prepare the present compound (If) is described.

The reaction is usually carried out in a solvent.

Examples of the solvent to be used in the reaction include ethers, aromatic hydrocarbons, nitriles, polar aprotic solvents, water, and mixtures thereof.

In the reaction, hydroxylamine is usually used within a range of 1 to 10 molar ratio(s), and the base is usually used within a range of 1 to 10 molar ratio(s), relative to 1 mole of the compound (M-4).

A reaction temperature in the reaction is usually within a range of −20 to 200° C. A reaction period in the reaction is usually within a range of 1 to 24 hour(s).

When the reaction is completed, the reaction mixture is extracted with an organic solvent, and the organic layer can be worked up (for example, drying and concentration) to isolate the present compound (If).

Process 5

A compound represented by formula (Ig) (hereinafter, referred to as "present compound (Ig)") may be prepared by reacting the present compound (If) with nitrite and hydrogen halide.

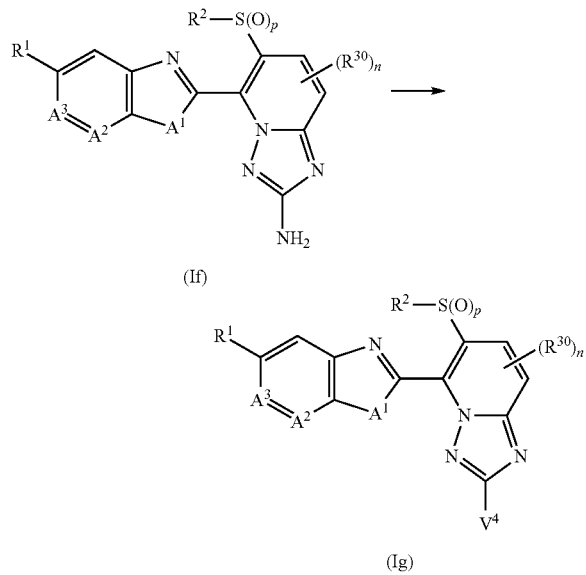

wherein $V^4$ represents a halogen atom, and the other symbols are the same as those defined above.

The reaction is usually carried out in a solvent.

Examples of the solvent to be used in the reaction include ethers, nitriles, water, and mixed solvents thereof.

Examples of the nitrite to be used in the reaction include potassium nitrile and sodium nitrile.

Examples of the hydrogen halide to be used in the reaction include hydrochloric acid, hydrobromic acid, hydroiodic acid, and hydrogen fluoride-pyridine.

In the reaction, copper(II) bromide may be added if $V^4$ is a bromine atom, and copper(II) chloride may be added if $V^4$ is a chlorine atom.

The nitrite is usually used within a range of 1 to 5 molar ratio(s), the hydrogen halide is used within a range of 1 to 10 molar ratio(s), copper(II) bromide is used within a range of 0.1 to 2 molar ratio(s), and copper(II) chloride is used within a range of 0.1 to 2 molar ratio(s) relative to 1 mole of the present compound (If).

A reaction temperature in the reaction is usually within a range of −20 to 80° C. A reaction period in the reaction is usually within a range of 0.1 to 12 hours.

When the reaction is completed, the reaction mixture is extracted with an organic solvent, and the organic layer can be worked up (for example, drying and concentration) to isolate the present compound (Ig).

Process 6

A compound represented by formula (Ii) (hereinafter, referred to as "present compound (Ii)") may be prepared by reacting a compound represented by formula (Ih) (hereinafter, referred to as "present compound (Ih)") with a compound represented by formula (R-5) (hereinafter, referred to as "compound (R-5)") in the presence of a base.

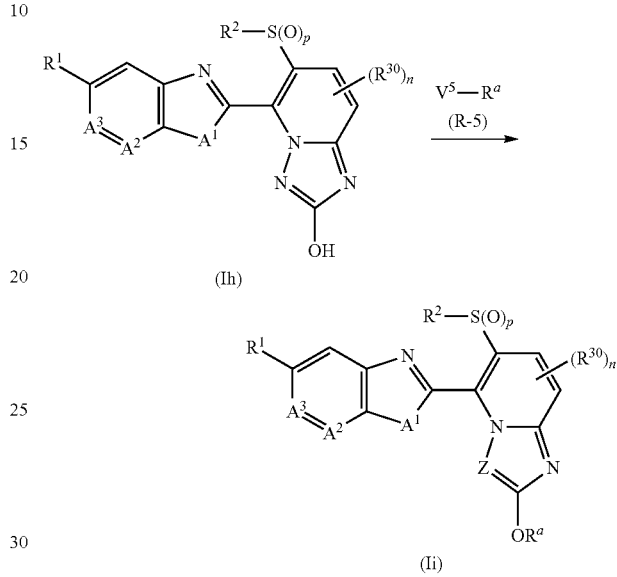

wherein $V^5$ represents a leaving group such as chlorine atom, bromine atom, iodine atom, mesyloxy group and tosyloxy group, and the other symbols are the same as those defined above.

The reaction is usually carried out in a solvent.

Examples of the solvent to be used in the reaction include ethers, aromatic hydrocarbons, nitriles, polar aprotic solvents, and mixtures thereof.

Examples of the solvent to be used in the reaction include alkali metal carbonates, and alkali metal hydrides.

In the reaction, the compound (R-5) is usually used within a range of 1 to 10 molar ratio(s), and the base is used within a range of 1 to 10 molar ratio(s), relative to 1 mole of the present compound (Ih).

A reaction temperature in the reaction is usually within a range of −20 to 150° C. A reaction period in the reaction is usually within a range of 0.5 to 24 hours.

When the reaction is completed, the reaction mixture is extracted with an organic solvent, and the organic layer can be worked up (for example, drying and concentration) to isolate the present compound (Ii).

Process 7

A compound represented by formula (Ik) (hereinafter, referred to as "present compound (Ik)") may be prepared by reacting a compound represented by formula (Ij) (hereinafter, referred to as "present compound (Ij)") with a halogenating agent.

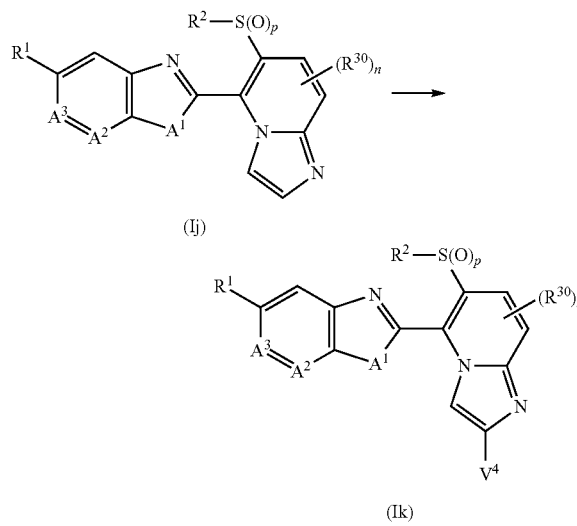

(Ij)

(Ik)

wherein the symbols are the same as those defined above.

The reaction is usually carried out in a solvent.

Examples of the solvent to be used in the reaction include ethers, aromatic hydrocarbons, nitriles, polar aprotic solvents, and mixtures thereof.

Examples of the halogenating agent to be used in the reaction include N-chlorosuccinimide, N-bromosuccinimide, and N-iodosuccinimide.

In the reaction, the halogenating agent is usually used within a range of 1 to 1.2 molar ratio(s) relative to 1 mole of the present compound (Ij).

A reaction temperature in the reaction is usually within a range of 0 to 100° C. A reaction period in the reaction is usually within a range of 0.1 to 24 hours.

When the reaction is completed, the reaction mixture is extracted with an organic solvent, and the organic layer can be worked up (for example, drying and concentration) to isolate the present compound (Ik).

Process 8

A compound represented by formula (IIb) and a compound represented by formula (IIc) may be prepared by reacting a compound represented by formula (IIa) with an oxidizing agent.

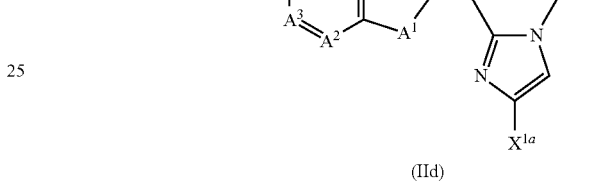

(M-5)

(M-6)

(IId)

wherein the symbols are the same as those defined above.

The reaction is usually carried out according to the process described in Process 2.

A compound represented by formula (M-5) may be prepared according to the process described in International Publication No. WO2014/142292, International Publication No. WO2015/000715, or International Publication No. WO2013/018928.

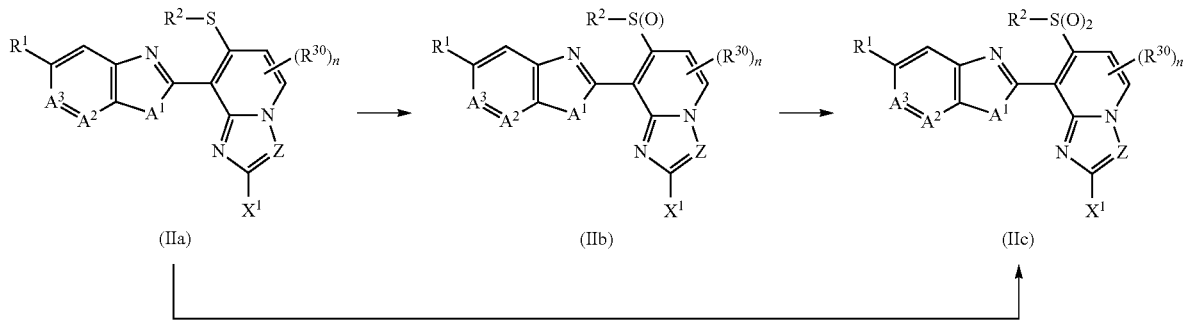

(IIa)  (IIb)  (IIc)

wherein the symbols are the same as those defined above.

The reaction is usually carried out according to the process described in Process 1.

Process 9

A compound represented by formula (IId) may be prepared according to the process described as follows.

Process 10

A compound represented by formula (IIe) may be prepared according to the process described as follows.

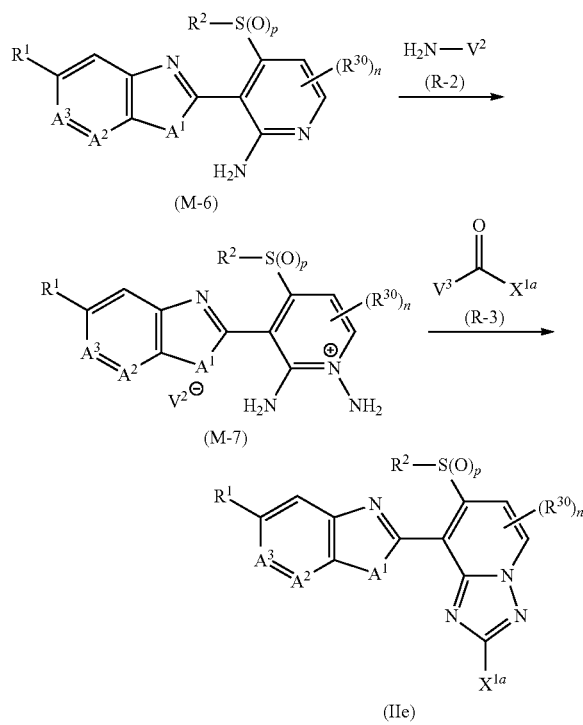

(M-6)

(M-7)

(IIe)

wherein the symbols are the same as those defined above.

The reaction is usually carried out according to the process described in Process 3.

Process 11

A compound represented by formula (IIk) may be prepared by reacting a compound represented by formula (IIj) with a halogenating agent.

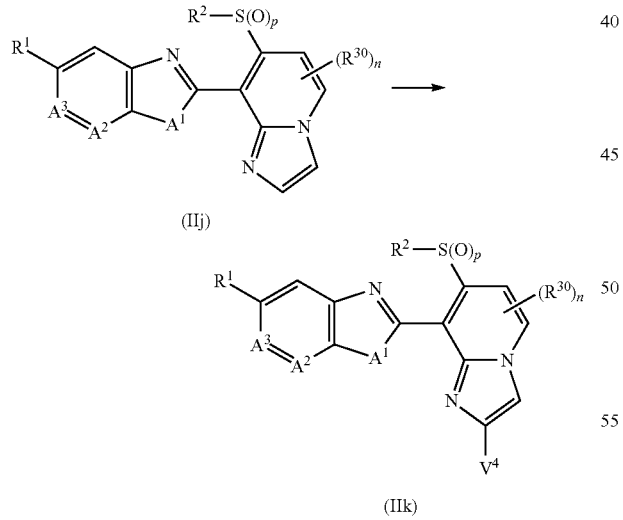

(IIj)

(IIk)

wherein the symbols are the same as those defined above.

The reaction is usually carried out according to the process described in Process 7.

Next, specific examples of the present compound are recited as follows.

A present compound being a compound represented by formula (I-A1):

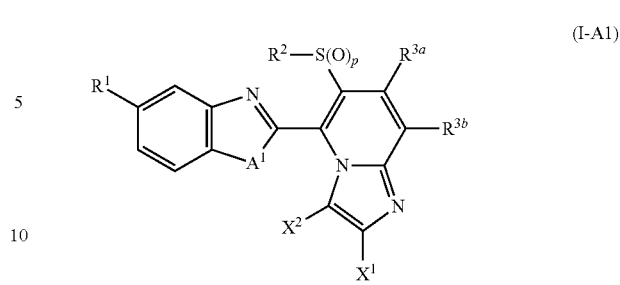

(I-A1)

[wherein the symbols are the same as those defined above]

wherein $R^2$ represents an ethyl group, $R^{3a}$ represents a hydrogen atom, $A^1$ represents $NCH_3$, and $R^1$, p, $X^1$, $X^2$, and $R^{3b}$ represent a combination indicated in any of [Table 1] to [Table 15].

As used herein, Me represents a methyl group, Et represents an ethyl group, Pr represents a propyl group, iPr represents an isopropyl group, and Ph represents a phenyl group.

TABLE 1

| $R^1$ | p | $X^1$ | $X^2$ | $R^{3b}$ |
|---|---|---|---|---|
| $CF_3$ | 0 | H | H | H |
| $CF_3$ | 1 | H | H | H |
| $CF_3$ | 2 | H | H | H |
| $CF_3$ | 2 | H | H | $CF_3$ |
| $CF_3$ | 2 | H | H | Me |
| $CF_3$ | 2 | H | H | Br |
| $CF_3$ | 2 | H | H | Cl |
| $CF_3$ | 2 | Br | H | H |
| $CF_3$ | 2 | H | Br | H |
| $CF_3$ | 2 | Br | Br | H |
| $CF_3$ | 2 | Br | H | $CF_3$ |
| $CF_3$ | 2 | H | Br | $CF_3$ |
| $CF_3$ | 2 | Br | Br | $CF_3$ |
| $CF_3$ | 2 | Cl | H | H |
| $CF_3$ | 2 | H | Cl | H |
| $CF_3$ | 2 | Cl | Cl | H |
| $CF_3$ | 2 | Cl | H | $CF_3$ |
| $CF_3$ | 2 | H | Cl | $CF_3$ |
| $CF_3$ | 2 | Cl | Cl | $CF_3$ |
| $CF_3$ | 2 | Me | H | H |
| $CF_3$ | 2 | $CH_3$ | H | $CF_3$ |
| $CF_3$ | 2 | Et | H | H |
| $CF_3$ | 2 | Pr | H | H |
| $CF_3$ | 2 | iPr | H | H |
| $CF_3$ | 2 | OH | H | H |
| $CF_3$ | 2 | OH | H | $CF_3$ |
| $CF_3$ | 2 | OMe | H | H |
| $CF_3$ | 2 | $CF_3$ | H | H |
| $CF_3$ | 2 | $CF_3$ | H | $CF_3$ |
| $CF_3$ | 2 | $NH_2$ | H | H |
| $CF_3$ | 2 | $NH_2$ | H | $CF_3$ |
| $CF_3$ | 2 | COOH | H | H |
| $CF_3$ | 2 | COOMe | H | H |
| $CF_3$ | 2 | CONHMe | H | H |
| $CF_3$ | 2 | Ph | H | H |

TABLE 2

| $R^1$ | p | $X^1$ | $X^2$ | $R^{3b}$ |
|---|---|---|---|---|
| $CF_3$ | 2 | 4-pyridyl | H | H |

TABLE 2-continued

| R¹ | p | X¹ | X² | R³ᵇ |
|---|---|---|---|---|
| CF₃ | 2 | pyridin-3-yl | H | H |
| CF₃ | 2 | pyridin-2-yl | H | H |
| CF₃ | 2 | pyrrol-1-yl | H | H |
| CF₃ | 2 | cyclopropyl | H | H |
| CF₃ | 2 | cyclopentyl | H | H |
| CF₃ | 2 | Cl | NO₂ | H |
| CF₃ | 2 | CN | NO₂ | H |
| CF₃ | 2 | H | COOH | H |
| CF₃ | 2 | H | COOMe | H |
| CF₃ | 2 | H | NO₂ | H |
| CF₃ | 2 | H | NH₂ | H |
| CF₃ | 2 | H | Me | H |
| CF₃ | 2 | H | Et | H |

TABLE 3

| R¹ | p | X¹ | X² | R³ᵇ |
|---|---|---|---|---|
| C₂F₅ | 0 | H | H | H |
| C₂F₅ | 1 | H | H | H |
| C₂F₅ | 2 | H | H | H |
| C₂F₅ | 2 | H | H | CF₃ |
| C₂F₅ | 2 | H | H | Me |
| C₂F₅ | 2 | H | H | Br |
| C₂F₅ | 2 | H | H | Cl |
| C₂F₅ | 2 | Br | H | H |
| C₂F₅ | 2 | H | Br | H |
| C₂F₅ | 2 | Br | Br | H |
| C₂F₅ | 2 | Br | H | CF₃ |
| C₂F₅ | 2 | H | Br | CF₃ |
| C₂F₅ | 2 | Br | Br | CF₃ |
| C₂F₅ | 2 | Cl | H | H |
| C₂F₅ | 2 | H | Cl | H |
| C₂F₅ | 2 | Cl | Cl | H |
| C₂F₅ | 2 | Cl | H | CF₃ |
| C₂F₅ | 2 | H | Cl | CF₃ |
| C₂F₅ | 2 | Cl | Cl | CF₃ |
| C₂F₅ | 2 | Me | H | H |
| C₂F₅ | 2 | Me | H | CF₃ |
| C₂F₅ | 2 | Et | H | H |
| C₂F₅ | 2 | nPr | H | H |
| C₂F₅ | 2 | iPr | H | H |
| C₂F₅ | 2 | OH | H | H |
| C₂F₅ | 2 | OH | H | CF₃ |
| C₂F₅ | 2 | OMe | H | H |
| C₂F₅ | 2 | CF₃ | H | H |
| C₂F₅ | 2 | CF₃ | H | CF₃ |
| C₂F₅ | 2 | NH₂ | H | H |
| C₂F₅ | 2 | NH₂ | H | CF₃ |
| C₂F₅ | 2 | COOH | H | H |
| C₂F₅ | 2 | COOMe | H | H |
| C₂F₅ | 2 | CONHMe | H | H |
| C₂F₅ | 2 | Ph | H | H |

TABLE 4

| R¹ | p | X¹ | X² | R³ᵇ |
|---|---|---|---|---|
| C₂F₅ | 2 | pyridin-4-yl | H | H |
| C₂F₅ | 2 | pyridin-3-yl | H | H |
| C₂F₅ | 2 | pyridin-2-yl | H | H |
| C₂F₅ | 2 | pyrrol-1-yl | H | H |
| C₂F₅ | 2 | cyclopropyl | H | H |
| C₂F₅ | 2 | cyclopentyl | H | H |
| C₂F₅ | 2 | Cl | NO₂ | H |
| C₂F₅ | 2 | CN | NO₂ | H |
| C₂F₅ | 2 | H | COOH | H |
| C₂F₅ | 2 | H | COOMe | H |
| C₂F₅ | 2 | H | NO₂ | H |
| C₂F₅ | 2 | H | NH₂ | H |
| C₂F₅ | 2 | H | Me | H |
| C₂F₅ | 2 | H | Et | H |

TABLE 5

| R¹ | p | X¹ | X² | R³ᵇ |
|---|---|---|---|---|
| SCF₃ | 0 | H | H | H |
| SCF₃ | 1 | H | H | H |
| SCF₃ | 2 | H | H | H |
| SCF₃ | 2 | H | H | CF₃ |
| SCF₃ | 2 | H | H | Me |
| SCF₃ | 2 | H | H | Br |
| SCF₃ | 2 | H | H | Cl |
| SCF₃ | 2 | Br | H | H |
| SCF₃ | 2 | H | Br | H |
| SCF₃ | 2 | Br | Br | H |
| SCF₃ | 2 | Br | H | CF₃ |
| SCF₃ | 2 | H | Br | CF₃ |
| SCF₃ | 2 | Br | Br | CF₃ |
| SCF₃ | 2 | Cl | H | H |
| SCF₃ | 2 | H | Cl | H |
| SCF₃ | 2 | Cl | Cl | H |
| SCF₃ | 2 | Cl | H | CF₃ |
| SCF₃ | 2 | H | Cl | CF₃ |
| SCF₃ | 2 | Cl | Cl | CF₃ |
| SCF₃ | 2 | Me | H | H |
| SCF₃ | 2 | Me | H | CF₃ |
| SCF₃ | 2 | Et | H | H |
| SCF₃ | 2 | Pr | H | H |
| SCF₃ | 2 | iPr | H | H |
| SCF₃ | 2 | OH | H | H |
| SCF₃ | 2 | OH | H | CF₃ |
| SCF₃ | 2 | OMe | H | H |
| SCF₃ | 2 | CF₃ | H | H |
| SCF₃ | 2 | CF₃ | H | CF₃ |
| SCF₃ | 2 | NH₂ | H | H |
| SCF₃ | 2 | NH₂ | H | CF₃ |
| SCF₃ | 2 | COOH | H | H |
| SCF₃ | 2 | COOMe | H | H |

TABLE 5-continued

| R¹ | p | X¹ | X² | R³ᵇ |
|---|---|---|---|---|
| SCF₃ | 2 | CONHMe | H | H |
| SCF₃ | 2 | Ph | H | H |

TABLE 6

| R¹ | p | X¹ | X² | R³ᵇ |
|---|---|---|---|---|
| SCF₃ | 2 | 4-pyridyl | H | H |
| SCF₃ | 2 | 3-pyridyl | H | H |
| SCF₃ | 2 | 2-pyridyl | H | H |
| SCF₃ | 2 | N-pyrrolyl | H | H |
| SCF₃ | 2 | cyclopropyl | H | H |
| SCF₃ | 2 | cyclopentyl | H | H |
| SCF₃ | 2 | Cl | NO₂ | H |
| SCF₃ | 2 | CN | NO₂ | H |
| SCF₃ | 2 | H | COOH | H |
| SCF₃ | 2 | H | COOMe | H |
| SCF₃ | 2 | H | NO₂ | H |
| SCF₃ | 2 | H | NH₂ | H |
| SCF₃ | 2 | H | Me | H |
| SCF₃ | 2 | H | Et | H |

TABLE 7

| R¹ | p | X¹ | X² | R³ᵇ |
|---|---|---|---|---|
| S(O)CF₃ | 0 | H | H | H |
| S(O)CF₃ | 1 | H | H | H |
| S(O)CF₃ | 2 | H | H | H |
| S(O)CF₃ | 2 | H | H | CF₃ |
| S(O)CF₃ | 2 | H | H | Me |
| S(O)CF₃ | 2 | H | H | Br |
| S(O)CF₃ | 2 | H | H | Cl |
| S(O)CF₃ | 2 | Br | H | H |
| S(O)CF₃ | 2 | H | Br | H |
| S(O)CF₃ | 2 | Br | Br | H |
| S(O)CF₃ | 2 | Br | H | CF₃ |
| S(O)CF₃ | 2 | H | Br | CF₃ |
| S(O)CF₃ | 2 | Br | Br | CF₃ |
| S(O)CF₃ | 2 | Cl | H | H |
| S(O)CF₃ | 2 | H | Cl | H |
| S(O)CF₃ | 2 | Cl | Cl | H |
| S(O)CF₃ | 2 | Cl | H | CF₃ |
| S(O)CF₃ | 2 | H | Cl | CF₃ |
| S(O)CF₃ | 2 | Cl | Cl | CF₃ |
| S(O)CF₃ | 2 | Me | H | H |
| S(O)CF₃ | 2 | Me | H | CF₃ |
| S(O)CF₃ | 2 | Et | H | H |
| S(O)CF₃ | 2 | Pr | H | H |
| S(O)CF₃ | 2 | iPr | H | H |
| S(O)CF₃ | 2 | OH | H | H |

TABLE 7-continued

| R¹ | p | X¹ | X² | R³ᵇ |
|---|---|---|---|---|
| S(O)CF₃ | 2 | OH | H | CF₃ |
| S(O)CF₃ | 2 | OMe | H | H |
| S(O)CF₃ | 2 | CF₃ | H | H |
| S(O)CF₃ | 2 | CF₃ | H | CF₃ |
| S(O)CF₃ | 2 | NH₂ | H | H |
| S(O)CF₃ | 2 | NH₂ | H | CF₃ |
| S(O)CF₃ | 2 | COOH | H | H |
| S(O)CF₃ | 2 | COOMe | H | H |
| S(O)CF₃ | 2 | CONHMe | H | H |
| S(O)CF₃ | 2 | Ph | H | H |

TABLE 8

| R¹ | p | X¹ | X² | R³ᵇ |
|---|---|---|---|---|
| S(O)CF₃ | 2 | 4-pyridyl | H | H |
| S(O)CF₃ | 2 | 3-pyridyl | H | H |
| S(O)CF₃ | 2 | 2-pyridyl | H | H |
| S(O)CF₃ | 2 | N-pyrrolyl | H | H |
| S(O)CF₃ | 2 | cyclopropyl | H | H |
| S(O)CF₃ | 2 | cyclopentyl | H | H |
| S(O)CF₃ | 2 | Cl | NO₂ | H |
| S(O)CF₃ | 2 | CN | NO₂ | H |
| S(O)CF₃ | 2 | H | COOH | H |
| S(O)CF₃ | 2 | H | COOMe | H |
| S(O)CF₃ | 2 | H | NO₂ | H |
| S(O)CF₃ | 2 | H | NH₂ | H |
| S(O)CF₃ | 2 | H | Me | H |
| S(O)CF₃ | 2 | H | Et | H |

TABLE 9

| R¹ | p | X¹ | X² | R³ᵇ |
|---|---|---|---|---|
| S(O)₂CF₃ | 0 | H | H | H |
| S(O)₂CF₃ | 1 | H | H | H |
| S(O)₂CF₃ | 2 | H | H | H |
| S(O)₂CF₃ | 2 | H | H | CF₃ |
| S(O)₂CF₃ | 2 | H | H | Me |
| S(O)₂CF₃ | 2 | H | H | Br |
| S(O)₂CF₃ | 2 | H | H | Cl |
| S(O)₂CF₃ | 2 | Br | H | H |
| S(O)₂CF₃ | 2 | H | Br | H |
| S(O)₂CF₃ | 2 | Br | Br | H |
| S(O)₂CF₃ | 2 | Br | H | CF₃ |
| S(O)₂CF₃ | 2 | H | Br | CF₃ |
| S(O)₂CF₃ | 2 | Br | Br | CF₃ |
| S(O)₂CF₃ | 2 | Cl | H | H |
| S(O)₂CF₃ | 2 | H | Cl | H |
| S(O)₂CF₃ | 2 | Cl | Cl | H |
| S(O)₂CF₃ | 2 | Cl | H | CF₃ |

TABLE 9-continued

| R¹ | p | X¹ | X² | R³ᵇ |
|---|---|---|---|---|
| S(O)₂CF₃ | 2 | H | Cl | CF₃ |
| S(O)₂CF₃ | 2 | Cl | Cl | CF₃ |
| S(O)₂CF₃ | 2 | Me | H | H |
| S(O)₂CF₃ | 2 | Me | H | CF₃ |
| S(O)₂CF₃ | 2 | Et | H | H |
| S(O)₂CF₃ | 2 | Pr | H | H |
| S(O)₂CF₃ | 2 | iPr | H | H |
| S(O)₂CF₃ | 2 | OH | H | H |
| S(O)₂CF₃ | 2 | OH | H | CF₃ |
| S(O)₂CF₃ | 2 | OMe | H | H |
| S(O)₂CF₃ | 2 | CF₃ | H | H |
| S(O)₂CF₃ | 2 | CF₃ | H | CF₃ |
| S(O)₂CF₃ | 2 | NH₂ | H | H |
| S(O)₂CF₃ | 2 | NH₂ | H | CF₃ |
| S(O)₂CF₃ | 2 | COOH | H | H |
| S(O)₂CF₃ | 2 | COOMe | H | H |
| S(O)₂CF₃ | 2 | CONHMe | H | H |
| S(O)₂CF₃ | 2 | Ph | H | H |

TABLE 10

| R¹ | p | X¹ | X² | R³ᵇ |
|---|---|---|---|---|
| S(O)₂CF₃ | 2 | 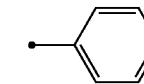 | H | H |
| S(O)₂CF₃ | 2 | 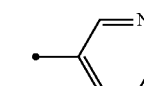 | H | H |
| S(O)₂CF₃ | 2 | 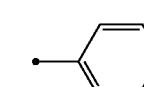 | H | H |
| S(O)₂CF₃ | 2 | 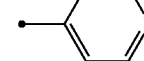 | H | H |
| S(O)₂CF₃ | 2 | 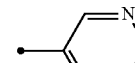 | H | H |
| S(O)₂CF₃ | 2 | 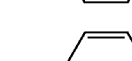 | H | H |
| S(O)₂CF₃ | 2 | Cl | NO₂ | H |
| S(O)₂CF₃ | 2 | CN | NO₂ | H |
| S(O)₂CF₃ | 2 | H | COOH | H |
| S(O)₂CF₃ | 2 | H | COOMe | H |
| S(O)₂CF₃ | 2 | H | NO₂ | H |
| S(O)₂CF₃ | 2 | H | NH₂ | H |
| S(O)₂CF₃ | 2 | H | Me | H |
| S(O)₂CF₃ | 2 | H | Et | H |

TABLE 11

| R¹ | p | X¹ | X² | R³ᵇ |
|---|---|---|---|---|
| OS(O)₂CF₃ | 0 | H | H | H |
| OS(O)₂CF₃ | 1 | H | H | H |
| OS(O)₂CF₃ | 2 | H | H | H |
| OS(O)₂CF₃ | 2 | H | H | CF₃ |
| OS(O)₂CF₃ | 2 | H | H | Me |
| OS(O)₂CF₃ | 2 | H | H | Br |
| OS(O)₂CF₃ | 2 | H | H | Cl |
| OS(O)₂CF₃ | 2 | Br | H | H |
| OS(O)₂CF₃ | 2 | H | Br | H |

TABLE 11-continued

| R¹ | p | X¹ | X² | R³ᵇ |
|---|---|---|---|---|
| OS(O)₂CF₃ | 2 | Br | Br | H |
| OS(O)₂CF₃ | 2 | Br | H | CF₃ |
| OS(O)₂CF₃ | 2 | H | Br | CF₃ |
| OS(O)₂CF₃ | 2 | Br | Br | CF₃ |
| OS(O)₂CF₃ | 2 | Cl | H | H |
| OS(O)₂CF₃ | 2 | H | Cl | H |
| OS(O)₂CF₃ | 2 | Cl | Cl | H |
| OS(O)₂CF₃ | 2 | Cl | H | CF₃ |
| OS(O)₂CF₃ | 2 | H | Cl | CF₃ |
| OS(O)₂CF₃ | 2 | Cl | Cl | CF₃ |
| OS(O)₂CF₃ | 2 | Me | H | H |
| OS(O)₂CF₃ | 2 | Me | H | CF₃ |
| OS(O)₂CF₃ | 2 | Et | H | H |
| OS(O)₂CF₃ | 2 | Pr | H | H |
| OS(O)₂CF₃ | 2 | iPr | H | H |
| OS(O)₂CF₃ | 2 | OH | H | H |
| OS(O)₂CF₃ | 2 | OH | H | CF₃ |
| OS(O)₂CF₃ | 2 | OMe | H | H |
| OS(O)₂CF₃ | 2 | CF₃ | H | H |
| OS(O)₂CF₃ | 2 | CF₃ | H | CF₃ |
| OS(O)₂CF₃ | 2 | NH₂ | H | H |
| OS(O)₂CF₃ | 2 | NH₂ | H | CF₃ |
| OS(O)₂CF₃ | 2 | COOH | H | H |
| OS(O)₂CF₃ | 2 | COOMe | H | H |
| OS(O)₂CF₃ | 2 | CONHMe | H | H |
| OS(O)₂CF₃ | 2 | Ph | H | H |

TABLE 12

| R¹ | p | X¹ | X² | R³ᵇ |
|---|---|---|---|---|
| OS(O)₂CF₃ | 2 | 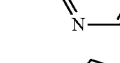 | H | H |
| OS(O)₂CF₃ | 2 |  | H | H |
| OS(O)₂CF₃ | 2 | 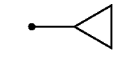 | H | H |
| OS(O)₂CF₃ | 2 |  | H | H |
| OS(O)₂CF₃ | 2 |  | H | H |
| OS(O)₂CF₃ | 2 |  | H | H |
| OS(O)₂CF₃ | 2 | Cl | NO₂ | H |
| OS(O)₂CF₃ | 2 | CN | NO₂ | H |
| OS(O)₂CF₃ | 2 | H | COOH | H |
| OS(O)₂CF₃ | 2 | H | COOMe | H |
| OS(O)₂CF₃ | 2 | H | NO₂ | H |
| OS(O)₂CF₃ | 2 | H | NH₂ | H |
| OS(O)₂CF₃ | 2 | H | Me | H |
| OS(O)₂CF₃ | 2 | H | Et | H |

TABLE 13

| R¹ | p | X¹ | X² | R³ᵇ |
|---|---|---|---|---|
| CF₃ | 2 | H | H | OMe |
| CF₃ | 2 | H | H | OEt |
| CF₃ | 2 | H | H | O—i-Pr |
| CF₃ | 2 | H | H | NHMe |
| CF₃ | 2 | H | H | N(Me)₂ |
| CF₃ | 2 | H | H | cyclopropyl |
| CF₃ | 2 | H | H | 1-cyanocyclopropyl |
| CF₃ | 2 | H | H | 2-fluorophenyl |
| CF₃ | 2 | H | H | 3-fluorophenyl |
| CF₃ | 2 | H | H | 4-fluorophenyl |
| CF₃ | 2 | H | H | 5-fluoropyridin-2-yl |
| CF₃ | 2 | H | H | 4-cyanophenyl |
| CF₃ | 2 | H | H | 4-chloro-1H-pyrazol-1-yl |
| CF₃ | 2 | H | H | 3-(trifluoromethyl)-1H-1,2,4-triazol-1-yl |
| C₂F₅ | 2 | H | H | OMe |
| C₂F₅ | 2 | H | H | OEt |
| C₂F₅ | 2 | H | H | O—i-Pr |
| C₂F₅ | 2 | H | H | NHMe |
| C₂F₅ | 2 | H | H | N(Me)₂ |
| C₂F₅ | 2 | H | H | cyclopropyl |
| C₂F₅ | 2 | H | H | 1-cyanocyclopropyl |

TABLE 14

| R¹ | p | X¹ | X² | R³ᵇ |
|---|---|---|---|---|
| SCF₃ | 2 | H | H | OMe |
| SCF₃ | 2 | H | H | OEt |
| SCF₃ | 2 | H | H | O—i-Pr |
| SCF₃ | 2 | H | H | NHMe |
| SCF₃ | 2 | H | H | N(Me)₂ |
| SCF₃ | 2 | H | H | cyclopropyl |
| SCF₃ | 2 | H | H | 1-cyanocyclopropyl |
| SCF₃ | 2 | H | H | 2-fluorophenyl |
| SCF₃ | 2 | H | H | 3-fluorophenyl |
| SCF₃ | 2 | H | H | 4-fluorophenyl |
| SCF₃ | 2 | H | H | 5-fluoropyridin-2-yl |
| SCF₃ | 2 | H | H | 4-cyanophenyl |
| SCF₃ | 2 | H | H | 4-chloro-1H-pyrazol-1-yl |
| SCF₃ | 2 | H | H | 3-(trifluoromethyl)-1H-1,2,4-triazol-1-yl |
| S(O)CF₃ | 2 | H | H | OMe |
| S(O)CF₃ | 2 | H | H | OEt |
| S(O)CF₃ | 2 | H | H | O—i-Pr |
| S(O)CF₃ | 2 | H | H | NHMe |
| S(O)CF₃ | 2 | H | H | N(Me)₂ |
| S(O)CF₃ | 2 | H | H | cyclopropyl |
| S(O)CF₃ | 2 | H | H | 1-cyanocyclopropyl |

TABLE 15

| R¹ | p | X¹ | X² | R³ᵇ |
|---|---|---|---|---|
| S(O)₂CF₃ | 2 | H | H | OMe |
| S(O)₂CF₃ | 2 | H | H | OEt |
| S(O)₂CF₃ | 2 | H | H | O—i-Pr |
| S(O)₂CF₃ | 2 | H | H | NHMe |
| S(O)₂CF₃ | 2 | H | H | N(Me)₂ |

TABLE 15-continued

| R¹ | p | X¹ | X² | R³ᵇ |
|---|---|---|---|---|
| S(O)₂CF₃ | 2 | H | H | cyclopropyl |
| S(O)₂CF₃ | 2 | H | H | 1-cyanocyclopropyl |
| S(O)₂CF₃ | 2 | H | H | 2-fluorophenyl |
| S(O)₂CF₃ | 2 | H | H | 3-fluorophenyl |
| S(O)₂CF₃ | 2 | H | H | 4-fluorophenyl |
| S(O)₂CF₃ | 2 | H | H | 5-fluoropyridin-2-yl |
| S(O)₂CF₃ | 2 | H | H | 4-cyanophenyl |
| S(O)₂CF₃ | 2 | H | H | 4-chloro-1H-pyrazol-1-yl |
| S(O)₂CF₃ | 2 | H | H | 3-(trifluoromethyl)-1H-1,2,4-triazol-1-yl |
| OS(O)₂CF₃ | 2 | H | H | OMe |
| OS(O)₂CF₃ | 2 | H | H | OEt |
| OS(O)₂CF₃ | 2 | H | H | O—i-Pr |
| OS(O)₂CF₃ | 2 | H | H | NHMe |
| OS(O)₂CF₃ | 2 | H | H | N(Me)₂ |
| OS(O)₂CF₃ | 2 | H | H | cyclopropyl |
| OS(O)₂CF₃ | 2 | H | H | 1-cyanocyclopropyl |

A present compound being a compound represented by formula (I-A1), wherein R² represents an ethyl group, R³ᵃ represents a hydrogen atom, A¹ represents an oxygen atom, and R¹, p, X¹, X², and R³ᵇ represent a combination indicated in any of [Table 1] to [Table 15].

A present compound being a compound represented by formula (I-A1), wherein R² represents an ethyl group, R³ᵃ represents a hydrogen atom, A¹ represents a sulfur atom, and R¹, p, X¹, X², and R³ᵇ represent a combination indicated in any of [Table 1] to [Table 15].

A present compound being a compound represented by formula (I-A2):

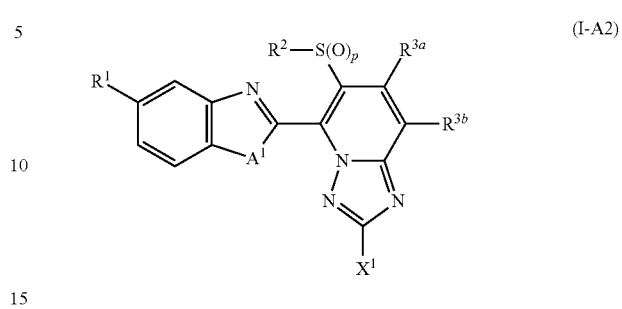

(I-A2)

[wherein the symbols are the same as those defined above]
wherein R² represents an ethyl group, R³ᵃ represents a hydrogen atom, A¹ represents NCH₃, and R¹, p, X¹, and R³ᵇ represent a combination indicated in any of [Table 16] to [Table 30].

TABLE 16

| R¹ | p | X¹ | R³ᵇ |
|---|---|---|---|
| CF₃ | 0 | H | H |
| CF₃ | 1 | H | H |
| CF₃ | 2 | H | H |
| CF₃ | 0 | H | CF₃ |
| CF₃ | 1 | H | CF₃ |
| CF₃ | 2 | H | CF₃ |
| CF₃ | 0 | NH₂ | H |
| CF₃ | 1 | NH₂ | H |
| CF₃ | 2 | NH₂ | H |
| CF₃ | 2 | CF₃ | H |
| CF₃ | 2 | Me | H |
| CF₃ | 2 | Et | H |
| CF₃ | 2 | Pr | H |
| CF₃ | 2 | iPr | H |
| CF₃ | 2 | OH | H |
| CF₃ | 2 | OMe | H |
| CF₃ | 2 | Br | H |
| CF₃ | 2 | Cl | H |
| CF₃ | 2 | COOH | H |
| CF₃ | 2 | COOMe | H |
| CF₃ | 2 | CONHMe | H |
| CF₃ | 2 | Ph | H |

TABLE 17

| R¹ | p | X¹ | R³ᵇ |
|---|---|---|---|
| CF₃ | 2 | pyridin-4-yl | H |
| CF₃ | 2 | pyridin-3-yl | H |
| CF₃ | 2 | pyridin-2-yl | H |
| CF₃ | 2 | 1H-pyrrol-1-yl | H |
| CF₃ | 2 | cyclopropyl | H |

TABLE 17-continued

| R¹ | p | X¹ | R³ᵇ |
|---|---|---|---|
| CF₃ | 2 | cyclopentyl | H |

TABLE 18

| R¹ | p | X¹ | R³ᵇ |
|---|---|---|---|
| C₂F₅ | 0 | H | H |
| C₂F₅ | 1 | H | H |
| C₂F₅ | 2 | H | H |
| C₂F₅ | 0 | H | CF₃ |
| C₂F₅ | 1 | H | CF₃ |
| C₂F₅ | 2 | H | CF₃ |
| C₂F₅ | 0 | NH₂ | H |
| C₂F₅ | 1 | NH₂ | H |
| C₂F₅ | 2 | NH₂ | H |
| C₂F₅ | 2 | CF₃ | H |
| C₂F₅ | 2 | Me | H |
| C₂F₅ | 2 | Et | H |
| C₂F₅ | 2 | Pr | H |
| C₂F₅ | 2 | iPr | H |
| C₂F₅ | 2 | OH | H |
| C₂F₅ | 2 | OMe | H |
| C₂F₅ | 2 | Br | H |
| C₂F₅ | 2 | Cl | H |
| C₂F₅ | 2 | COOH | H |
| C₂F₅ | 2 | COOMe | H |
| C₂F₅ | 2 | CONHMe | H |
| C₂F₅ | 2 | Ph | H |

TABLE 19

| R¹ | p | X¹ | R³ᵇ |
|---|---|---|---|
| C₂F₅ | 2 | 4-pyridyl | H |
| C₂F₅ | 2 | 3-pyridyl | H |
| C₂F₅ | 2 | 2-pyridyl | H |
| C₂F₅ | 2 | N-pyrrolyl | H |
| C₂F₅ | 2 | cyclopropyl | H |
| C₂F₅ | 2 | cyclopentyl | H |

TABLE 20

| R¹ | p | X¹ | R³ᵇ |
|---|---|---|---|
| SCF₃ | 0 | H | H |
| SCF₃ | 1 | H | H |
| SCF₃ | 2 | H | H |

TABLE 20-continued

| R¹ | p | X¹ | R³ᵇ |
|---|---|---|---|
| SCF₃ | 0 | H | CF₃ |
| SCF₃ | 1 | H | CF₃ |
| SCF₃ | 2 | H | CF₃ |
| SCF₃ | 0 | NH₂ | H |
| SCF₃ | 1 | NH₂ | H |
| SCF₃ | 2 | NH₂ | H |
| SCF₃ | 2 | CF₃ | H |
| SCF₃ | 2 | Me | H |
| SCF₃ | 2 | Et | H |
| SCF₃ | 2 | Pr | H |
| SCF₃ | 2 | iPr | H |
| SCF₃ | 2 | OH | H |
| SCF₃ | 2 | OMe | H |
| SCF₃ | 2 | Br | H |
| SCF₃ | 2 | Cl | H |
| SCF₃ | 2 | COOH | H |
| SCF₃ | 2 | COOMe | H |
| SCF₃ | 2 | CONHMe | H |
| SCF₃ | 2 | Ph | H |

TABLE 21

| R¹ | p | X¹ | R³ᵇ |
|---|---|---|---|
| SCF₃ | 2 | 4-pyridyl | H |
| SCF₃ | 2 | 3-pyridyl | H |
| SCF₃ | 2 | 2-pyridyl | H |
| SCF₃ | 2 | N-pyrrolyl | H |
| SCF₃ | 2 | cyclopropyl | H |
| SCF₃ | 2 | cyclopentyl | H |

TABLE 22

| R¹ | p | X¹ | R³ᵇ |
|---|---|---|---|
| S(O)CF₃ | 0 | H | H |
| S(O)CF₃ | 1 | H | H |
| S(O)CF₃ | 2 | H | H |
| S(O)CF₃ | 0 | H | CF₃ |
| S(O)CF₃ | 1 | H | CF₃ |
| S(O)CF₃ | 2 | H | CF₃ |
| S(O)CF₃ | 0 | NH₂ | H |
| S(O)CF₃ | 1 | NH₂ | H |
| S(O)CF₃ | 2 | NH₂ | H |
| S(O)CF₃ | 2 | CF₃ | H |
| S(O)CF₃ | 2 | Me | H |
| S(O)CF₃ | 2 | Et | H |
| S(O)CF₃ | 2 | Pr | H |
| S(O)CF₃ | 2 | iPr | H |
| S(O)CF₃ | 2 | OH | H |
| S(O)CF₃ | 2 | OMe | H |
| S(O)CF₃ | 2 | Br | H |

TABLE 22-continued

| R¹ | p | X¹ | R³ᵇ |
|---|---|---|---|
| S(O)CF₃ | 2 | Cl | H |
| S(O)CF₃ | 2 | COOH | H |
| S(O)CF₃ | 2 | COOMe | H |
| S(O)CF₃ | 2 | CONHMe | H |
| S(O)CF₃ | 2 | Ph | H |

TABLE 23

| R¹ | p | X¹ | R³ᵇ |
|---|---|---|---|
| S(O)CF₃ | 2 | 4-pyridyl | H |
| S(O)CF₃ | 2 | 3-pyridyl | H |
| S(O)CF₃ | 2 | 2-pyridyl | H |
| S(O)CF₃ | 2 | N-pyrrolyl | H |
| S(O)CF₃ | 2 | cyclopropyl | H |
| S(O)CF₃ | 2 | cyclopentyl | H |

TABLE 24

| R¹ | p | X¹ | R³ᵇ |
|---|---|---|---|
| S(O)₂CF₃ | 0 | H | H |
| S(O)₂CF₃ | 1 | H | H |
| S(O)₂CF₃ | 2 | H | H |
| S(O)₂CF₃ | 0 | H | CF₃ |
| S(O)₂CF₃ | 1 | H | CF₃ |
| S(O)₂CF₃ | 2 | H | CF₃ |
| S(O)₂CF₃ | 0 | NH₂ | H |
| S(O)₂CF₃ | 1 | NH₂ | H |
| S(O)₂CF₃ | 2 | NH₂ | H |
| S(O)₂CF₃ | 2 | CF₃ | H |
| S(O)₂CF₃ | 2 | Me | H |
| S(O)₂CF₃ | 2 | Et | H |
| S(O)₂CF₃ | 2 | Pr | H |
| S(O)₂CF₃ | 2 | iPr | H |
| S(O)₂CF₃ | 2 | OH | H |
| S(O)₂CF₃ | 2 | OMe | H |
| S(O)₂CF₃ | 2 | Br | H |
| S(O)₂CF₃ | 2 | Cl | H |
| S(O)₂CF₃ | 2 | COOH | H |
| S(O)₂CF₃ | 2 | COOMe | H |
| S(O)₂CF₃ | 2 | CONHMe | H |
| S(O)₂CF₃ | 2 | Ph | H |

TABLE 25

| R¹ | p | X¹ | R³ᵇ |
|---|---|---|---|
| S(O)₂CF₃ | 2 | 4-pyridyl | H |
| S(O)₂CF₃ | 2 | 3-pyridyl | H |
| S(O)₂CF₃ | 2 | 2-pyridyl | H |
| S(O)₂CF₃ | 2 | N-pyrrolyl | H |
| S(O)₂CF₃ | 2 | cyclopropyl | H |
| S(O)₂CF₃ | 2 | cyclopentyl | H |

TABLE 26

| R¹ | p | X¹ | R³ᵇ |
|---|---|---|---|
| OS(O)₂CF₃ | 0 | H | H |
| OS(O)₂CF₃ | 1 | H | H |
| OS(O)₂CF₃ | 2 | H | H |
| OS(O)₂CF₃ | 0 | H | CF₃ |
| OS(O)₂CF₃ | 1 | H | CF₃ |
| OS(O)₂CF₃ | 2 | H | CF₃ |
| OS(O)₂CF₃ | 0 | NH₂ | H |
| OS(O)₂CF₃ | 1 | NH₂ | H |
| OS(O)₂CF₃ | 2 | NH₂ | H |
| OS(O)₂CF₃ | 2 | CF₃ | H |
| OS(O)₂CF₃ | 2 | Me | H |
| OS(O)₂CF₃ | 2 | Et | H |
| OS(O)₂CF₃ | 2 | Pr | H |
| OS(O)₂CF₃ | 2 | iPr | H |
| OS(O)₂CF₃ | 2 | OH | H |
| OS(O)₂CF₃ | 2 | OMe | H |
| OS(O)₂CF₃ | 2 | Br | H |
| OS(O)₂CF₃ | 2 | Cl | H |
| OS(O)₂CF₃ | 2 | COOH | H |
| OS(O)₂CF₃ | 2 | COOMe | H |
| OS(O)₂CF₃ | 2 | CONHMe | H |
| OS(O)₂CF₃ | 2 | Ph | H |

TABLE 27

| R¹ | p | X¹ | R³ᵇ |
|---|---|---|---|
| OS(O)₂CF₃ | 2 | 4-pyridyl | H |
| OS(O)₂CF₃ | 2 | 3-pyridyl | H |
| OS(O)₂CF₃ | 2 | 2-pyridyl | H |

TABLE 27-continued

| R¹ | p | X¹ | R³ᵇ |
|---|---|---|---|
| OS(O)₂CF₃ | 2 | N-pyrrolyl | H |
| OS(O)₂CF₃ | 2 | cyclopropyl | H |
| OS(O)₂CF₃ | 2 | cyclopentyl | H |

TABLE 28

| R¹ | p | X¹ | R³ᵇ |
|---|---|---|---|
| CF₃ | 2 | H | OMe |
| CF₃ | 2 | H | OEt |
| CF₃ | 2 | H | O—i-Pr |
| CF₃ | 2 | H | NHMe |
| CF₃ | 2 | H | N(Me)₂ |
| CF₃ | 2 | H | cyclopropyl |
| CF₃ | 2 | H | 1-cyanocyclopropyl |
| CF₃ | 2 | H | 2-fluorophenyl |
| CF₃ | 2 | H | 3-fluorophenyl |
| CF₃ | 2 | H | 4-fluorophenyl |
| CF₃ | 2 | H | 5-fluoropyridin-2-yl |
| CF₃ | 2 | H | 4-cyanophenyl |
| CF₃ | 2 | H | 4-chloropyrazol-1-yl |
| CF₃ | 2 | H | 3-(trifluoromethyl)-1,2,4-triazol-1-yl |
| C₂F₅ | 2 | H | OMe |
| C₂F₅ | 2 | H | OEt |
| C₂F₅ | 2 | H | O—i-Pr |
| C₂F₅ | 2 | H | NHMe |

TABLE 28-continued

| R¹ | p | X¹ | R³ᵇ |
|---|---|---|---|
| C₂F₅ | 2 | H | N(Me)₂ |
| C₂F₅ | 2 | H | cyclopropyl |
| C₂F₅ | 2 | H | 1-cyanocyclopropyl |

TABLE 29

| R¹ | p | X¹ | R³ᵇ |
|---|---|---|---|
| SCF₃ | 2 | H | OMe |
| SCF₃ | 2 | H | OEt |
| SCF₃ | 2 | H | O—i-Pr |
| SCF₃ | 2 | H | NHMe |
| SCF₃ | 2 | H | N(Me)₂ |
| SCF₃ | 2 | H | cyclopropyl |
| SCF₃ | 2 | H | 1-cyanocyclopropyl |
| SCF₃ | 2 | H | 2-fluorophenyl |
| SCF₃ | 2 | H | 3-fluorophenyl |
| SCF₃ | 2 | H | 4-fluorophenyl |
| SCF₃ | 2 | H | 5-fluoropyridin-2-yl |
| SCF₃ | 2 | H | 4-cyanophenyl |
| SCF₃ | 2 | H | 4-chloropyrazol-1-yl |
| SCF₃ | 2 | H | 3-(trifluoromethyl)-1,2,4-triazol-1-yl |
| S(O)CF₃ | 2 | H | OMe |
| S(O)CF₃ | 2 | H | OEt |
| S(O)CF₃ | 2 | H | O—i-Pr |
| S(O)CF₃ | 2 | H | NHMe |
| S(O)CF₃ | 2 | H | N(Me)₂ |

TABLE 29-continued

| R¹ | p | X¹ | R³ᵇ |
|---|---|---|---|
| S(O)CF₃ | 2 | H | cyclopropyl |
| S(O)CF₃ | 2 | H | 1-cyanocyclopropyl (NC) |

TABLE 30

| R¹ | p | X¹ | R³ᵇ |
|---|---|---|---|
| S(O)₂CF₃ | 2 | H | OMe |
| S(O)₂CF₃ | 2 | H | OEt |
| S(O)₂CF₃ | 2 | H | O—i-Pr |
| S(O)₂CF₃ | 2 | H | NHMe |
| S(O)₂CF₃ | 2 | H | N(Me)₂ |
| S(O)₂CF₃ | 2 | H | cyclopropyl |
| S(O)₂CF₃ | 2 | H | 1-cyanocyclopropyl (NC) |
| S(O)₂CF₃ | 2 | H | 2-fluorophenyl |
| S(O)₂CF₃ | 2 | H | 3-fluorophenyl |
| S(O)₂CF₃ | 2 | H | 4-fluorophenyl |
| S(O)₂CF₃ | 2 | H | 5-fluoropyridin-2-yl |
| S(O)₂CF₃ | 2 | H | 4-cyanophenyl |
| S(O)₂CF₃ | 2 | H | 4-chloropyrazol-1-yl |
| S(O)₂CF₃ | 2 | H | 3-(trifluoromethyl)-1,2,4-triazol-1-yl |
| OS(O)₂CF₃ | 2 | H | OMe |
| OS(O)₂CF₃ | 2 | H | OEt |
| OS(O)₂CF₃ | 2 | H | O—i-Pr |
| OS(O)₂CF₃ | 2 | H | NHMe |
| OS(O)₂CF₃ | 2 | H | N(Me)₂ |
| OS(O)₂CF₃ | 2 | H | cyclopropyl |

TABLE 30-continued

| R¹ | p | X¹ | R³ᵇ |
|---|---|---|---|
| OS(O)₂CF₃ | 2 | H | 1-cyanocyclopropyl (NC) |

A present compound being a compound represented by formula (I-A2),
wherein R² represents an ethyl group, R³ᵃ represents a hydrogen atom, A¹ represents an oxygen atom, and R¹, p, X¹, and R³ᵇ represent a combination indicated in any of [Table 16] to [Table 30].

A present compound being a compound represented by formula (I-A2),
wherein R² represents an ethyl group, R³ᵃ represents a hydrogen atom, A¹ represents a sulfur atom, and R¹, p, X¹, and R³ᵇ represent a combination indicated in any of [Table 16] to [Table 30].

A present compound being a compound represented by formula (I-B1):

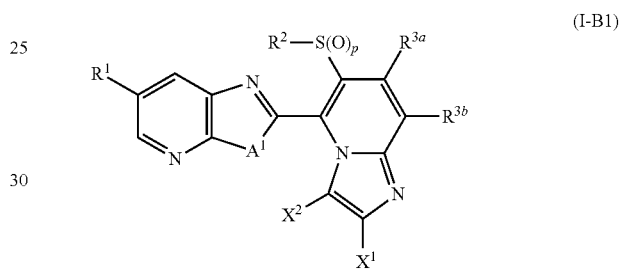

(I-B1)

[wherein the symbols are the same as those defined above]
wherein R² represents an ethyl group, R³ᵃ represents a hydrogen atom, A¹ represents NCH₃, and R¹, p, X¹, X², and R³ᵇ represent a combination indicated in any of [Table 1] to [Table 15].

A present compound being a compound represented by formula (I-B1),
wherein R² represents an ethyl group, R³ᵃ represents a hydrogen atom, A¹ represents an oxygen atom, and R¹, p, X¹, X², and R³ᵇ represent a combination indicated in any of [Table 1] to [Table 15].

A present compound being a compound represented by formula (I-B1),
wherein R² represents an ethyl group, R³ᵃ represents a hydrogen atom, A¹ represents a sulfur atom, and R¹, p, X¹, X², and R³ᵇ represent a combination indicated in any of [Table 1] to [Table 15].

A present compound being a compound represented by formula (I-B2):

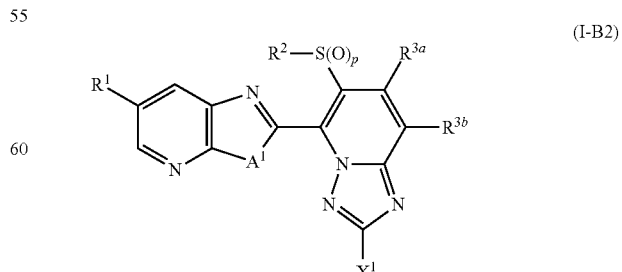

(I-B2)

[wherein the symbols are the same as those defined above]

wherein R² represents an ethyl group, R³ᵃ represents a hydrogen atom, A¹ represents NCH₃, and R¹, p, X¹, and R³ᵇ represent a combination indicated in any of [Table 16] to [Table 30].

A present compound being a compound represented by formula (I-B2),
wherein R² represents an ethyl group, R³ᵃ represents a hydrogen atom, A¹ represents an oxygen atom, and R¹, p, X¹, and R³ᵇ represent a combination indicated in any of [Table 16] to [Table 30].

A present compound being a compound represented by formula (I-B2),
wherein R² represents an ethyl group, R³ᵃ represents a hydrogen atom, A¹ represents a sulfur atom, and R¹, p, X¹, and R³ᵇ represent a combination indicated in any of [Table 16] to [Table 30].

A present compound being a compound represented by formula (I-C1):

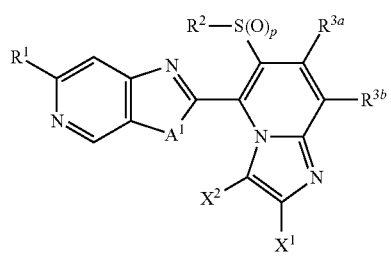

(I-C1)

[wherein the symbols are the same as those defined above]
wherein R² represents an ethyl group, R³ᵃ represents a hydrogen atom, A¹ represents NCH₃, and R¹, p, X¹, X², and R³ᵇ represent a combination indicated in any of [Table 1], [Table 2], [Table 3], [Table 4], [Table 11], [Table 12], [Table 13], [Table 14], and [Table 15].

A present compound being a compound represented by formula (I-C1),
wherein R² represents an ethyl group, R³ᵃ represents a hydrogen atom, A¹ represents an oxygen atom, and R¹, p, X¹, X², and R³ᵇ represent a combination indicated in any of [Table 1], [Table 2], [Table 3], [Table 4], [Table 11], [Table 12], [Table 13], [Table 14], and [Table 15].

A present compound being a compound represented by formula (I-C1),
wherein R² represents an ethyl group, R³ᵃ represents a hydrogen atom, A¹ represents a sulfur atom, and R¹, p, X¹, X², and R³ᵇ represent a combination indicated in any of [Table 1], [Table 2], [Table 3], [Table 4], [Table 11], [Table 12], [Table 13], [Table 14], and [Table 15].

A present compound being a compound represented by formula (I-C2):

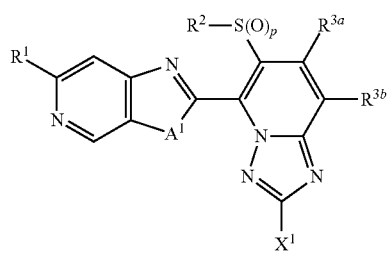

(I-C2)

[wherein the symbols are the same as those defined above]
wherein R² represents an ethyl group, R³ᵃ represents a hydrogen atom, A¹ represents NCH₃, and R¹, p, X¹, and R³ᵇ represent a combination indicated in any of [Table 16], [Table 17], [Table 18], [Table 19], [Table 26], [Table 27], [Table 28], [Table 29], and [Table 30].

A present compound being a compound represented by formula (I-C2),
wherein R² represents an ethyl group, R³ᵃ represents a hydrogen atom, A¹ represents an oxygen atom, and R¹, p, X¹, and R³ᵇ represent a combination indicated in any of [Table 16], [Table 17], [Table 18], [Table 19], [Table 26], [Table 27], [Table 28], [Table 29], and [Table 30].

A present compound being a compound represented by formula (I-C2),
wherein R² represents an ethyl group, R³ᵃ represents a hydrogen atom, A¹ represents a sulfur atom, and R¹, p, X¹, and R³ᵇ represent a combination indicated in any of [Table 16], [Table 17], [Table 18], [Table 19], [Table 26], [Table 27], [Table 28], [Table 29], and [Table 30].

A present compound being a compound represented by formula (I-D1):

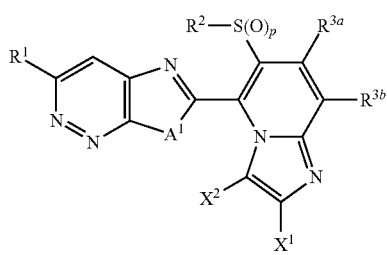

(I-D1)

[wherein the symbols are the same as those defined above]
wherein R² represents an ethyl group, R³ᵃ represents a hydrogen atom, A¹ represents NCH₃, and R¹, p, X¹, X², and R³ᵇ represent a combination indicated in any of [Table 1], [Table 2], [Table 3], [Table 4], [Table 11], [Table 12], [Table 13], [Table 14], and [Table 15].

A present compound being a compound represented by formula (I-D1),
wherein R² represents an ethyl group, R³ᵃ represents a hydrogen atom, A¹ represents an oxygen atom, and R¹, p, X¹, X², and R³ᵇ represent a combination indicated in any of [Table 1], [Table 2], [Table 3], [Table 4], [Table 11], [Table 12], [Table 13], [Table 14], and [Table 15].

A present compound being a compound represented by formula (I-D1),
wherein R² represents an ethyl group, R³ᵃ represents a hydrogen atom, A¹ represents a sulfur atom, and R¹, p, X¹, X², and R³ᵇ represent a combination indicated in any of [Table 1], [Table 2], [Table 3], [Table 4], [Table 11], [Table 12], [Table 13], [Table 14], and [Table 15].

A present compound being a compound represented by formula (I-D2):

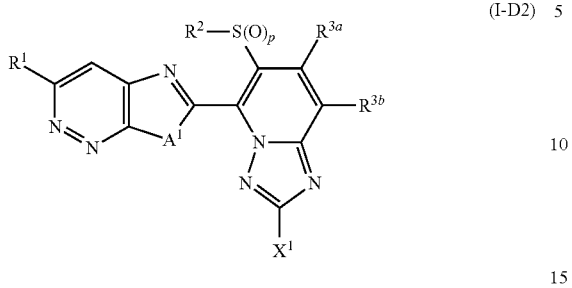
(I-D2)

[wherein the symbols are the same as those defined above]

wherein $R^2$ represents an ethyl group, $R^{3a}$ represents a hydrogen atom, A1 represents $NCH_3$, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (I-D2), wherein $R^2$ represents an ethyl group, $R^{3a}$ represents a hydrogen atom, $A^1$ represents an oxygen atom, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (I-D2), wherein $R^2$ represents an ethyl group, $R^{3a}$ represents a hydrogen atom, $A^1$ represents a sulfur atom, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (III-A1):

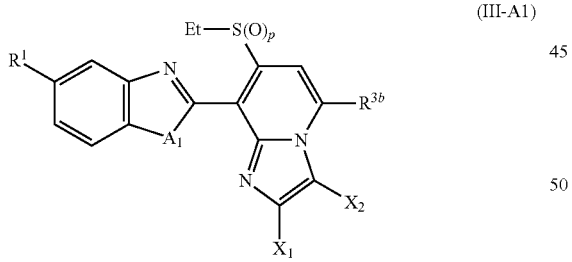
(III-A1)

[wherein the symbols are the same as those defined above]

wherein $A^1$ represents $NCH_3$, and $R^1$, p, $X^1$, $X^2$, and $R^{3b}$ represent a combination indicated in any of [Table 1] to [Table 15].

A present compound being a compound represented by formula (III-A1), wherein $A^1$ represents an oxygen atom, and $R^1$, p, $X^1$, $X^2$, and $R^{3b}$ represent a combination indicated in any of [Table 1] to [Table 15].

A present compound being a compound represented by formula (III-A1),

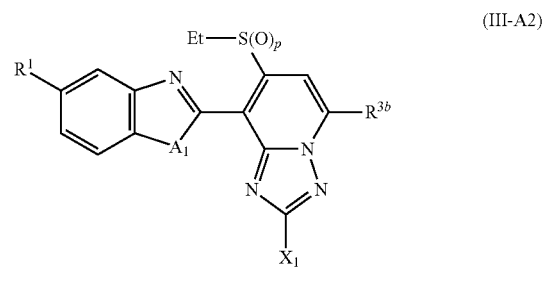
(III-A2)

[wherein the symbols are the same as those defined above]

wherein $A^1$ represents $NCH_3$, and $R^1$, p, $X^1$, and $R^{3b}$ represent a combination indicated in any of [Table 16] to [Table 30].

A present compound being a compound represented by formula (III-A2), wherein $A^1$ represents an oxygen atom, and $R^1$, p, $X^1$, and $R^{3b}$ represent a combination indicated in any of [Table 16] to [Table 30].

A present compound being a compound represented by formula (III-A2), wherein $A^1$ represents a sulfur atom, and $R^1$, p, $X^1$, and $R^{3b}$ represent a combination indicated in any of [Table 16] to [Table 30].

A present compound being a compound represented by formula (III-B1):

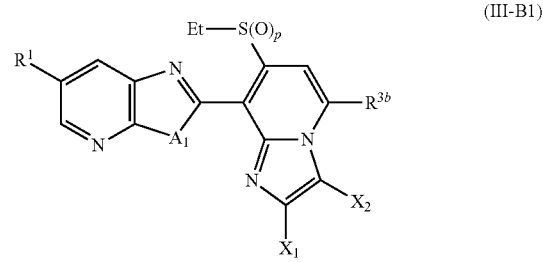
(III-B1)

[wherein the symbols are the same as those defined above]

wherein $A^1$ represents $NCH_3$, and $R^1$, p, $X^1$, $X^2$, and $R^{3b}$ represent a combination indicated in any of [Table 1] to [Table 15].

A present compound being a compound represented by formula (III-B1), wherein $A^1$ represents an oxygen atom, and $R^1$, p, $X^1$, $X^2$, and $R^{3b}$ represent a combination indicated in any of [Table 1] to [Table 15].

A present compound being a compound represented by formula (III-B1), wherein $A^1$ represents a sulfur atom, and $R^1$, p, $X^1$, $X^2$, and $R^b$ represent a combination indicated in any of [Table 1] to [Table 15].

A present compound being a compound represented by formula (III-B2):

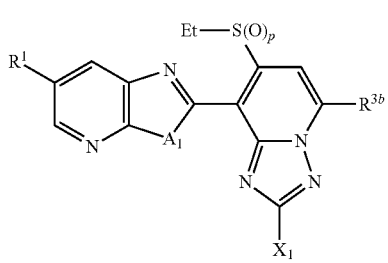

(III-B2)

[wherein the symbols are the same as those defined above]

wherein $A^1$ represents $NCH_3$, and $R^1$, p, $X^1$, and $R^{3b}$ represent a combination indicated in any of [Table 16] to [Table 30].

A present compound being a compound represented by formula (III-B2), wherein $A^1$ represents an oxygen atom, and $R^1$, p, $X^1$, and $R^{3b}$ represent a combination indicated in any of [Table 16] to [Table 30].

A present compound being a compound represented by formula (III-B2), wherein $A^1$ represents a sulfur atom, and $R^1$, p, $X^1$, and $R^{3b}$ represent a combination indicated in any of [Table 16] to [Table 30].

A present compound being a compound represented by formula (III-C1):

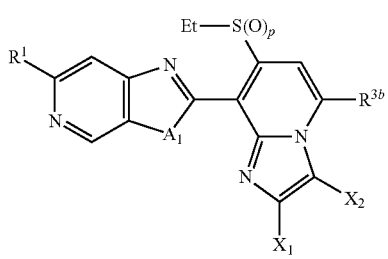

(III-C1)

[wherein the symbols are the same as those defined above]

wherein $A^1$ represents $NCH_3$, and $R^1$, p, $X^1$, $X^2$, and $R^{3b}$ represent a combination indicated in any of [Table 1], [Table 2], [Table 3], [Table 4], [Table 11], [Table 12], [Table 13], [Table 14], and [Table 15].

A present compound being a compound represented by formula (III-C1), wherein $A^1$ represents an oxygen atom, and $R^1$, p, $X^1$, $X^2$, and $R^{3b}$ represent a combination indicated in any of [Table 1], [Table 2], [Table 3], [Table 4], [Table 11], [Table 12], [Table 13], [Table 14], and [Table 15].

A present compound being a compound represented by formula (III-C1), wherein $A^1$ represents a sulfur atom, and $R^1$, p, $X^1$, $X^2$, and $R^{3b}$ represent a combination indicated in any of [Table 1], [Table 2], [Table 3], [Table 4], [Table 11], [Table 12], [Table 13], [Table 14], and [Table 15].

A present compound being a compound represented by formula (III-C2):

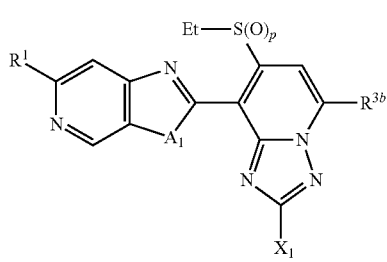

(III-C2)

[wherein the symbols are the same as those defined above]

wherein $A^1$ represents $NCH_3$, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (III-C2), wherein $A^1$ represents an oxygen atom, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (III-C2), wherein $A^1$ represents a sulfur atom, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (III-D1):

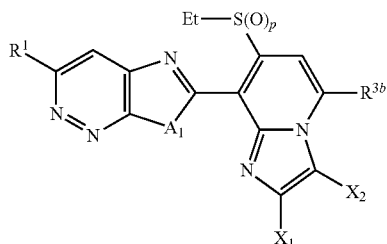

(III-D1)

[wherein the symbols are the same as those defined above]

wherein $A^1$ represents $NCH_3$, and $R^1$, p, $X^1$, $X^2$, and $R^{3b}$ represent a combination indicated in any of [Table 1], [Table 2], [Table 3], [Table 4], [Table 11], [Table 12], [Table 13], [Table 14], and [Table 15].

A present compound being a compound represented by formula (III-D1), wherein $A^1$ represents an oxygen atom, and $R^1$, p, $X^1$, $X^2$, and $R^{3b}$ represent a combination indicated in any of [Table 1], [Table 2], [Table 3], [Table 4], [Table 11], [Table 12], [Table 13], [Table 14], and [Table 15].

A present compound being a compound represented by formula (III-D1), wherein $A^1$ represents a sulfur atom, and $R^1$, p, $X^1$, $X^2$, and $R^{3b}$ represent a combination indicated in any of [Table 1], [Table 2], [Table 3], [Table 4], [Table 11], [Table 12], [Table 13], [Table 14], and [Table 15].

A present compound being a compound represented by formula (III-D2):

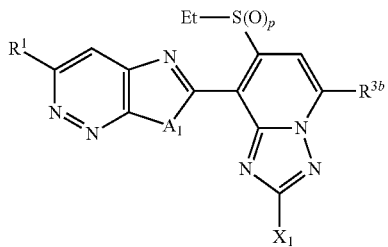

(III-D2)

[wherein the symbols are the same as those defined above]
wherein $A^1$ represents $NCH_3$, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (III-D2),
wherein $A^1$ represents an oxygen atom, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

A present compound being a compound represented by formula (III-D2),
wherein $A^1$ represents a sulfur atom, and $R^1$, p, $X^1$, and $R^{3b}$ represent a combination indicated in any of [Table 16], [Table 17], [Table 18], [Table 19], [Table 26], [Table 27], [Table 28], [Table 29], and [Table 30].

Examples of the harmful arthropod on which the present compound has a control efficacy include harmful insects and harmful mites. Specific examples of such harmful arthropod are recited as follows.

Hemiptera Pests:
Delphacidae (for example, *Laodelphax striatellus, Nilaparvata lugens, Sogatella furcifera,* or *Peregrinus maidis*),
Deltocephalidae (for example, *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolata* (Sugarcane root spittlebug), *Cofana spectra, Nephotettix nigropictus,* or *Recilia dorsalis*),
Aphididae (for example, *Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Aphis glycines Matsumura, Rhopalosiphum maidis, Tetraneura nigriabdominalis, Viteus vitifoliae, Daktulosphaira vitifoliae* (Grape Phylloxera), *Phylloxera devastatrix Pergande* (Pecan phylloxera), *Phylloxera notabilis pergande* (Pecan leaf phylloxera), or *Phylloxera russellae Stoetzel* (Southern pecan leaf phylloxera),
Pentatomidae (for example, *Scotinophara lurida, Scotinophara coarctata* (Malayan rice black bug), *Nezara antennata, Eysarcoris parvus, Halyomorpha mista, Nezara viridula, Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax,* or *Dichelops melacanthus*),
Alydidae (for example, *Riptortus clavetus, Leptocorisa chinensis, Leptocorisa acuta,* or *Leptocorisa* spp.), Miridae (for example, *Trigonotylus caelestialium, Stenotus rubrovittatus, Lygus lineolaris,* or *Blissus leucopterus leucopterus* (Chinchi bug)),
Aleyrodidae (for example, *Trialeurodes vaporariorum, Bemisia tabaci, Dialeurodes citri,* or *Aleurocanthus spiniferus*),
Coccoidea (for example, *Aonidiella aurantii, Comstockaspis perniciosa, Unaspis citri, Ceroplastes rubens, Icerya purchasi, Planococcus kraunhiae, Pseudococcus longispinis, Pseudaulacaspis pentagona,* or *Brevennia rehi*),
Psyllidae (for example, *Diaphorina citri, Psylla pyrisuga, Bactericerca cockerelli*),
Tingidae (for example, *Stephanitis nasi*),
Cimicoidea (for example, *Cimex lectularius*),
*Quesada gigas* (Giant Cicada);
and the others.

Lepidoptera Pests:
Pyralidae (for example, *Chilo suppressalis, Chilo polychrysus* (Darkheaded stem borer), *Tryporyza incertulas, Scirpophaga innotata, Scirpophaga incertulas* (Yellow stem borer), *Sesamia inferens* (Pink borer), *Rupela albinella, Cnaphalocrocis medinalis, Marasmia patnalis, Marasmia exigna, Notarcha derogata, Plodia interpunctella, Ostrinia furnacalis, Hellula undalis, Pediasia teterrellus, Nymphula depunctalis, Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), or *Telchin licus* (Giant Sugarcane borer)),
Noctuidae (for example, *Spodoptera litura, Spodoptera exigua, Pseudaletia separata, Mamestra brassicae, Sesamia inferens, Spodoptera mauritia, Spodoptera frugiperda, Spodoptera exempta, Agrotis ipsilon, Plusia nigrisigna, Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm)),
Pieridae (for example, *Pieris rapae*),
Tortricidae (for example, *Adoxophyes* spp., *Grapholita molesta, Leguminivora glycinivorella, Matsumuraeses azukivora, Adoxophyes orana fasciata, Adoxophyes honmai, Homona magnanima, Archips fuscocupreanus,* or *Cydia pomonella*),
Gracillariidae (for example, *Caloptilia theivora,* or *Phyllonorycter ringoneella*),
Carposinidae (for example, *Carposina niponensis, Ecdytolopha aurantiana* (Citrus fruit borer)),
Lyonetiidae (for example, *Leucoptera coffeela* (Coffee Leaf miner), or *Lyonetia* spp.)),
Lymantriidae (for example, *Lymantria* spp., or *Euproctis* spp.),
Yponomeutidae (for example, *Plutella xylostella*),
Gelechiidae (for example, *Pectinophora gossypiella,* or *Phthorimaea operculella*),
Arctiidae (for example, *Hyphantria cunea*);
and the others.

Thysanoptera Pests:
Thysanopterae (for example, *Frankliniella occidentalis, Thrips parmi, Scirtothrips dorsalis, Thrips tabaci, Frankliniella intonsa, Frankliniella occidentalis, Haplothrips aculeatus, Stenchaetothrips biformis*);
and the others.

Diptera Pests:
House mosquitoes (*Culex* spp.) (for example, *Culex pipiens pallens, Culex tritaeniorhynchus,* or *Culex quinquefasciatus*),

*Aedes* spp. (for example, *Aedes aegypti*, or *Aedes albopictus*),

*Anopheles* spp. (for example, *Anopheles sinensis*),

Chizonomidae,

Muscidae (for example, *Musca domestica*, or *Muscina stabulans*),

Anthomyiidae (for example, *Delia platura*, *Delia antiqua*, or *Tetanops myopaeformis*), Agromyzidae (for example, *Agromyza oryzae*, *Hydrellia griseola*, *Liriomyza sativae*, *Liriomyza trifolii*, or *Chromatomyia horticola*), Chloropidae (for example, *Chlorops oryzae*), Tephritidae (for example, *Dacus cucurbitae*, or *Ceratitis capitata*), Ephydridae (for example, *Hydrellia philippina*, or *Hydrellia sasakii*), Drosophilidae, Phoridae (for example, *Megaselia spiracularis*), Psychodidae (for example, *Clogmia albipunctata*), Sciaridae, Cecidomyiidae (for example, *Mayetiola destructor*, or *Orseolia oryzae*), Diopsidae (for example, *Diopsis macrophthalma*), Tipulidae (for example, *Tipula oleracea* (Common cranefly), or *Tipula paludosa* (European cranefly));

and the others.

Coleoptera Pests:

Chrysomelidae (for example, *Diabrotica virgifera virgifera*, *Diabrotica undecimpunctata howardi*, *Diabrotica barberi*, *Diabrotica virgifera zeae*, *Diabrotica balteata LeConte*, *Diabrotica speciosa*, *Diabrotica speciosa* (Cucurbit Beetle), *Cerotoma trifurcata*, *Oulema melanopus*, *Aulacophora femoralis*, *Phyllotreta striolata*, *Leptinotarsa decemlineata*, *Oulema oryzae*, *Colaspis brunnea*, *Chaetocnema pulicaria*, *Epitrix cucumeris*, *Dicladispa armigera*, *Stenolophus lecontei* (Seedcorn beetle), or *Clivinia impressifrons* (Slender seedcorn beetle)), Scarabaeidae (for example, *Anomala cuprea*, *Anomala rufocuprea*, *Popillia japonica*, *Rhizotrogus majalis* (European Chafer), *Bothynus gibbosus* (Carrot beetle), *Colaspis brunnea* (Grape *Colaspis*), *Myochrous denticollis* (southern Corn leaf beetle), *Holotrichia* spp., or *Phyllophaga* spp. (for example, *Phyllophaga crinita*)), Erirhinidae (for example, *Sitophilus zeamais*, *Echinocnemus squameus*, *Lissorhoptrus oryzophilus*, or *Sphenophorus venatus*), Curculionidae (for example, *Anthonomus grandis*, *Sphenophorus callosus* (Southern Corn Billbug), *Sternechus subsignatus* (Soybean stalk weevil), or *Sphenophorus* spp. (for example, *Sphenophorus levis*)),

*Epilachna* (for example, *Epilachna vigintioctopunctata*),

Scolytidae (for example, *Lyctus brunneus*, or *Tomicus piniperda*),

Bostrichidae,

Ptinidae,

Cerambycidae (for example, *Anoplophora malasiaca*, or *Migdolus fryanus*),

Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis*, *Agriotes ogurae fuscicollis*, or *Melanotus legatus*), Staphylinidae (for example, *Paederus fuscipes*),

*Hypothenemus hampei* (Coffee Barry Borer);

and the others.

Orthoptera Pests:

*Locusta migratoria*, *Gryllotalpa africana*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya japonica*, *Patanga succincta*, *Grylloidea* (for example, *Acheta domesticus*, *Teleogryllus emma*, or *Anabrus simplex* (Mormon cricket));

and the others.

Hymenoptera Pests:

Tenthredinidae (for example, *Athalia rosae*, or *Athalia japonica*),

*Solenopsis* spp.,

*Attini* spp. (for example, *Atta capiguara* (Brown leafcutting ant));

and the others.

Blattariae Pests:

*Blattella germanica*, *Periplaneta fuliginosa*, *Periplaneta americana*, *Periplaneta brunnea*, *Blatta orientalis*, and the others.

Isoptera Pests:

*Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis sjostedti*, *Coptotermes guangzhoensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, or *Cornitermes cumulans*; and the others.

Acarina Pests:

Tetranychidae (for example, *Tetranychus urticae*, *Tetranychus kanzawai*, *Panonychus citri*, *Panonychus ulmi*, *Oligonychus* spp., or *Brevipalpus phoenicis* (Southern Turkey spider mites)), Eriophyidae (for example, *Aculops pelekassi*, *Phyllocoptruta citri*, *Aculops lycopersici*, *Calacazus carinatus*, *Acaphylla theavagrans*, *Eriophyes chibaensis*, or *Aculus schlechtendali*), Tarsonemidae (for example, *Polyphagotarsonemus latus*), Tenuipalpidae (for Example, *Brevipalpus phoenicis*), Tuckerellidae;

Ixodidae (for Example, *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, or *Rhipicephalus sanguineus*), Acaridae (for example, *Tyrophagus putrescentiae*, or *Tyrophagus similis*), Pyroglyphidae (for example, *Dermatophagoides farinae*, or *Dermatophagoides ptrenyssnus*);

and the others.

The agent for controlling harmful arthropods of the present invention comprises the present compound and an inert carrier. The agent for controlling harmful arthropods is usually prepared by mixing the present compound with an inert carrier such as solid carrier, liquid carrier and gaseous carrier, and if necessary, adding surfactants and the other auxiliary agents for formulation to formulate into emulsifiable concentrates, oil solutions, powders, granules, wettable powders, flowables, microcapsules, aerosols, smoking agents, poison baits, resin formulations, shampoo formulations, paste-like formulations, foams, carbon dioxide formulations, tablets, and the others. Such formulations may be processed into mosquito repellent coils, electric mosquito repellent mats, liquid mosquito formulations, smoking agents, fumigants, sheet formulations, spot-on formulations or formulations for oral treatment to use. Also, the agent for controlling harmful arthropods of the present invention may be mixed with other pesticides, miticides, nematicides, fungicides, plant growth regulators, herbicides, and synergists.

The agent for controlling harmful arthropods of the present invention comprises usually 0.01 to 95% by weight of the present compound.

Examples of the solid carrier to be used in the formulation include fine powders or granules such as clays (for example, kaolin clay, diatomaceous earth, bentonite, Fubasami clay, or acid white clay), synthetic hydrous silicon oxides, talcs, ceramics, other inorganic minerals (for example, sericite, quartz, sulfur, active carbon, calcium carbonate, or hydrated silica) and chemical fertilizers (for example, ammonium sulfate, ammonium phosphate, ammonium nitrate, urea, or ammonium chloride); as well as synthetic resins (for example, polyester resins such as polypropylene, polyacrylonitrile, polymethylmethacrylate and polyethylene terephthalate; nylon resins such as nylon-6, nylon-11 and nylon-66; polyamide resins; polyvinyl chloride, polyvinylidene chloride, vinyl chloride-propylene copolymers, and the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether, or 3-methoxy-3-methyl-1-butanol); acid amides (for example, DMF, or dimethylacetamide); halogenated hydrocarbons (for example, dichloromethane, trichloroethane, or carbon tetrachloride); sulfoxides (for example, DMSO); propylene carbonate; and vegetable oils (for example, soybean oil, or cottonseed oil).

Examples of the gaseous carrier include fluorocarbon, butane gas, LPG (liquefied petroleum gas), dimethyl ether, and carbon dioxide gas.

Examples of the surfactant include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agent for formulation include a binder, a dispersant, a colorant, and a stabilizer. Specific examples include casein, gelatin, polysaccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of a base material of the resin formulation include polyvinyl chloride polymers, polyurethane, and the others, and a plasticizer such as phthalate esters (for example, dimethyl phthalate, dioctyl phthalate), adipic acid esters and stearic acid may be added to the base material, if necessary. The resin formulation can be prepared by kneading the present compound in the base material with a conventional kneading machine, and then molding it by injection molding, extrusion molding or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the present compound to a harmful arthropod directly and/or a habitat where the harmful arthropod lives (for example, plant bodies, soil, an interior of a house, and animal bodies). In the method for controlling harmful arthropods of the present invention, the present compound is usually used in the form of a harmful arthropod controlling agent.

When an agent for controlling harmful arthropods of the present invention is used for controlling harmful arthropods in an agricultural field, an application dose as an amount of the present compound is usually within a range from 1 to 10,000 g per 10,000 m$^2$. The emulsifiable concentrate, the wettable powder, or the flowable formulation etc. of the agent for controlling harmful arthropods of the present invention is usually applied by diluting it with water in such a way that a concentration of the active ingredient of the present invention is within a range from 0.01 to 10,000 ppm. The granular formulation, or the powder formulation etc., is usually applied as itself without diluting it.

These formulations and diluents of the formulations with water may be directly sprayed to a harmful arthropod or a plant such as a crop to be protected from a harmful arthropod, or applied to a soil in a cultivated area to control a harmful arthropod that inhabits the soil.

Also, a resin formulation processed into a sheet shape or string shape may be wrapped around a crop, stretched near a crop, spread on a plant foot soil, or the like.

When the agent for controlling harmful arthropods of the present invention is used to control harmful arthropods that live inside a house, the applied dose as an amount of the present compound is usually within a range from 0.01 to 1,000 mg per 1 m$^2$ of an area to be treated, in the case of using it on a planar area. In the case of using it spatially, the applied dose as an amount of the present compound is usually within a range from 0.01 to 500 mg per 1 m$^3$ of the space to be treated. When the agent for controlling harmful arthropods of the present invention is formulated into emulsifiable concentrates, wettable powders, flowables or the others, the formulation is usually applied after diluting it with water in such a way that a concentration of the active ingredient is within a range from 0.1 to 10,000 ppm, and then sparging it. In the case of being formulated into oil solutions, aerosols, smoking agents, poison baits and the others, the formulation is used as itself without diluting it.

When the agent for controlling harmful arthropods of the present invention is used for controlling external parasites of livestock such as cows, horses, pigs, sheep, goats and chickens, and small animals such as dogs, cats, rats and mice, the pest control agent of the present invention can be applied to the animal by a known method in the veterinary field. Specifically, when systemic control is intended, the pest control agent of the present invention is administered to the animal as a tablet, a mixture with feed or a suppository, or by injection (including intramuscular, subcutaneous, intravenous and intraperitoneal injections). On the other hand, when non-systemic control is intended, the pest control agent of the present invention is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound is usually within a range from 0.1 to 1,000 mg per 1 kg of a body weight of the animal.

EXAMPLES

The following examples including Preparation examples, Formulation examples and Test examples serve to describe the present invention in more detail, which should not intend to limit the present invention.

Firstly, for the preparation of the present compound, Preparation examples are shown as follows.

Preparation Example 1-1

A mixture of 2-(6-chloro-3-ethylsulfanylpyridin-2-yl)-5-(trifluoromethyl)benzoxazole 0.40 g, 28% ammonia solution 0.18 mL, and N-methylpyrrolidone 4 mL was stirred at room temperature for 12 hours. To the reaction mixture, water was added, and the mixture was extracted with ethyl acetate. The obtained organic layer was washed with saturated brine, and then dried over anhydrous sodium sulfate and concentrated under reduced pressure. The resulting residue was subjected to a silica gel chromatography to give Intermediate compound 1 shown below 0.30 g.

The compounds prepared according to the method described in the Preparation example 1-1 and its physical properties are shown as follows.

A compound represented by formula (M-2-1):

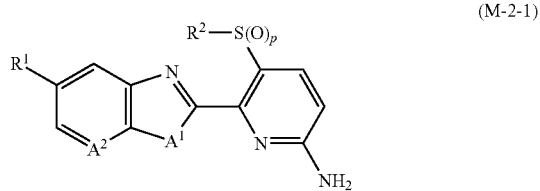

wherein, $A^1$, $A^2$, $R^1$, $R^2$, and p are shown in [Table 31].

TABLE 31

| Intermediate compound | $A^1$ | $A^2$ | $R^1$ | $R^2$ | p |
|---|---|---|---|---|---|
| 1 | O | CH | $CF_3$ | Et | 0 |
| 2 | O | CH | $S(O)CF_3$ | Et | 2 |
| 9 | $NCH_3$ | N | $CF_3$ | Et | 2 |

Intermediate Compound 1
$^1$H-NMR (CDCl$_3$) δ: 8.18 (1H, d, J=8.8 Hz), 8.12 (1H, s), 7.76 (1H, d, J=8.6 Hz), 7.71 (1H, dd, J=8.6, 1.6 Hz), 6.74 (1H, d, J=8.8 Hz), 5.22 (2H, s), 3.82 (2H, q, J=7.4 Hz), 1.40 (3H, t, J=7.5 Hz).
Intermediate Compound 2
$^1$H-NMR (CDCl$_3$) δ: 8.31 (1H, s), 8.19 (1H, d, J=8.8 Hz), 7.90-7.85 (2H, m), 6.76 (1H, d, J=8.8 Hz), 5.23 (2H, s), 3.81 (2H, q, J=7.5 Hz), 1.41 (3H, t, J=7.5 Hz).
Intermediate Compound 9
$^1$H-NMR (CDCl$_3$) δ: 8.73 (1H, dd, J=2.0, 0.7 Hz), 8.28 (1H, dd, J=2.0, 0.5 Hz), 8.15 (1H, d, J=8.8 Hz), 6.73 (1H, d, J=8.8 Hz), 5.15 (2H, s), 3.85 (3H, s), 3.59 (2H, q, J=7.5 Hz), 1.32 (3H, t, J=7.5 Hz).

Preparation Example 1-2

A mixture of Intermediate compound 1 0.40 g, chloroacetaldehyde 0.28 mL, and acetonitrile 5 mL was stirred at 80° C. for one hour. To the reaction mixture, water was added, and the mixture was extracted with ethyl acetate. The obtained organic layer was washed with saturated aqueous sodium hydrogen carbonate solution and saturated brine sequentially, and then dried over anhydrous sodium sulfate and concentrated under reduced pressure. The resulting residue was subjected to a silica gel chromatography to give the present compound 1 shown below 125 mg.

The compounds prepared according to the method described in the Preparation example 1-2 and its physical properties are shown as follows.

A compound represented by formula (IE-1):

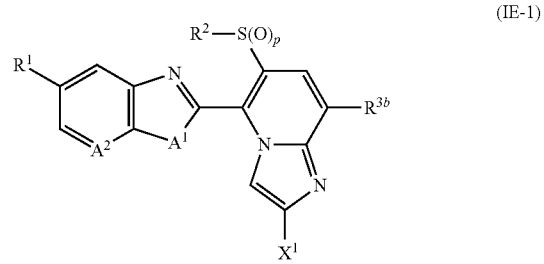

wherein, $A^1$, $A^2$, $R^1$, $R^2$, $R^{3b}$, p, and $X^1$ are shown in [Table 32].

TABLE 32

| Present compound | $A^1$ | $A^2$ | $R^1$ | $R^2$ | $R^{3b}$ | p | $X^1$ |
|---|---|---|---|---|---|---|---|
| 1 | O | CH | $CF_3$ | Et | H | 0 | H |
| 3 | O | CH | $S(O)CF_3$ | Et | H | 2 | H |
| 4 | O | CH | $S(O)CF_3$ | Et | H | 2 | $CF_3$ |
| 5 | O | CH | $S(O)CF_3$ | Et | H | 2 | Me |
| 6 | O | CH | $S(O)CF_3$ | Et | H | 2 | COOEt |
| 8 | O | CH | $3(O)CF_3$ | Et | H | 2 | Ph |
| 12 | $NCH_3$ | N | $CF_3$ | Et | H | 2 | H |
| 13 | $NCH_3$ | N | $CF_3$ | Et | Br | 2 | H |

The Present Compound 1

¹H-NMR (CDCl₃) δ: 8.28 (1H, dd, J=1.1, 0.7 Hz), 8.24 (1H, dd, J=1.7, 0.8 Hz), 7.83-7.79 (3H, m), 7.74 (1H, d, J=1.1 Hz), 7.42 (1H, d, J=9.3 Hz), 3.02 (2H, q, J=7.4 Hz), 1.31 (3H, t, J=7.4 Hz).

The Present Compound 3

¹H-NMR (CDCl₃) δ: 8.43 (1H, s), 8.01 (1H, dd, J=9.6, 0.7 Hz), 7.98 (2H, d, J=1.1 Hz), 7.87 (1H, d, J=1.4 Hz), 7.83 (1H, d, J=9.4 Hz), 7.65 (1H, dd, J=1.4, 0.7 Hz), 3.59 (2H, q, J=7.5 Hz), 1.43 (3H, t, J=7.6 Hz).

The Present Compound 4

¹H-NMR (CDCl₃) δ: 8.45 (1H, s), 8.09 (1H, dd, J=9.6, 0.5 Hz), 8.03-7.96 (4H, m), 3.62 (2H, q, J=7.5 Hz), 1.46 (3H, t, J=7.4 Hz).

The Present Compound 5

¹H-NMR (CDCl₃) δ: 8.42 (1H, s), 7.97 (2H, s), 7.88 (1H, d, J=9.3 Hz), 7.78 (1H, d, J=9.5 Hz), 7.38 (1H, s), 3.56 (2H, q, J=7.4 Hz), 2.48 (3H, s), 1.42 (3H, t, J=7.5 Hz).

The Present Compound 6

¹H-NMR (CDCl₃) δ: 8.45 (1H, s), 8.18 (1H, d, J=0.7 Hz), 8.08 (1H, dd, J=9.5, 0.7 Hz), 8.01 (1H, dd, J=8.7, 1.0 Hz), 7.98 (1H, dd, J=8.6, 0.7 Hz), 7.91 (1H, d, J=9.5 Hz), 4.47 (2H, q, J=7.2 Hz), 3.61 (2H, q, J=7.5 Hz), 1.47-1.40 (6H, m).

The Present Compound 8

¹H-NMR (CDCl₃) δ: 8.45 (1H, s), 7.99 (3H, t, J=4.6 Hz), 7.94 (2H, dd, J=8.0, 1.0 Hz), 7.86 (1H, s), 7.83 (1H, d, J=9.5 Hz), 7.44-7.39 (3H, m), 3.59 (2H, q, J=7.5 Hz), 1.45 (3H, t, J=7.5 Hz).

The Present Compound 12

¹H-NMR (CDCl₃) δ: 1.33 (3H, t, J=7.5 Hz), 3.31 (1H, dq, J=14.4, 7.7 Hz), 3.50 (1H, dq, J=14.4, 7.1 Hz), 3.75 (3H, s), 7.07 (1H, dd, J=1.4, 0.7 Hz), 7.84 (1H, d, J=1.4 Hz), 7.87 (1H, d, J=9.5 Hz), 8.01 (1H, dd, J=9.5, 0.7 Hz), 8.43 (1H, dd, J=1.9, 0.6 Hz), 8.86 (1H, dd, J=2.0, 0.7 Hz).

The Present Compound 13

¹H-NMR (CDCl₃) δ: 8.86 (1H, s), 8.43 (1H, s), 8.15 (1H, s), 7.88 (1H, s), 7.14 (1H, s), 3.75 (3H, s), 3.57-3.46 (1H, m), 3.38-3.27 (1H, m), 1.35 (3H, t, J=7.5 Hz).

A compound represented by formula (IIE-I):

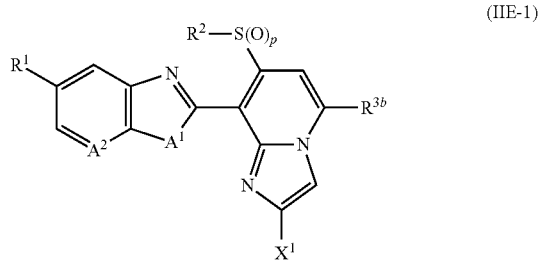

(IIE-1)

wherein, A¹, A², R¹, R², R³ᵇ, p, and X¹ are shown in [Table 33].

TABLE 33

| Present compound | A¹ | A² | R¹ | R² | R³ᵇ | p | X¹ |
|---|---|---|---|---|---|---|---|
| 20 | O | CH | S(O)CF₃ | Et | H | 2 | H |
| 24 | O | CH | SCF₃ | Et | H | 0 | H |

The Present Compound 20

¹H-NMR (CDCl₃) δ: 8.53 (1H, d, J=7.3 Hz), 8.34 (1H, s), 7.94-7.92 (3H, m), 7.88 (1H, dd, J=8.5, 0.9 Hz), 7.57 (1H, d, J=7.1 Hz), 3.64 (2H, q, J=7.4 Hz), 1.41 (3H, t, J=7.4 Hz).

The Present Compound 24

¹H-NMR (CDCl₃) δ: 8.73 (1H, d, J=6.6 Hz), 8.38 (1H, d, J=8.2 Hz), 8.26 (1H, s), 8.11 (1H, s), 8.08 (1H, s), 7.80 (1H, d, J=8.7 Hz), 7.45 (1H, d, J=7.3 Hz), 3.24 (2H, q, J=7.4 Hz), 1.58 (3H, t, J=6.6 Hz).

Preparation Example 2

To a mixture of the present compound 1 123 mg and chloroform 10 mL, mCPBA (70%) 171 mg was added under ice-cooling. The reaction mixture was stirred at room temperature for 2 hours. To the reaction mixture, saturated aqueous sodium hydrogen carbonate solution and sodium thiosulfate were added sequentially, and the mixture was extracted with chloroform. The obtained organic layer was washed with saturated sodium hydrogen carbonate, and then dried over anhydrous sodium sulfate and concentrated under reduced pressure. The resulting residue was subjected to a silica gel chromatography to give the present compound 2 shown below 50 mg.

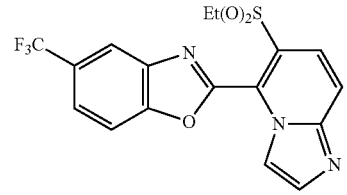

The Present Compound 2

¹H-NMR (CDCl₃) δ: 8.24 (1H, s), 8.00 (1H, d, J=9.7 Hz), 7.87-7.82 (4H, m), 7.60 (1H, s), 3.59 (2H, q, J=7.5 Hz), 1.43 (3H, t, J=7.5 Hz).

The compound prepared according to the method described in the Preparation example 2 and its physical properties are shown as follows.

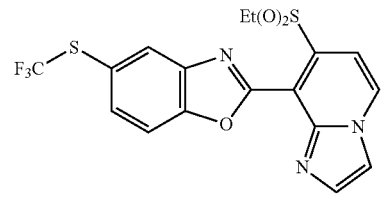

The Present Compound 21

¹H-NMR (CDCl₃) δ: 8.50 (1H, d, J=7.0 Hz), 8.19 (1H, s), 7.94 (1H, d, J=1.1 Hz), 7.91 (1H, d, J=1.1 Hz), 7.76-7.73 (2H, m), 7.56 (1H, d, J=7.2 Hz), 3.65 (2H, q, J=7.5 Hz), 1.40 (3H, t, J=7.5 Hz).

Preparation Example 3

A mixture of the present compound 6 0.30 g, lithium hydroxide monohydrate 36 mg, THF 2 mL, and water 1 mL was stirred at room temperature for 6 hours. To the reaction mixture, 1N hydrochloric acid 10 mL was added, and the mixture was extracted with ethyl acetate. The obtained organic layer was dried over anhydrous sodium sulfate and concentrated under reduced pressure. The resulting residue was subjected to a silica gel chromatography to give the present compound 7 shown below 0.25 g.

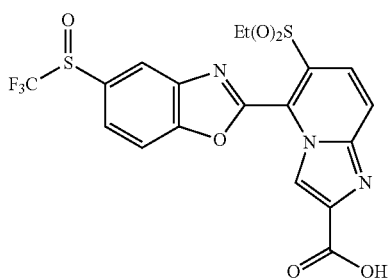

The Present Compound 7

¹H-NMR (DMSO-D₆) δ: 8.82 (1H, s), 8.61 (1H, s), 8.33 (1H, d, J=8.6 Hz), 8.20 (1H, d, J=9.5 Hz), 8.14 (1H, d, J=8.8 Hz), 7.89 (1H, d, J=9.7 Hz), 3.70 (2H, q, J=7.3 Hz), 1.27 (3H, t, J=7.4 Hz).

Preparation Example 4

A mixture of the present compound 3 0.36 g, N-bromosuccinimide 0.15 g, and DMF 2 mL was stirred at room temperature for one hour. To the obtained reaction mixture, water was added to precipitate a solid. The obtained solid was washed with water and dried to give the present compound 9 shown below 0.37 g.

The compounds prepared according to the method described in the Preparation example 4 and its physical properties are shown as follows.

A compound represented by formula (IE-1):

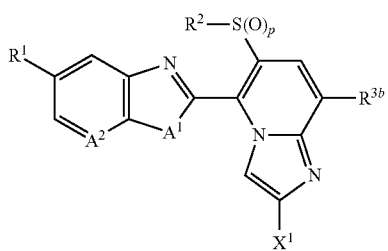

wherein, $A^1$, $A^2$, $R^1$, $R^2$, $R^{3b}$, p, and $X^1$ are shown in [Table 34].

TABLE 34

| Present compound | $A^1$ | $A^2$ | $R^1$ | $R^2$ | $R^{3b}$ | p | $X^1$ |
|---|---|---|---|---|---|---|---|
| 9 | O | CH | S(O)CF₃ | Et | H | 2 | Br |
| 10 | O | CH | S(O)CF₃ | Et | H | 2 | Cl |

The Present Compound 9

¹H-NMR (CDCl₃) δ: 8.42 (1H, s), 8.03 (1H, d, J=9.5 Hz), 7.96 (2H, t, J=9.4 Hz), 7.86 (1H, d, J=9.5 Hz), 7.83 (1H, s), 3.47 (2H, d, J=51.6 Hz), 1.36 (3H, t, J=7.5 Hz).

The Present Compound 10

¹H-NMR (CDCl₃) δ: 8.41 (1H, s), 8.03 (1H, d, J=9.6 Hz), 7.96 (2H, s), 7.85 (1H, d, J=9.4 Hz), 7.78 (1H, s), 3.51-3.43 (2H, br m), 1.36 (3H, t, J=7.4 Hz).

The Present Compound 22 shown as follows

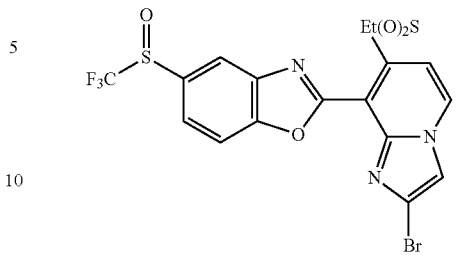

¹H-NMR (CDCl₃) δ: 8.51 (1H, d, J=7.2 Hz), 8.35 (1H, s), 7.94-7.93 (2H, m), 7.89 (1H, d, J=8.6 Hz), 7.71 (1H, d, J=7.2 Hz), 3.65 (2H, q, J=7.4 Hz), 1.41 (3H, t, J=7.5 Hz).

Preparation Example 5

To a mixture of Intermediate compound 3 0.50 g and chloroform 10 mL, MSH 0.27 g was added under ice-cooling, and the reaction mixture was stirred at room temperature for 10 hours. To the reaction mixture, diethylether 40 mL was added to precipitate a solid. The obtained solid was collected by a filtration. The solid was added to a mixture of formic acid 56 μL, 1-ethyl-3-(3-dimethylaminopropyl)carbodiimide hydrochloride 0.23 g, and pyridine 5 mL, and the mixture was then stirred at 120° C. for 13 hours. To the reaction mixture, water and saturated aqueous sodium hydrogen carbonate solution were added, and the reaction mixture was extracted with ethyl acetate. The obtained organic layer was dried over anhydrous sodium sulfate and concentrated under reduced pressure. The resulting residue was subjected to a silica gel chromatography to give the present compound 11 shown below 0.14 g.

The compounds prepared according to the method described in the Preparation example 5 and its physical properties are shown as follows.

A compound represented by formula (IF-1):

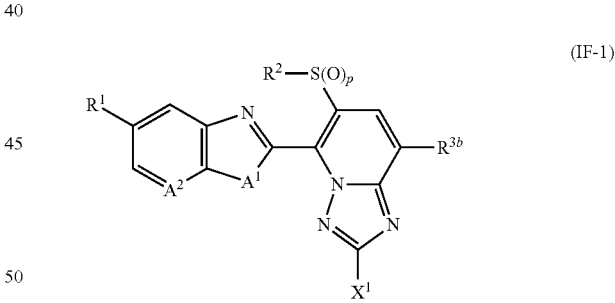

wherein, $A^1$, $A^2$, $R^1$, $R^2$, $R^{3b}$, p, and $X^1$ are shown in [Table 35].

TABLE 35

| Present compound | $A^1$ | $A^2$ | $R^1$ | $R^2$ | $R^{3b}$ | p | $X^1$ |
|---|---|---|---|---|---|---|---|
| 11 | O | CH | S(O)CF₃ | Et | H | 2 | H |
| 15 | NCH₃ | N | CF₃ | Et | H | 2 | CF₃ |
| 23 | O | CH | SCF₃ | Et | H | 2 | CH₃ |

The Present Compound 11

¹H-NMR (CDCl₃) δ: 8.55 (1H, s), 8.42 (1H, s), 8.20 (2H, dd, J=15.1, 9.6 Hz), 7.99-7.95 (2H, m), 3.61 (2H, q, J=7.5 Hz), 1.42 (3H, t, J=7.4 Hz).

The Present Compound 15
¹H-NMR (CDCl₃) δ: 8.88 (1H, d, J=1.4 Hz), 8.42 (1H, d, J=1.8 Hz), 8.38 (1H, d, J=9.5 Hz), 8.24 (1H, d, J=9.5 Hz), 3.79-3.75 (4H, m), 3.51 (1H, td, J=14.6, 7.2 Hz), 1.39 (3H, t, J=7.4 Hz).
The Present Compound 23
¹H-NMR (CDCl₃) δ: 8.24 (1H, s), 8.12 (1H, d, J=9.3 Hz), 7.99 (1H, d, J=9.3 Hz), 7.84 (1H, t, J=5.2 Hz), 7.78 (1H, t, J=4.5 Hz), 3.58 (2H, q, J=7.4 Hz), 2.61 (3H, s), 1.39 (3H, t, J=7.5 Hz).

Preparation Example 6-1

A mixture of Intermediate compound 3 2.11 g, ethoxycarbonyl isothiocyanate 0.46 mL, and dioxane 25 mL was stirred at room temperature for 6.5 hours and then stirred at 50° C. for 6 hours. To the reaction mixture, water was added, and the reaction mixture was extracted with chloroform. The obtained organic layer was washed with saturated aqueous sodium hydrogen carbonate solution and saturated brine sequentially, and then dried over anhydrous sodium sulfate and concentrated under reduced pressure. The resulting residue was subjected to a silica gel chromatography to give Intermediate compound 10 shown below 2.26 g.

The compound prepared according to the method described in the Preparation example 6-1 and its physical properties are shown as follows.
A compound represented by formula (M-4-1):

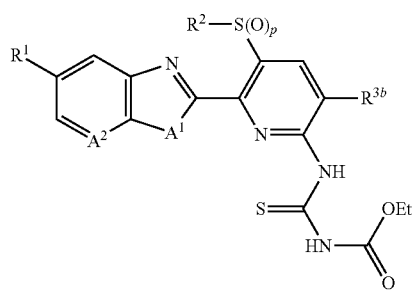

(M-4-1)

wherein, A¹, A², R¹, R², R³ᵇ, and p are shown in [Table 36].

TABLE 36

| Intermediate compound | A¹ | A² | R¹ | R² | R³ᵇ | p |
|---|---|---|---|---|---|---|
| 10 | O | CH | S(O)CF₃ | Et | H | 2 |

Intermediate Compound 10
¹H-NMR (CDCl₃) δ: 9.38 (1H, d, J=8.4 Hz), 8.57 (1H, d, J=8.8 Hz), 8.33 (1H, s), 8.23 (1H, br s), 7.93-7.88 (2H, m), 4.54 (1H, br s), 4.33 (2H, q, J=7.1 Hz), 3.92 (2H, q, J=7.4 Hz), 1.43 (3H, t, J=7.5 Hz), 1.37 (3H, t, J=7.1 Hz).

Preparation Example 6-2

A mixture of Intermediate compound 10 0.70 g, hydroxylamine hydrochloride 0.44 g, diisopropylethylamine 0.66 mL, methanol 5 mL, and ethanol 5 mL was stirred at 60° C. for 1.5 hours. To the reaction mixture, water was added to precipitate a solid. The obtained solid was washed with water and washed with a mixture of MTBE and hexane (MTBE/hexane=1/2) to give the present compound 14 shown below 0.51 g.

The compound prepared according to the method described in the Preparation example 6-2 and its physical properties are shown as follows.
A compound represented by formula (IG-1):

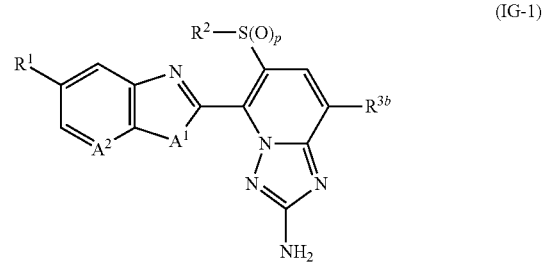

(IG-1)

wherein, A¹, A², R¹, R², R³ᵇ, and p are shown in [Table 37].

TABLE 37

| Present compound | A¹ | A² | R¹ | R² | R³ᵇ | p |
|---|---|---|---|---|---|---|
| 14 | O | CH | S(O)CF₃ | Et | H | 2 |

The Present Compound 14
¹H-NMR (CDCl₃) δ: 8.39 (1H, s), 8.04 (1H, d, J=9.4 Hz), 7.97-7.95 (2H, m), 7.73 (1H, d, J=9.4 Hz), 4.75 (2H, s), 3.53 (2H, q, J=7.5 Hz), 1.39 (3H, t, J=7.4 Hz).

Preparation Example 7

A mixture of the present compound 11 0.40 g, sodium tungstate dihydrate 0.03 g, and 30% hydrogen peroxide solution 1 mL, and acetonitrile 3 mL was stirred at 70° C. for 6 hours. To the reaction mixture, water and sodium thiosulfate were added, and the reaction mixture was extracted with ethyl acetate. The obtained organic layer was washed with saturated aqueous sodium hydrogen carbonate solution and saturated brine sequentially, and then dried over anhydrous sodium sulfate and concentrated under reduced pressure. The resulting residue was subjected to a silica gel chromatography to give the present compound 16 shown below 0.23 g.

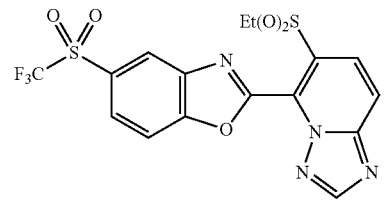

The Present Compound 16
¹H-NMR (CDCl₃) δ: 8.66 (1H, s), 8.54 (1H, s), 8.24-8.22 (3H, m), 8.03 (1H, d, J=8.8 Hz), 3.59 (2H, q, J=7.4 Hz), 1.43 (3H, t, J=7.4 Hz).

Preparation Example 8

A mixture of the present compound 14 0.25 g, sodium nitrite 0.056 g, copper(II) chloride 0.11 g, hydrogen bromide 3 mL, and water 1 mL was stirred at 60° C. for 6 hours. To the reaction mixture, 2M sodium hydroxide solution and water were added, and the reaction mixture was extracted with chloroform. The obtained organic layer was washed with saturated brine, and then dried over anhydrous sodium sulfate and concentrated under reduced pressure. The resulting residue was subjected to a silica gel chromatography to give the present compound 17 shown below 0.17 g.

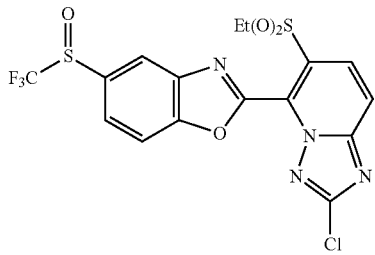

The compounds prepared according to the method described in the Preparation example 8 and its physical properties are shown as follows.
A compound represented by formula (IG-2):

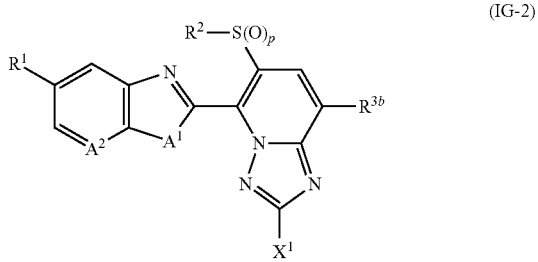

wherein, $A^1$, $A^2$, $R^1$, $R^2$, $R^{3b}$, and p are shown in [Table 38].

TABLE 38

| Present compound | $A^1$ | $A^2$ | $R^1$ | $R^2$ | $R^{3b}$ | p | $X^1$ |
|---|---|---|---|---|---|---|---|
| 17 | O | CH | $S(O)CF_3$ | Et | H | 2 | Cl |
| 18 | O | CH | $S(O)CF_3$ | Et | H | 2 | Br |

The Present Compound 17
$^1$H-NMR (CDCl$_3$) δ: 8.41 (1H, s), 8.25 (1H, d, J=9.4 Hz), 8.07 (1H, d, J=9.4 Hz), 7.98-7.95 (2H, m), 3.62 (2H, q, J=7.5 Hz), 1.42 (3H, t, J=7.5 Hz).
The Present Compound 18
$^1$H-NMR (CDCl$_3$) δ: 8.42 (1H, s), 8.24 (1H, d, J=9.3 Hz), 8.09 (1H, d, J=9.3 Hz), 8.00-7.94 (2H, m), 3.62 (2H, q, J=7.5 Hz), 1.41 (3H, t, J=7.5 Hz).

Preparation Example 9

To a mixture of the present compound 23 0.27 g and chloroform 10 mL, mCPBA (70%) 0.15 g was added under ice-cooling. The reaction mixture was stirred at room temperature for 5 hours. To the obtained reaction mixture, saturated aqueous sodium hydrogen carbonate solution and sodium thiosulfate were added sequentially, and the mixture was extracted with chloroform. The obtained organic layer was washed with saturated aqueous sodium hydrogen carbonate solution, and then dried over anhydrous sodium sulfate and concentrated under reduced pressure. The resulting residue was subjected to a silica gel chromatography to give the present compound 19 shown below 0.29 g.

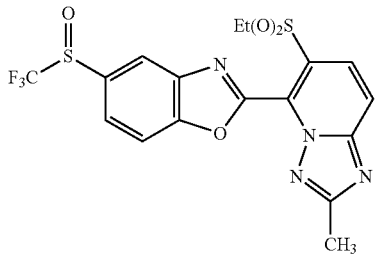

The Present Compound 19
$^1$H-NMR (CDCl$_3$) δ: 8.41 (1H, s), 8.14 (1H, d, J=9.4 Hz), 8.02 (1H, d, J=9.6 Hz), 7.98 (1H, dd, J=8.5, 0.5 Hz), 7.95 (1H, dd, J=8.7, 0.7 Hz), 3.58 (2H, q, J=7.4 Hz), 2.62 (3H, s), 1.40 (3H, t, J=7.4 Hz).

Preparation Example 10

A mixture of the present compound 13 0.25 g, cyclopropylboronic acid 0.13 g, tripotassium phosphate 0.32 g, 1,1'-bis(diphenylphosphino)ferrocene-palladium(II)dichloride-dichloromethane complex 36 mg, water 0.3 mL, and 1,2-dimethoxyethane 3 mL was stirred at 80° C. for 2 hours. To the reaction mixture, water was added, and the reaction mixture was extracted with ethyl acetate. The obtained organic layer was washed with saturated brine, and then dried over anhydrous sodium sulfate and concentrated under reduced pressure. The resulting residue was subjected to a silica gel chromatography to give the present compound 25 shown below.

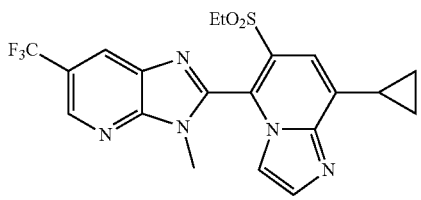

The Present Compound 25
$^1$H-NMR (CDCl3) δ: 8.84 (1H, s), 8.41 (1H, s), 7.79 (1H, d, J=1.4 Hz), 7.31 (1H, s), 7.03 (1H, d, J=1.4 Hz), 3.73 (3H, s), 3.48-3.45 (1H, m), 3.31-3.27 (1H, m), 2.80-2.73 (1H, m), 1.34-1.30 (5H, m), 1.27-1.25 (2H, m).

The compound prepared according to the method described in the Preparation example 10 and its physical properties are shown as follows.

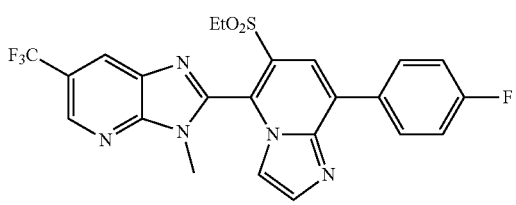

The Present Compound 26
$^1$H-NMR (CDCl3) δ: 8.87 (1H, s), 8.44 (1H, s), 8.16 (2H, dd, J=8.6, 5.4 Hz), 7.95 (1H, s), 7.87 (1H, s), 7.29 (2H, t, J=7.9 Hz), 7.12 (1H, s), 3.80 (3H, s), 3.56-3.53 (1H, m), 3.38-3.32 (1H, m), 1.36 (3H, t, J=7.5 Hz).

Reference Preparation Example 1

A mixture of Intermediate compound 9 4.00 g, N-bromosuccinimide 2.03 g, and chloroform 40 mL was stirred at 70° C. for 12 hours. To the reaction mixture, water was added, and the reaction mixture was extracted with chloroform. The obtained organic layer was washed with saturated brine, and then dried over anhydrous sodium sulfate and concentrated under reduced pressure. The resulting residue was subjected to a silica gel chromatography to give Intermediate compound 11 shown below 2.75 g.
Intermediate Compound 11:

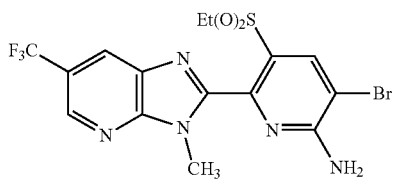

$^1$H-NMR (CDCl$_3$) δ: 8.74 (1H, s), 8.39 (1H, s), 8.29 (1H, s), 5.69 (2H, br s), 3.85 (3H, s), 3.64 (2H, q, J=7.5 Hz), 1.33 (3H, t, J=7.5 Hz).

Reference Preparation Example 2

A mixture of 2-(2-chloro-4-ethylsulfanylpyridin-3-yl)-5-(trifluoromethylthio)benzoxazole 3.0 g, cesium carbonate 2.5 g, 4-methoxybenzylamine 2 mL, and N-methylpyrrolidone 10 mL was stirred at 180° C. for 2 hours. To the reaction mixture, water was added to precipitate a solid. The obtained solid was washed with water and dried to give Intermediate Compound 12 shown below 2.69 g.

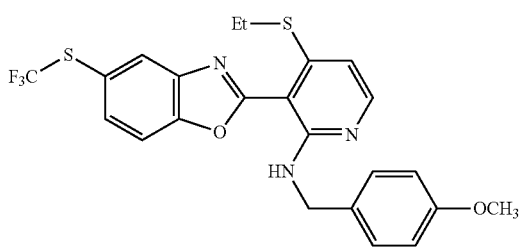 [SMILES: CCSc1ccnc(NCc2ccc(OC)cc2)c1-c1nc2cc(SC(F)(F)F)ccc2o1]

Intermediate Compound 12
$^1$H-NMR (CDCl3) δ: 9.19 (1H, s), 8.10 (1H, d, J=5.5 Hz), 8.02 (1H, s), 7.34 (2H, d, J=8.7 Hz), 6.89 (2H, d, J=8.7 Hz), 6.57 (1H, d, J=5.7 Hz), 4.79 (2H, d, J=5.3 Hz), 3.81 (3H, s), 3.04 (2H, q, J=7.4 Hz), 1.43 (3H, t, J=7.4 Hz).

Reference Preparation Example 3

A mixture of Intermediate compound 12 2.69 g and trifluoroacetic acid 10 mL was stirred at room temperature for 4 hours. The reaction mixture was concentrated under reduced pressure, and to the resulting residue were added 2 M sodium hydroxide solution and water, and the reaction mixture was extracted with chloroform. The obtained organic layer was washed with saturated brine, and then dried over anhydrous sodium sulfate and concentrated under reduced pressure. The resulting residue was subjected to a silica gel chromatography to give Intermediate compound 13 shown below 1.92 g.

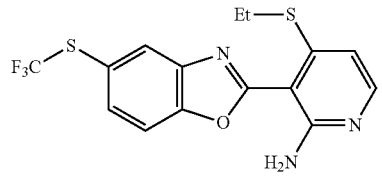 [SMILES: CCSc1ccnc(N)c1-c1nc2cc(SC(F)(F)F)ccc2o1]

Intermediate Compound 13
$^1$H-NMR (CDCl$_3$) δ: 8.16 (1H, s), 7.78-7.75 (2H, m), 7.71 (1H, d, J=6.8 Hz), 6.77 (1H, d, J=6.8 Hz), 3.17 (2H, q, J 7.5 Hz), 1.52 (3H, t, J=7.5 Hz).

The compound prepared according to the method described in the Reference preparation example 3 and its physical properties are shown as follows.

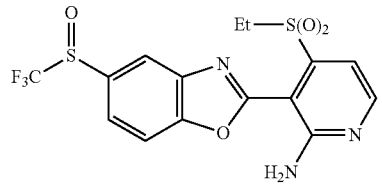

Intermediate Compound 14
$^1$H-NMR (CDCl$_3$) δ: 8.51 (1H, d, J=5.3 Hz), 8.29 (1H, s), 7.88 (1H, d, J=8.5 Hz), 7.83 (1H, dd, J=8.6, 0.6 Hz), 7.37 (1H, d, J=5.0 Hz), 6.18 (2H, s), 3.65 (2H, q, J=7.5 Hz), 1.47 (3H, t, J=7.4 Hz).

Next, the formulation examples of the present compound are shown below. The "parts" represents "part by weight".

Formulation Example 1

Into a mixture of 10 parts of any one of the present compounds 1 to 26, 35 parts of xylene, and 35 parts of DMF, 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrous silicon oxide fine powder, and 54 parts of diatomaceous earth are mixed, and further 20 parts of any one of the present compounds 1 to 26 is added thereto, followed by mixing them to obtain each wettable powder.

Formulation Example 3

To 2 parts of any one of the present compounds 1 to 26, 1 part of synthetic hydrous silicon oxide fine powder, 2 parts of calcium lignin sulfonate, 30 parts of bentonite, and 65 parts of kaolin clay are added, followed by mixing them. To the mixtures is then added an appropriate amount of water, and the mixtures are further mixed, granulated with a granulator, and forced-air dried to obtain each granular formulation.

Formulation Example 4

Into an appropriate amount of acetone, 1 part of any one of the present compounds 1 to 26 is mixed, and then 5 parts of synthetic hydrous silicon oxide fine powder, 0.3 parts of isopropyl acid phosphate, and 93.7 parts of kaolin clay are added, followed by mixing them with stirring thoroughly and removal of acetone from the mixture by evaporation to obtain each powder formulation.

Formulation Example 5

A mixture of 35 parts of polyoxyethylene alkyl ether sulfate ammonium salt and white carbon (weight ratio of 1:1), 10 parts of any one of the present compounds 1 to 26, and 55 parts of water are mixed, followed by finely grinding them by a wet grinding method to obtain each flowable formulation.

Formulation Example 6

Into a mixture of 5 parts of xylene and 5 parts of trichloroethane, 0.1 parts of any one of the present compounds 1 to 26 are mixed, and the resulting mixture is then mixed with 89.9 parts of kerosene to obtain each oil solution.

Formulation Example 7

Into 0.5 ml of acetone, 10 mg of any one of the present compounds 1 to 26 is mixed, and the solution is added dropwise to 5 g of a solid feed powder for an animal (solid feed powder for rearing and breeding CE-2, manufactured by CLEA Japan, Inc.), followed by mixing the resulting mixtures uniformly. Acetone is then dried by evaporation from the mixtures to obtain each poison bait.

Formulation Example 8

Into an aerosol can, 0.1 parts of any one of the present compounds 1 to 26 and 49.9 parts of kerosene are poured. After mounting an aerosol valve, 25 parts of dimethyl ether and 25 parts of LPG are filled, followed by shaking the mixtures, and further mounting an actuator to obtain each oily aerosol.

Formulation Example 9

A mixture of 0.6 parts of any one of the present compounds 1 to 26, 0.01 parts of BHT (2,6-di-tert-butyl-4-methylphenol), 5 parts of xylene, 3.39 parts of kerosene, and 1 part of an emulsifier {Rheodol MO-60 (manufactured by Kao Corporation)}, and 50 parts of distilled water are filled into an aerosol container, and a valve part of the container is attached. Then, 40 parts of a propellant (LPG) is filled therein through the valve under pressure to obtain each aqueous aerosol.

Formulation Example 10

Zero-point-one (0.1) parts of any one of the present compounds 1 to 26 is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 11

Five (5) parts of any one of the present compounds 1 to 26, and 95 parts of ethylene-methyl methacrylate copolymer (the ratio of the methyl methacrylate in the copolymer:10 weight %, Acryft (registered by trademark) WD 301, manufactured by Sumitomo Chemical Co. Ltd.) are melted and kneaded with a closed type pressure kneader (manufactured by Moriyama Manufacturing Co., Ltd.), and the resulting kneaded product is extruded from an extrusion molding machine through a molding die to obtain each rod-shaped molded product having a length of 15 cm and a diameter of 3 mm.

Formulation Example 12

Five (5) parts of any one of the present compounds 1 to 26, and 95 parts of plasticized polyvinyl chloride resin are melted and kneaded with a closed type pressure kneader (manufactured by Moriyama Manufacturing Co., Ltd.), and the resulting kneaded product is extruded from an extrusion molding machine through a molding die to obtain each rod-shaped molded product having a length of 15 cm and a diameter of 3 mm.

Formulation Example 13

One-hundred (100) mg of any one of the present compounds 1 to 26, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 14

Twenty-five (25) mg of any one of the present compounds 1 to 26, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 15

To 100 mg of any one of the present compounds 1 to 26, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum K (manufactured by Vanderbilt Co.), 35 mg of a perfume, and 500 mg of a coloring agent, distilled water is added so that a final volume is set to be 100 mL, followed by mixing the mixtures to obtain each suspension for oral administration.

Formulation Example 16

Into a mixture of 5% by weight of an emulsifier, 3% by weight of benzyl alcohol and 30% by weight of propylene glycol, 5% by weight of any one of the present compounds 1 to 26 is mixed, and phosphate buffer is added thereto so that a pH of the solution is set to be 6.0 to 6.5, and water is added as the rest parts to obtain each solution for oral administration.

Formulation Example 17

To a mixture of 57% by weight of fractional distillated palm oil and 3% by weight of polysorbate 85, 5% by weight of aluminium distearate is added, and heated to disperse it. The resulting mixtures are cooled to room temperature, and 25% by weight of saccharin is dispersed in an oil vehicle. Ten (10) % by weight of any one of the present compounds 1 to 26 is divided thereto to obtain each paste for oral administration.

Formulation Example 18

Five (5)% by weight of any one of the present compounds 1 to 26 is mixed with 95% by weight of limestone filler, followed by a wet-granulation of the resulting mixture to obtain each granule for oral administration.

Formulation Example 19

Into 80 parts of diethylene glycol monoethyl ether, 5 parts of any one of the present compounds 1 to 26 is mixed, and 15 parts of propylene carbonate is added thereto, and the resulting mixture is mixed to obtain each spot-on solution.

Formulation Example 20

Into 70 parts of diethylene glycol monoethyl ether, 10 parts of any one of the present compounds 1 to 26 is mixed, and 20 parts of 2-octyldodecanol is added thereto to obtain each pour-on solution.

Formulation Example 21

To 0.5 parts of any one of the present compounds 1 to 26, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly to obtain a homogeneous solution, and 19.5 parts of water is then added thereto and the resulting mixture is further mixed with stirring thoroughly to obtain a homogeneous solution of each shampoo formulation.

Formulation Example 22

Zero-point-fifteen (0.15)% by weight of any one of the present compounds 1 to 26, 95% by weight of animal feed, as well as 4.85% by weight of a mixture of dibasic calcium phosphate, diatomaceous earth, Aerosil, and carbonate (or chalk) are mixed with stirring thoroughly to obtain each premix for animal feed.

Formulation Example 23

Seven-point-two (7.2) g of any one of the present compounds 1 to 26, and 92.8 g of Hosco (registered trademark) S-55 (manufactured by Maruishi Pharmaceuticals) are melted and mixed at 100° C., and the resulting mixtures are poured into a suppository mold, followed by performing a cooling solidification to obtain each suppository.

Next, Test examples are used to show an efficacy of the present compounds on controlling harmful arthropods. The following Test examples were conducted at 25° C.

Test Example 1

Test compounds are made to a formulation according to the method described in the Formulation example 5, and thereto is added water containing 0.03 v/v % of a spreader to prepare a diluted solution containing a prescribed concentration of the test compound.

Cucumber (*cucumber sativus*) seedling (on the developmental stage of the second true leaf) is planted in a plastic cup, and approximately 30 heads of cotton aphid (*Aphis gossypii*) (all stages of life) are released onto the seedling of the cucumber. After 1 day, the diluted solutions are sprayed into the seedling at a ratio of 10 mL/seedling. After 5 days, the number of the surviving insects is examined and the controlling value is calculated by the following equation.

Controlling value (%)={1−($Cb$×$Tai$)/($Cai$×$Tb$)}×100 wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group; Here the "untreated group" represents a group where a similar treatment procedure to that of treated group except not using the test compound is done.

The results of the test that was conducted according to the method described in the Test example 1 are shown as follows.

The test was conducted by making the prescribed concentration 500 ppm and using the below-mentioned present compounds as a test compound, and, as the result of the test, the test compounds showed 90% or more as the controlling value.

Present compound Nos: 2, 3, 4, 5, 6, 7, 8, 9, 10, 11, 12, 14, 15, 16, 17, 18, 19, 20, 21, and 22.

Test Example 2

Test compounds are made to a formulation according to the method described in the Formulation example 5, and thereto is added water containing 0.03 v/v % of a spreader to prepare a diluted solution containing a prescribed concentration of the test compound.

Rice (*Oryza sativa*) seedling (on the developmental stage of the second true leaf) is planted in a plastic cup, and the diluted solutions are sprayed into the seedling at a ratio of 10 mL/seedling. Thereafter, 20 heads of brown planthopper (*Nilaparvata lugens*) at the third instar larval stage are released onto the seedling of the rice. After 6 days, the number of the surviving insects is examined, and the mortality is calculated by the following equation.

Mortality (%)=(1−Number of surviving insects/20)×100

The results of the test that was conducted according to the method described in the Test example 2 are shown as follows.

The test was conducted by making the prescribed concentration 500 ppm and using the below-mentioned present compounds as a test compound, and, as the result of the test, the test compounds showed 90% or more as the mortality of insects.

Present compound Nos: 2, 3, 5, 9, 10, 11, 12, 14, 16, 19, and 20.

Test Example 3

Test compounds are made to a formulation according to the method described in the Formulation example 5, and thereto is added water containing 0.03 v/v % of a spreader to prepare a diluted solution containing a prescribed concentration of the test compound.

The diluted solutions are sprayed into cabbage (*Brassicae oleracea*) seedling (on the developmental stage of the second to third true leaf) that is planted in a plastic cup at a ratio of 20 mL/seedling. Thereafter, the stem and leaf thereof is cut out and then is installed into a plastic cup that is covered with filter paper on the bed of the cup. Five (5) heads of cabbage moth (*Plutella xylostella*) at the second instar larval stage are released into the cup, and the cup is covered with a lid. After 5 days, the number of the surviving insects is counted, and the mortality of insects is calculated by the following equation.

Mortality(%)=(1−Number of surviving insects/5)× 100

The results of the test that was conducted according to the method described in the Test example 3 are shown as follows.

The test was conducted by making the prescribed concentration 500 ppm and using the below-mentioned present compounds as a test compound, and, as the result of the test, the test compounds showed 80% or more as the mortality of insects.

Present compound Nos: 2, 3, 4, 5, 6, 7, 8, 9, 10, 11, 12, 14, 15, 16, 17, 18, 19, 20, 21, and 22.

Test Example 4

Test compounds are made to a formulation according to the method described in the Formulation example 5, and thereto is added water containing 0.03 v/v % of a spreader to prepare a diluted solution containing a prescribed concentration of the test compound.

The diluted solutions are sprayed into cabbage (*Brassicae oleracea*) seedling (on the developmental stage of the fifth to sixth true leaf) that is planted in a plastic cup at a ratio of 20 mL/seedling. Ten (10) heads of tobacco cutworm (*Spodoptera litura*) at the fourth instar larval stage are released into the cup, and kept in the cup covered with a net. After 6 days, the surviving insects are counted, and the mortality of insects is calculated by the following equation.

Mortality (%)=(1−Number of survived insects/10)× 100

The results of the test that was conducted according to the method described in the Test example 4 are shown as follows.

The test was conducted by making the prescribed concentration 200 ppm and using the below-mentioned present compounds as a test compound, and, as the result of the test, the test compounds showed 80% or more as the mortality of insects.

The present compound Nos: 2, 3, 6, 9, 10, 11, 14, 16, 19, 20, 21, and 22.

Test Example 5

Each 1 mg of the test compounds is dissolved into 50 µL of a mixed solution of polyoxyethylene sorbitan mono-cocoate and acetone (polyoxyethylene sorbitan mono-co-coate:acetone=5:95 (v/v ratio)). Thereto is added water containing 0.03% by volume of a spreader to prepare a diluted solution containing a prescribed concentration of the test compound.

Corns (*Zea mays*) are shown on a tray overlaid with damped KimWipes (registered trademark). After corns are grown for 5 days, the entire seedling of the corns is immersed into the diluted solution for 30 seconds. Thereafter, each two grains of the seedlings are installed in a plastic petri dish (90 mm radius), and 10 heads of Western corn rootworm (*Diabrotica virgifera virgifera*) at the second instar larval stage are released into the dish, and the dish is covered with a lid. After 5 days, the number of the died insects is counted, and the mortality of insects is calculated by the following equation.

Mortality (%)=(Number of died insects/10)×100

The results of the test that was conducted according to the method described in the Test example 5 are shown as follows.

The test was conducted by making the prescribed concentration 50 ppm and using the below-mentioned present compounds as a test compound, and, as the result of the test, the test compounds showed 80% or more as the mortality of insects.

The present compound Nos: 3, 5, 9, 11, 12, 13, 16, 17, 20, and 22.

INDUSTRIAL APPLICABILITY

The present compound shows an excellent control effect against a harmful arthropod.

The invention claimed is:

1. A compound represented by formula (II):

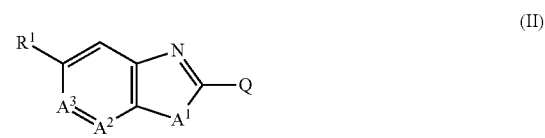

in which Q represents a group represented by formula Q-1 or a group represented by formula Q-2,

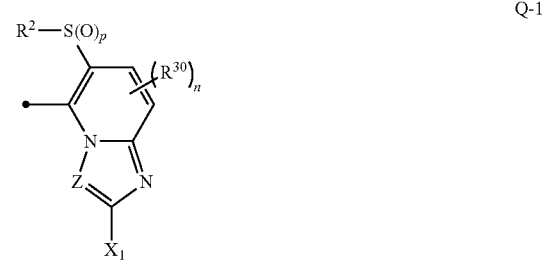

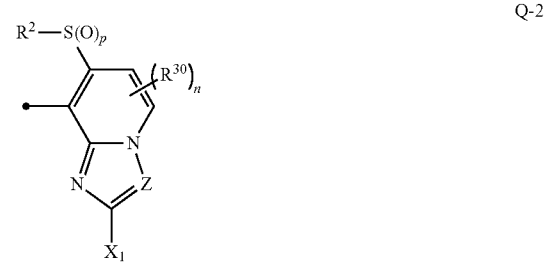

wherein

Z represents a nitrogen atom or $CX^2$, $X^1$ and $X^2$ each independently represent a hydrogen atom, a C1-C6 chain hydrocarbon group optionally having one or more substituents selected from group B, a phenyl group optionally having one or more substituents selected from group C, a 5 or 6 membered aromatic heterocyclic group optionally having one or more substituents selected from group C, a C3-C6 alicyclic hydrocarbon group optionally having one or more substituents selected from group C, a halogen atom, a cyano group, a nitro group, a sulfanyl group, $OR^a$, $NR^bR^e$, $C(O)OR^d$, $C(O)NR^eR^f$, $NR^jC(O)R^g$, $NR^jC(O)OR^h$, or $S(O)_qR^i$, $A^1$ represents NH, NCH$_3$, an oxygen atom, or a sulfur atom, $A^2$ represents a nitrogen atom or CH, $A^3$ represents a nitrogen atom or $CR^4$, $R^1$ represents a C1-C5 perfluoroalkyl group, $S(O)_rR^5$, or $OS(O)_2R^5$, n, p, q, and r each independently represent 0, 1, or 2, $R^2$ represents a C1-C6 alkyl group optionally having one or more halogen atoms, a cyclopropylmethyl group, or a cyclopropyl group, $R^{30}$ represents a C1-C6 chain hydrocarbon group optionally having one or more substituents selected from group B, a C3-C7 cycloalkyl group optionally having one or more substituents selected from group E, a phenyl group optionally having one or more substituents selected from group H, a 5 or 6 membered aromatic heterocylic group optionally having one or more substituents selected from group H, $OR^{12}$, $NR^{11}R^{12}$, $NR^{11a}R^{12a}$, $NR^{29}NR^{11}R^{12}$, $NR^{29}OR^{11}$, $NR^{11}C(O)R^{13}$, $NR^{29}NR^{11}C(O)R^{13}$, $NR^{11}C(O)OR^{14}$, $NR^{29}NR^{11}C(O)OR^{14}$, $NR^{11}C(O)NR^{15}R^{16}$, $NR^{24}NR^{11}C(O)NR^{15}R^{16}$, N=CHNR$^{15}$R$^{16}$, N=S(O)$_x$R$^{15}$R$^{16}$, $C(O)OR^{17}$, a cyano group, a nitro group, or a halogen atom, $R^{11}$, $R^{17}$, $R^{24}$, and $R^{29}$ each independently represent a hydrogen atom, or a C1-C6 chain hydrocarbon group optionally having one or more halogen atoms, $R^{11a}$ and $R^{12a}$ are taken together with the nitrogen atom to which they are attached to form a 3 to 7 membered non-aromatic heterocyclic group optionally having one or more substituents selected from group E, $R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from group H, or a 5 or 6 membered aromatic heterocyclic group optionally having one or more substituents selected from group H, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group wherein a phenyl moiety of the phenyl C1-C3 alkyl group may optionally have one or more substituents selected from group H, $R^{15}$ and $R^{16}$ each independently represent a C1-C6 alkyl group optionally having one or more halogen atoms, $R^{12}$ represents a hydrogen atom, $S(O)_2R^{23}$, a C1-C6 chain hydrocarbon group optionally having one or more halogen atoms, or a C1-C6 alkyl group having one substituent selected from group F, $R^{23}$ represents a C1-C6 chain hydrocarbon group optionally having one or more halogen atoms, or a phenyl group optionally having one or more substituents selected from group H, $R^4$ represents a hydrogen atom, a C1-C6 alkyl group optionally having one or more halogen atoms, or a halogen atom, $R^5$ represents a C1-C5 perfluoroalkyl group, $R^a$, $R^b$, and $R^c$ each independently represent a hydrogen atom, or a C1-C6 chain hydrocarbon group optionally having one or more halogen atoms, $R^d$ represents a hydrogen atom or a C1-C6 chain hydrocarbon group, $R^e$ and $R^f$ each independently represent a hydrogen atom, a C1-C6 chain hydrocarbon group optionally having one or more halogen atoms, or a C3-C6 alicyclic hydrocarbon group optionally having one or more halogen atoms, $R^g$ and $R^h$ each independently represent a hydrogen atom, a C1-C6 chain hydrocarbon group optionally having one or more halogen atoms, a C3-C6 alicyclic hydrocarbon group optionally having one or more halogen atoms, or a phenyl group, $R^i$ represents a C1-C6 chain hydrocarbon group optionally having one or more halogen atoms, $R^j$ represents a hydrogen atom or a C1-C6 alkyl group, group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom, group C: a group consisting of a C1-C6 alkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom, group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxyl group, a cyano group, and a nitro group, group F: a group consisting of a C1-C6 alkoxy group optionally having one or more halogen atoms, an amino group, NHR$^{21}$, NR$^{21}$R$^{22}$, a cyano group, a phenyl group optionally having one or more substituents selected from group H, a 5 or 6 membered aromatic heterocyclic group optionally having one or more substituents selected from group H, a C3-C7 cycloalkyl group optionally having one or more halogen atoms, and a 3 to 7 membered non-aromatic heterocyclic group optionally having one or more substituents selected from group C, group H: a group consisting of a halogen atom, a nitro group, a cyano group, an amino group, a 5 or 6 membered aromatic heterocyclic group, a C1-C6 alkyl group optionally having one or more halogen atoms, $OR^{100}$, $NR^9R^{100}$, $C(O)R^{100}$, $C(O)NR^9R^{100}$, $OC(O)R^9$, $OC(O)OR^9$, $NR^{100}C(O)R^9$, $NR^{100}C(O)OR^9$, and $C(O)OR^{100}$, $R^9$ represents a C1-C6 alkyl group optionally having one or more halogen atoms, or a C3-C6 cycloalkyl group optionally having one or more halogen atoms, and $R^{100}$ represents a hydrogen atom, a C1-C6 alkyl group optionally having one or more halogen atoms, or a C3-C6 cycloalkyl group optionally having one or more halogen atoms.

2. The compound according to claim 1 represented by formula (I):

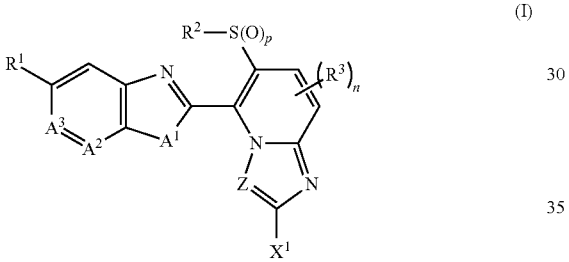

wherein

Z represents a nitrogen atom or $CX^2$, $X^1$ and $X^2$ each independently represent a hydrogen atom, a C1-C6 chain hydrocarbon group optionally having one or more substituents selected from group B, a phenyl group optionally having one or more substituents selected from group C, a 5 or 6 membered aromatic heterocyclic group optionally having one or more substituents selected from group C, a C3-C6 alicyclic hydrocarbon group optionally having one or more substituents selected from group C, a halogen atom, a cyano group, a nitro group, a sulfanyl group, $OR^a$, $NR^bR^e$, $C(O)OR^d$, $C(O)NR^eR^f$, $NR^jC(O)R^g$, $NR^jC(O)OR^h$, or $S(O)_qR^i$, $A^1$ represents NH, $NCH_3$, an oxygen atom, or a sulfur atom, $A^2$ represents a nitrogen atom or CH, $A^3$ represents a nitrogen atom or $CR^4$, $R^1$ represents a C1-C5 perfluoroalkyl group, S(O),$R^5$, or $OS(O)_2R^5$, n, p, q, and r each independently represent 0, 1, or 2, $R^2$ represents a C1-C6 alkyl group optionally having one or more halogen atoms, a cyclopropylmethyl group, or a cyclopropyl group, $R^3$ represents a C1-C6 alkyl group optionally having one or more halogen atoms, or a halogen atom, $R^4$ represents a hydrogen atom, a C1-C6 alkyl group optionally having one or more halogen atoms, or a halogen atom, $R^5$ represents a C1-C5 perfluoroalkyl group, $R^a$, $R^b$, and $R^c$ each independently represent a hydrogen atom, or a C1-C6 chain hydrocarbon group optionally having one or more halogen atoms, $R^d$ represents a hydrogen atom, or a C1-C6 chain hydrocarbon group, $R^e$ and $R^f$ each independently represent a hydrogen atom, a C1-C6 chain hydrocarbon group optionally having one or more halogen atoms, or a C3-C6 alicyclic hydrocarbon group optionally having one or more halogen atoms, $R^g$ and $R^h$ each independently represent a hydrogen atom, a C1-C6 chain hydrocarbon group optionally having one or more halogen atoms, a C3-C6 alicyclic hydrocarbon group optionally having one or more halogen atoms, or a phenyl group, $R^i$ represents a C1-C6 chain hydrocarbon group optionally having one or more halogen atoms, $R^j$ represents a hydrogen atom or a C1-C6 alkyl group, group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom, group C: a group consisting of a C1-C6 alkyl group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a nitro group, a hydroxyl group, an amino group, a C1-C6 alkylamino group, a di(C1-C6 alkyl)amino group, and a halogen atom.

3. The compound according to claim 1, wherein $A^1$ represents an oxygen atom.

4. The compound according to claim 1, wherein $A^1$ represents $NCH_3$.

5. The compound according to claim 1, wherein $A^2$ represents a nitrogen atom, and $A^3$ represents CH.

6. The compound according to claim 1, wherein $A^2$ represents CH, and $A^3$ represents CH.

7. The compound according to claim 1, wherein Z represents a nitrogen atom.

8. The compound according to claim 1, wherein Z represents CH.

9. The compound according to claim 1, wherein $R^2$ represents a C1-C3 alkyl group.

10. The compound according to claim 1, wherein $X^1$ represents a hydrogen atom, a C1-C6 alkyl group optionally having one or more halogen atoms, a phenyl group optionally having one or more halogen atoms, a halogen atom, $OR^a$, $NR^bR^c$, $C(O)OR^d$, or $C(O)NR^eR^f$, and $R^a$, $R^b$, $R^c$, $R^d$, $R^e$, and $R^f$ each independently represent a hydrogen atom or a C1-C6 alkyl group.

11. The compound according to claim 1, wherein Z represents a nitrogen atom or CH, $A^1$ represents an oxygen atom, $A^2$ represents CH, $A^3$ represents CH, $X^1$ represents a hydrogen atom, a C1-C6 alkyl group optionally having one or more halogen atoms, $NR^bR^c$, $C(O)OR^d$, a halogen atom, or a phenyl group, $R^b$, $R^c$, and $R^d$ represent a hydrogen atom or a C1-C6 alkyl group, $R^1$ represents a C1-C5 perfluoroalkyl group or $S(O)_nR^5$, $R^2$ represents a C1-C3 alkyl group, and n represents 0 or 1.

12. The compound according to claim 1, wherein Z represents a nitrogen atom or CH, $A^1$ represents $NCH_3$, $A^2$ represents a nitrogen atom, $A^3$ represents CH, $X^1$ represents a hydrogen atom, a C1-C6 alkyl group optionally having one or more halogen atoms, $NR^bR^c$, $C(O)OR^d$, a halogen atom, or a phenyl group, $R^b$, $R^c$, and $R^d$ represent a hydrogen atom or a C1-C6 alkyl group, $R^1$ represents a C1-C5 perfluoroalkyl group, $R^2$ represents a C1-C3 alkyl group, and n represents 0 or 1.

13. The compound according to claim 1, wherein Z represents a nitrogen atom or CH, $X^1$ represents a hydrogen atom, a C1-C6 alkyl group optionally having one or more halogen atoms, $NR^bR^c$, $C(O)OR^d$, a halogen atom, or a phenyl group, $R^b$, $R^c$, $R^d$ represent a hydrogen atom or a C1-C6 alkyl group, $R^1$ represents a C1-C5 perfluoroalkyl group, $R^2$ represents a C1-C3 alkyl group, $R^{30}$ represents a C1-C6 alkyl group optionally having one or more halogen atoms, a C3-C7 cycloalkyl group optionally having a cyano group, a halogen atom, or a phenyl group having a C1-C6 alkyl group optionally having one or more halogen atoms or a halogen atom, and n represents 0 or 1.

14. A composition for controlling a harmful arthropod, comprising the compound according to claim 1, and an inert carrier.

15. A method for controlling a harmful arthropod, comprising applying an effective amount of the compound according to claim 1 to a harmful arthropod or a habitat where the harmful arthropod lives.

\* \* \* \* \*